US008945508B2

(12) United States Patent
Baker, Jr. et al.

(10) Patent No.: US 8,945,508 B2
(45) Date of Patent: Feb. 3, 2015

(54) DENDRIMER COMPOSITIONS AND METHODS OF SYNTHESIS

(75) Inventors: James R. Baker, Jr., Ann Arbor, MI (US); Baohua Huang, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 6 days.

(21) Appl. No.: 13/502,004

(22) PCT Filed: Oct. 7, 2010

(86) PCT No.: PCT/US2010/051835
§ 371 (c)(1),
(2), (4) Date: Jun. 19, 2012

(87) PCT Pub. No.: WO2011/059609
PCT Pub. Date: May 19, 2011

(65) Prior Publication Data
US 2012/0259098 A1    Oct. 11, 2012

Related U.S. Application Data

(60) Provisional application No. 61/251,244, filed on Oct. 13, 2009.

(51) Int. Cl.
*A61K 51/00* (2006.01)
*A61M 36/14* (2006.01)
*A61K 47/48* (2006.01)
*A61K 49/00* (2006.01)
*A61K 51/06* (2006.01)
*C08G 73/02* (2006.01)
*A61K 49/12* (2006.01)

(52) U.S. Cl.
CPC ....... *A61K 47/48207* (2013.01); *A61K 49/0002* (2013.01); *A61K 49/0043* (2013.01); *A61K 49/0054* (2013.01); *A61K 51/065* (2013.01); *C08G 73/028* (2013.01); *A61K 49/124* (2013.01)
USPC ...................................... 424/1.11

(58) Field of Classification Search
CPC ................................. A61K 49/0054
See application file for complete search history.

(56) References Cited

U.S. PATENT DOCUMENTS

| 4,161,948 | A | 7/1979 | Bichon |
| 4,507,466 | A | 3/1985 | Tomalia et al. |
| 4,558,120 | A | 12/1985 | Tomalia et al. |
| 4,568,737 | A | 2/1986 | Tomalia et al. |
| 4,587,329 | A | 5/1986 | Tomalia et al. |
| 4,631,337 | A | 12/1986 | Tomalia et al. |
| 4,694,064 | A | 9/1987 | Tomalia et al. |
| 4,708,930 | A | 11/1987 | Kortright et al. |
| 4,713,975 | A | 12/1987 | Tomalia et al. |
| 4,737,550 | A | 4/1988 | Tomalia et al. |
| 4,743,543 | A | 5/1988 | Kortright |
| 4,827,945 | A | 5/1989 | Groman |
| 4,857,599 | A | 8/1989 | Tomalia et al. |
| 4,871,779 | A | 10/1989 | Killat et al. |
| 4,892,935 | A | 1/1990 | Yoshida et al. |
| 4,914,021 | A | 4/1990 | Toth et al. |
| 4,918,164 | A | 4/1990 | Hellstrom et al. |
| 4,921,789 | A | 5/1990 | Salem et al. |
| 4,921,790 | A | 5/1990 | OBrien |
| 4,939,240 | A | 7/1990 | Chu et al. |
| 4,946,778 | A | 8/1990 | Ladner et al. |
| 4,963,484 | A | 10/1990 | Kufe |
| 4,965,128 | A | 10/1990 | Greidanus |
| 5,041,516 | A | 8/1991 | Frechet et al. |
| 5,053,489 | A | 10/1991 | Kufe |
| 5,110,911 | A | 5/1992 | Samuel et al. |
| 5,270,163 | A | 12/1993 | Gold et al. |
| 5,338,532 | A | 8/1994 | Tomalia et al. |
| 5,354,308 | A | 10/1994 | Simon et al. |
| 5,387,617 | A | 2/1995 | Hedstrand et al. |
| 5,393,795 | A | 2/1995 | Hedstrand et al. |
| 5,393,797 | A | 2/1995 | Hedstrand et al. |
| 5,475,096 | A | 12/1995 | Gold et al. |
| 5,512,443 | A | 4/1996 | Schlom et al. |
| 5,527,524 | A | 6/1996 | Tomalia et al. |
| 5,545,530 | A | 8/1996 | Satomura et al. |

(Continued)

FOREIGN PATENT DOCUMENTS

| CA | 2187921 | 11/1995 |
| CA | 2386998 | 4/2011 |

(Continued)

OTHER PUBLICATIONS

Abel et al., "The Selective Concentration of Sulpha-diazine and Related Compounds in Malignant Tissue," Eur. J. Cancer 9:4 (1973).
Abrams, et al., "Programmed cell death during Drosophila embryogenesis," Development 117:29 (1993).
Adlish et al., "Identification of a Putative Cell Receptor for Human Cytomegalovirus," Virology 176:337 (1990).
Akutsu et al., "Schedule-dependent Interaction Between Paclitaxel and Doxorubicin in Human Cancer Cell Lines in Vitro," Eur. J. Cancer 31A:2341 (1995).

(Continued)

*Primary Examiner* — Michael G Hartley
*Assistant Examiner* — Melissa Perreira
(74) *Attorney, Agent, or Firm* — Casimir Jones S.C.

(57) ABSTRACT

The present invention relates to novel dendrimer compounds and methods of synthesizing the same. In particular, the present invention is directed to novel polyamidoamine (PAMAM) dendrimers, novel dendrimer branching units, methods for synthesizing such novel PAMAM dendrimers and functionalized dendrimers, as well as systems and methods utilizing the dendrimers (e.g., in diagnostic and/or therapeutic settings (e.g., for the delivery of therapeutics, imaging, and/or targeting agents (e.g., in disease diagnosis and/or therapy, etc.))).

6 Claims, 32 Drawing Sheets

(56) References Cited

U.S. PATENT DOCUMENTS

| | | | |
|---|---|---|---|
| 5,560,929 A | 10/1996 | Hedstrand et al. |
| 5,631,329 A | 5/1997 | Yin et al. |
| 5,661,025 A | 8/1997 | Szoka et al. |
| 5,674,192 A | 10/1997 | Sahatjian |
| 5,693,014 A | 12/1997 | Abele et al. |
| 5,693,763 A | 12/1997 | Codington et al. |
| 5,714,166 A | 2/1998 | Tomalia et al. |
| 5,733,303 A | 3/1998 | Israel |
| 5,755,722 A | 5/1998 | Barry |
| 5,773,527 A | 6/1998 | Tomalia et al. |
| 5,792,105 A | 8/1998 | Lin |
| 5,795,582 A | 8/1998 | Wright |
| 5,800,391 A | 9/1998 | Kontos |
| 5,800,508 A | 9/1998 | Goicoechea et al. |
| 5,800,519 A | 9/1998 | Sandock |
| 5,808,005 A | 9/1998 | Codington et al. |
| 5,843,089 A | 12/1998 | Sahatjian |
| 5,851,228 A | 12/1998 | Pinheiro |
| 5,855,866 A | 1/1999 | Thorpe |
| 5,855,881 A | 1/1999 | Loike et al. |
| 5,857,998 A | 1/1999 | Barry |
| 5,861,319 A | 1/1999 | Lin |
| 5,866,561 A | 2/1999 | Ungs |
| 5,868,719 A | 2/1999 | Tsukernik |
| 5,876,445 A | 3/1999 | Andersen |
| 5,892,019 A | 4/1999 | Schlom |
| 5,892,020 A | 4/1999 | Mezes |
| 5,898,005 A | 4/1999 | Singh |
| 5,902,863 A | 5/1999 | Dvornic et al. |
| 5,908,413 A | 6/1999 | Lange |
| 5,913,894 A | 6/1999 | Schmitt |
| 5,922,887 A | 7/1999 | Dondio et al. |
| 5,933,145 A | 8/1999 | Meek |
| 5,935,114 A | 8/1999 | Jang |
| 6,051,429 A | 4/2000 | Hawley-Nelson et al. |
| 6,054,444 A | 4/2000 | Jackson |
| 6,267,987 B1 | 7/2001 | Park et al. |
| 6,312,679 B1 | 11/2001 | Tomalia et al. |
| 6,471,968 B1 | 10/2002 | Baker et al. |
| 6,475,994 B2 * | 11/2002 | Tomalia et al. ............. 514/44 R |
| 6,485,718 B1 | 11/2002 | Parthasarathy |
| 6,585,956 B2 | 7/2003 | Malik et al. |
| 6,869,772 B2 | 3/2005 | Lichtman et al. |
| 7,078,461 B2 | 7/2006 | Tomalia |
| 7,097,856 B2 | 8/2006 | Frechet |
| 7,208,486 B2 | 4/2007 | Burnett |
| 7,261,875 B2 | 8/2007 | Li |
| 7,368,512 B2 | 5/2008 | Newkome |
| 7,419,686 B2 | 9/2008 | Kaiko et al. |
| 7,459,145 B2 | 12/2008 | Bao |
| 7,572,459 B2 | 8/2009 | Matthews |
| 7,745,229 B2 | 6/2010 | Wang |
| 2001/0031498 A1 | 10/2001 | Leclercq |
| 2002/0165179 A1 | 11/2002 | Baker, Jr. |
| 2003/0180250 A1 | 9/2003 | Chauhan et al. |
| 2004/0109842 A1 | 6/2004 | Baker, Jr. |
| 2004/0120979 A1 | 6/2004 | Roessler et al. |
| 2005/0214247 A1 | 9/2005 | Shaunak |
| 2006/0057211 A1 | 3/2006 | Chorny |
| 2007/0020620 A1 | 1/2007 | Finn |
| 2007/0041934 A1 | 2/2007 | Williams |
| 2007/0298006 A1 | 12/2007 | Tomalia et al. |
| 2008/0045689 A1 | 2/2008 | Stumbe et al. |
| 2008/0171067 A1 | 7/2008 | Govindan et al. |
| 2008/0200562 A1 | 8/2008 | Yin |
| 2008/0312344 A1 | 12/2008 | Liskamp |
| 2009/0012035 A1 | 1/2009 | Jacobson et al. |
| 2009/0053139 A1 | 2/2009 | Shi |
| 2009/0069561 A1 | 3/2009 | Fokin et al. |
| 2009/0082537 A1 | 3/2009 | Ramon Hernandez et al. |
| 2009/0088376 A1 | 4/2009 | Baker, Jr. |
| 2009/0104119 A1 | 4/2009 | Majoros |
| 2009/0208580 A1 | 8/2009 | Shi |
| 2009/0287005 A1 | 11/2009 | Baker, Jr. |
| 2010/0136614 A1 | 6/2010 | Luo et al. |
| 2010/0158850 A1 | 6/2010 | Baker, Jr. |
| 2010/0160299 A1 | 6/2010 | Baker, Jr. |

FOREIGN PATENT DOCUMENTS

| | | |
|---|---|---|
| CN | 101267803 | 9/2008 |
| EP | 0099758 | 10/1984 |
| EP | 0271180 | 6/1988 |
| EP | 1941861 | 7/2008 |
| JP | 2002-265495 | 9/2002 |
| WO | 88/01178 | 2/1988 |
| WO | 88/01180 | 2/1988 |
| WO | 90/02545 | 3/1990 |
| WO | 95/24221 | 9/1995 |
| WO | 95/28641 | 10/1995 |
| WO | 9707398 | 2/1997 |
| WO | 97/38134 | 10/1997 |
| WO | 98/33941 | 8/1998 |
| WO | 99/02651 | 1/1999 |
| WO | 99/07724 | 2/1999 |
| WO | 9961662 | 2/1999 |
| WO | 99/10362 | 3/1999 |
| WO | 99/58656 | 11/1999 |
| WO | 00/16807 | 3/2000 |
| WO | 01/87348 | 11/2001 |
| WO | 0102861 | 11/2001 |
| WO | 03/003975 | 1/2003 |
| WO | 03/011115 | 2/2003 |
| WO | 03/055935 | 7/2003 |
| WO | 06/033766 | 3/2006 |
| WO | 2007/011967 | 1/2007 |
| WO | 2007012001 | 1/2007 |
| WO | 2007/034750 | 3/2007 |
| WO | 2007/080114 | 7/2007 |
| WO | 2008/008483 | 1/2008 |
| WO | 2011002852 | 1/2011 |
| WO | 2011028334 | 3/2011 |
| WO | 2011/059609 | 5/2011 |
| WO | 2011053618 | 5/2011 |
| WO | 2011/072290 | 6/2011 |

OTHER PUBLICATIONS

Australian First Report on Application No. 2005287375 dated Jun. 10, 2008.
Babiuk, Shawn, Foldvari, Marianna, et al., "Cutaneous vaccination: the skin as an immunologically active tissue and the challenge of antigen delivery," Journal of Controlled Release, vol. 66 Issues 2-3, May 15, 2000 pp. 199-214.
Baker et al., "The Synthesis and Testing of Anti-Cancer Therapeutic Nanodevices," Kluwer Academic Publishers, Manufactured in the Netherlands 61-690 (2001).
Baldwin and Saltzman et al., "Materials for protein delivery in tissue engineering" 1998 Advanced Drug Delivery Reviews vol. 33, pp. 71-86.
Balogh and Tomalia, J. Am. Che. Soc. 120:7355 (1998).
Balogh et al., "Formation and Characterization of Dendrimer-Based Water Soluble Inorganic Nanocomposites," Proc. of ACS PMSE 77:118 (1997).
Banga et al., "Assessing the potential of skin electroporation for the delivery of protein- and gene-based drugs," Trends in Biotechnology Vol. 16 Issue 10, Oct. 1, 1998 pp. 408-412.
Baker et al., "Utilization of Lipophilic Ionic Additives in Liquid Polymer Film Optodes for Selective Anion Activity Measurements," Anal. Chem. 69:990 (1997).
Barth et al., "Boron Neutron Capture Therapy of Brain Tumors: Past History, Current Status, and Future Potential," Cancer Invetigation 14:534 (1996).
Barth, et al., "Boronated Starburst Dendrimer-Monoclonal Antibody Immunoconjugates: Evaluation as a Potential Delivery System for Neutron Capture therapy," Bioconjugate Chem. 5:58 (1994).
Baumann et al., "Simultaneous Visualization of the Yellow and Green Forms of the Green Fluorescent Protein in Lving Cells," J. Histochem. Cytochem. 46:1073 (1998).
Bell, "Molecular Trees: A New Branch of Chemistry," Science 271:1077-1078 (1996).

(56) References Cited

OTHER PUBLICATIONS

Bielinska A. et al., "Regulation of in Vitro Gene Expression Using Antisense Oligonucleotides or . . . " Jun. 1, 1996 Nucleic Acids Research, Oxford University Press, Surrey, GB vol. 24 No. 11.
Bielinska et al. Bioconj Chem 10:843-850 (1999).
Bielinska et al., "Application of membrane-based dendrimer/DNA complexes for solid phase transfection in vitro and in vivo" May 2000 Biomaterials vol. 21, Issue 9, pp. 877-887.
Bielinska et al., "The interaction of plasmid DNA with polyamidoamine dendrimers: . . . " Biochimica et Biophysica Acta 1353:180-190 (1997).
Binkley et al., "FNA ligands to human nerve growth factor," Nuc. Acids Res. 23(16):3198-205 (1995).
Block, Lawrence, "Medicated Applications", Remington's Pharmaceutical Sciences, edited by Gennaro, 1990, 18th Edition, pp. 1596 and 1597.
Botchway, et al., "Novel Visible and Ultraviolet Light Photogeneration of . . . " Photochem., Photobiol. 67(7):635-40 (1998).
Bourassa et al., "Photochemistry of Roussin's Red Salt . . . " JACS 119:2853-60 (1997).
Bourne, et al., "Evaluation of the Effects of Intravascular MR Contrast Media (Gadolinium Dendrimer) on 3D Time of Flight Magnetic Resonance Angiography of the Body," J. Magn. Reson. Imag., 6:305 (1996).
Brandl et al., "Plastics from Bacteria and for Bacteria: . . . ", Adv. Biochem Eng Biotechnol, 41:77 (1990).
Brasseur et al., "Biological Activities of Phthalocyanines . . . " Photochem., Photobiol., 47:705-11 (1988).
Braunegg et al., "Polyhydroxyalkanoates, biopolyesters from renewable resources: Physiological and engineering aspects,"J. Biotechnol 65(2-3):127 (1998).
Brazeau et al., "In vitro myotoxicity of selected cationic macromolecules used in non-viral gene delivery," Pharm Research 15:680-684 (1998).
Capale et al., "Boronated Epidermal Growth Factor as a Potential Targeting Agent for Boron Neutron Capture Therapy of Brain Tumors," Bioconjugate Chem., 7:7 (1996).
Carel et al., "Structural Requirements for C3d,g/Epstein-Barr Virus Receptor (CR2/CD21) Ligand Binding, Internalization, and Viral Infection," J. Biol. Chem. 265:12293 (1990).
Chan and Nie, "quantum Dot Bioconjugates for Ultrasensitive Nonisotopic Detection," Science 281:2016 (1998).
Chang, et al., "Synthetic Appropaches to Long-Wavelength Absorbing Photosensitizers: Porphyrinone and Derivatives," Proc. SPIE, 1203:281-86 (1990).
Chinese Office Action dated Jan. 16, 2009, CN Patent Application No. 200580034777.9.
Choate et al., "Direct Cutaneous Gene Delivery in Human Genetic Skin Disease," Human Gene Ther 8:1659 (1997).
Choi et al., "Poly(ethylene glycol)-block-poly(L-lysine) Dendrimer: . . . ", Bioconjugate Chem. 10:62-65 (1999).
Cincotta, et al., "Novel Benzophenothiazinium Photosensitizers: Preliminary In-Vivo Results," SPIE Proc. SPIE 1203:202-10 (1990).
Co et al., "Isolation and biochemical characterization of the mammalian reovirus type 3 cell-surface receptor," Proc Natl. Acad. Sci 82:1494 (1985).
Cohen and Tohoku, Exp. Med. 168:351 (1992), Abstract printed on May 1, 2002 (1 page).
Cole et al., "The EBV-Hybridoma Technique and its Application to Human Lung Cancer," in Monoclonal Antibodies and Cancer Therapy, Alan R. Liss, Inc., pp. 77-96 (1985).
Cortese et al., "Identification of biologically active peptides using random libraries displayed on phage," Curr. Opin. Biotechol., 6:73 (1995).
Cote et al., "Generation of human monoclonal antibodies reactive with cellular antigens," Proc. Natl. Acad. Sci. U.S.A. 80:2026-2030 (1983).
Davies, "Synthetic materials for covering burn woulds: Progress towards perfection. Part I. Short term dressing materials," Burns 10:94 (1983).
De Leo and Ford, "Reversible Photolabilzation of NO from Chromium (III)-Coordinated Nitrite. A New Strategy for Nitric Oxide Delivery," JACS 121:1980-81 (1999).
Duncan and Malik, Control Rel. Bioact. Mater. 23:105 (1996).
Duncan and Sat, "Tumour targeting by enhanced permeability and retention (EPR) effect," Ann. Oncol. 9:39 (1998).
Duncan et al., "Polymer Conjugates for Anti-Cancer Agent and DNA Delivery," Polymer Preprints 39:180 (1998).
Dvornic and Tomalia, "Dendritic polymers divergent synthesis: starburst poly(amidoamine) dendrimers," in Salamone (ed.) The Polymeric Materials Encyclopedia: 1996 CRC Press, pp. 1-17.
EP Patent Application No. EP 01 935 316.8, Office Action dated Nov. 30, 2007.
Eppstein et al., "Epidermal growth factor receptor occupancy inhibits vaccinia virus infection," Nature 318:663 (1985).
Levi-Montalcini, "The Nerve Growth Factor Thirty-Five Years Later," In Vitro Cell., Devi. Biol. 23:227 (1987).
Liao, et al., "Chromophore-assisted laser inactivation of proteins is mediated by the photogeneration of free radicals," PNAS 91:2659 (1994).
Luck et al., "Plasma protein adsorption on biodegradable microspheres . . . " J. Control. Rel 55:107 (1998).
Madihally and Matthew, "Porous chitosan scaffolds for tissue engineering," Biomaterials 20(12):1133 (1999).
Majoros and Tomalia, Mar. 18, 2006 Abstract only printed Apr. 20, 2009, "Synthesis and Characterization of Novel POPAM-PAMAM (POMAM) Hybrid Dendrimers as Reactive Modules for Nanodevice Construction" Eight Foresight Conference on Molecular Nanotechnology.
Majoros et al., "PAMAM Dendrimer-based multifunctional conjugate for cancer therapy: synthesis, characterization and functionality," Biomacromolecules, 2006, vol. 7, pp. 572-579.
Majoros, et al., "Acetylation of Poly(amidoamine) Dendrimers," Macromolecules 2003, 36, 5526-5529.
Malik et al., "A PAMAM Dendrimer-Platinate," Proc. Int'l Symp. Control. Rel. Bioact. Mater, 24:107 (1997).
Malik et al., "Dendrimers: Relationshipo between structure and biocompatibility in vitro, and preliminary studies on the biodistribution of (125)I-labelled polyamidoamine dendrimers in vivo," Journal of Controlled Relief 65:133-148 (2000).
Marlin et al., "A soluble form of intercellular adhesion molecule-1 inhibits rhinovirus infection," Nature 344:70 (1990).
Mayer et al., "Matrices for tissue engineering-scaffold structure for a bioartificial liver support system," J. Controlled Release 64(1-3):81 (2000).
Mendelsohn et al., "Cellular Receptor for Poliovirus: Molecular Cloning, . . . " Cell 56:855 (1989).
Monsigny et al., "Characterization and biological implications of membrane lectins in tumor, lymphoid and myeloid cells," Biochemie 70:1633 (1988).
Mosmann, "Rapid Colorimetric Assay for Cellular Growth and Survival: Application to Proliferation and Cytotoxity Assays," J. Immunol. Meth, 65:55 (1983).
Murphy, et al., "Photolytic Release of Nitric Oxide Modulates NMDA Receptor-mediated Transmission but Does not Induce Longterm Potentiation at Hippocampal Synapses," Neuropharm. 33:1375-85 (1994).
Naylor et al., Starburst Dendrimers. 5. Molecular Shape Control, J. Am. Chem. Soc. 111:2339-2341 (1989).
Niemiec et al., "Perifollicular Transgenic Expression of Human Interleukin-1 Rectpro Antagonist Protein following Topical Application of Novel Liposome-Plasmid DNA Formulations In Vivo," J. Pharm Sci. 86:701 (1997).
Orentas et al., "Detection of Epstein-Barr virus EBER sequence in post-transplant lymphoma patients with DNA dendrimers," Journal of Virological Methods 77:153-163 (1999).
Ottl, et al., "Preparation and Photoactivation of Caged Fluorophores and Caged Proteins Using a New Class of Heterobifunctional, Photocleavable Cross-Linking Reagents," Bioconjugate Chem. 9:143 (1998).
Page and Roy, "Synthesis and Biological Properties of Mannosylated Starburst Poly(amidoamine) Dendrimers," Bioconjugate Chem., 8:714 (1997).

(56) References Cited

OTHER PUBLICATIONS

Pan, et al., "Dendrimer modified magnetite nanoparticles for protein immobilization," Journal of Colloid and Interface Science, 2005, vol. 284, pp. 1-6.
Pandey, et al., "Chlorin and Porphyrine Derivatives as Potential Photosensitizers in Photodynamic Therapy," Photochem., Photobiol., 53:65-72 (1991).
Park et al., "Anti-HER2 immunoliposomes for targeted therapy of human tumors," Cancer Lett., 118:153 (1997).
Pasani et al., "Antitumor Complexes of Platinum with Carrier Molecules," Inorg. Chim. Acta 80:99 (1983).
Pavlova et al., "Biocompatible and biodegradable polyurethane polymers," Biomaterials 14(13):1024 (1993).
Pegrarn et al., Proc. Am. Soc. Clin. Oncol. 14:106 (1995).
Penault-Llorca et al., "Expression of FGF and FGF Receptor Genes in Human Breast Cancer," Int. J. Cancer 61:170 (1995).
Pillai V.N.R., "Photoremovable Protecting Groups in Organic Synthesis," Synthesis: 1-26 (1980).
Pratap Singh, "Terminal Groups in Starburst Dendrimers: Activation and Reaction with Proteins", 1998 Bioconnugate Chem. 9:54-63.
Press et al., "Expression of the HER-2/neu proto-oncogene in normal human adult and fetal tissues," Oncogene 5:953 (1990).
Quintana, et al., "Design and Function of a Dendrimer-Based Therapeutic Nanodevice Targeted to Tumor Cells Through the Folate Receptor," Pharmaceutical Research, vol. 19, No. 9, Sep. 2002.
Raczka et al., "The effect of synthetic surfactant Exosurf on gene transfer in mouse lung in vivo," Gene Ther 5:1333 (1998).
Riley, "Wound Healing," Am Fam. Physician 24:107 (1981).
Rinberg "Pnuematic capillary gun for ballistic delivery of microparticles" 2005 Applied Physics Letters vol. 87 pp. 1-3.
Roberts, et al., "Preliminary biological evaluation of oplyamidoamine (PAMAM) Starburst dendrimers," J. Biomed Mater res 30:53 (1996).
Roessler et al., "Substituted β-Cyclodextrins Interact with PAMAM Dendrimer-DNA Complexes and Modify Transfection Efficiency," Biochem. 124-129 (2001).
Ruff, et al., "CD4 receptor binding peptides that block HIV infectivity cause human monocyte chemotaxis," FEBS Letters 211:17 (1987).
Ruponen et al., "Interactions of polymeric and liposomal gene delivery systems with extracellular glycosaminoglycans: physicochemical and transfection studies," Biochmica ET Biophysica Acta 1415:331-341 (1999).
Sacerdote et al., "Vasoactive Intestinal Peptide 1-12: . . . " J. of Neuroscience Research 18:102 (1987).
Schneider, et al., "Distance-dependent fluorescence quenching on gold nanoparticles ensheathed with layer-by-layer assembled polyelectrolytes," Nano Letters, 2006, vol. 6, pp. 530-536.
Segura and Shea, "Materials for Non-Viral Gene Delivery" 2001 Annual Review of Materials Research, vol. 31 pp. 25-46.
Selman et al., "Copper Benzochlorin, a Novel Photosensitizer for Photodynamic Therapy . . . " Photochem. Photobio, 57:681-85 (1993).
Sessler et al., "Tripyrroledimethine-derived ("texaphyrine"-type) . . . " Proc. SPIE, 1426:318-29 (1991).
Sharon and Lis, "Lectins as Cell Recognition Molecules," Science 246:227 (1989).
Shchepinov et al., "Oligonucleotide dendrimers: synthesis and use as polylabelled DNA probes," Nucleic Acids Research 25:4447-4454 (1997).
Shea, "DNA delivery from polymer matrices for tissue engineering," Jun. 1999, Nature Biotechnology.
Shephey et al., "Monoclonal antibody identificaiton ofa 100-kDa membrane protein in HeLa cells and human spinal cord involved in poliovirus attachment," Proc. Natl. Acad. Sci. 85:7743 (1988).
Shortreed, et al., "Directed Energy Transfer Funnels in Dendrimetric Antenna Supermolecules," J. Phys. Chem. 101-6318 (1997).
Singh et al., "Starburst Dendrimers: Enhanced Performance and Flexibility for Immunoassays," Clin. Chem. 40:1845 (1994).
Sooklal, "A Blue-Emitting CdS/Dendrimer Nanocomposite," Adv. Mater, 10:1083 (1998).
Huang, B., et al., "Copper-free click conjugation of methotrexate to a PAMAM dendrimer platform", Tetrahedron Letters, E-pub, Dec. 10, 2010, v. 52, pp. 1411-1414.
Dijk, M.V., et al., "Synthesis and Applications of Biomedical and Pharmaceutical Polymers via Click Chemistry Methodologies," Bioconjugate Chemistry, Nov. 2009, v. 20, No. 11, pp. 2011-2016.
Nimmo, C.M. et al., "Regenerative Biomaterials that 'Click': Simple, Aqueous-Based Protocols for Hydrogel Synthesis, Surface Immoboilization, and 3D Patterning" Bioconjugate Chemistry, Oct. 13, 2011, v. 22, pp. 2199-2209.
Huang, B., et al., "The facile synthesis of multifunctional PAMAM dendrimer conjugates through copper-free click chemistry" Bioorganic & Medicinal Chemistry Letters, Mar. 21, 2012, v. 22, pp. 3152-3156.
International Search Report and Written Opinion mailed Mar. 29, 2013, International Patent Application No. PCT/US2012/066104.
Frechet, Jean M.J., et al., "Reversed-phase high-performance liquid chromatographyj of functionalized dendritic macromolecules," Journal of Chromatography A, 667 (1994), pp. 284-289.
Mullen, et al., "Design, synthesis, and biological functionality of a dendrimer-based modular drug delivery platform," Bioconjugate Chemistry, vol. 22, No. 4, pp. 679-689 (Mar. 22, 2011).
Opsteen, et al., "Modular synthesis of block copolymers via cycloaddition of terminal azide and alkyne functionalized polymers", Chemical Communicaitons, vol. 1, pp. 57-59 (2005).
Yim, et al., "Versatile conjugation of octreotide to dendrimers by cycloaddition ("Click") chemistry to yield high-affinity mulivalent cyclic peptide dendrimers," Bioconjugate Chemistry, vol. 20, No. 7, pp. 1323-1331 (2009).
Esfand et al., "synthesis, Complexation and Pharmaceutical Applications of Tetra-directional Cascade Dendrimers," Pharm Sci., 2:157 (1996).
Farkas et al., "Microscopic and Mesoscopic Spectral Bio-Imaging," SPEI 2678:200 (1997).
Fidler et al., "The Implications of Angiogenesis for the Biology and Therapy of Cancer Metastatis," Cell, 79:185 (1994).
Firey and Rodgers, "Photo-Properties of a Silicon Naphthalocyanine: . . . " Photochem. Photobiol., 45:535-38 (1997).
Folkman et al., "Antiogenesis," Journ. of Biol. Chem. 267(16):10931 (1992).
Folkman et al., "Angiogenic Factors," Science, 235:442 (1987).
Folkman, "Clinical Applications of Research on Angiogenesis," New Eng. J. Med. 333(26):1757 (1995).
Fracasso, et al., "Anti-tumor effects of toxins targeted to the prostate specific membrane antigen," The Prostate, 2002, 53: 9-23.
Frechet, et al., "Self-Condensing Vinyl Polymerization: An Approach to Dendritic Materials," Science 269:1080-1083 (1995).
Frechet, "Functional Polymers and Dendrimers: Reactivity, Molecular Architechture, and Interfacial Energy," Science 263:1710-1715 (1994).
Friedman, "Gene Therapy of Cancer Through Restoration of Tumor-Suppressor Functions?J" Cancer 70:1810 (1992).
Fujiwara et al., "Therapeutic Effect of a Retroviral Wild-Type p53 Expression Vector in an Orthotopic Lung Cancer Model," J. Natl. Cancer Inst., 86:458 (1994).
Gac et al., "Synthesis, Characterisation and In Vivo Behaviour of a Norfloxacin-Poly(L-Lysine Citramide Imide) Conjugate Beraing Mannosyl Residues," J. Drug Target 7(5):393 (2000).
Garcia-Contreras et al., "Biodegradable Cisplatin Microspheres for Direct Brain Injection: Preparation and Characterization," Pharm Dev Tech 2:53 (1997).
Gerwitz et al., "Nucleic Acid Therapeutics: State of the Art and Future Prospects," Blood 92:712 (1998).
Gibb, "Apoptosis as a Measure of Chemosensitivity to Cisplatin and Taxol Therapy in Ovarian Cancer Cell Lines," Gynecologoic Oncology 65:13 (1997).
Goodwin and Meares, Cancer (suppl.) 80:2675 (1997).
Haensler et al., "Polyamidoamine Cascade Polymers Mediate Efficient Transfection of Cells in Culture," Bioconjugate Chem. 4:373-379 (1993).

(56) References Cited

OTHER PUBLICATIONS

Hanisch et al., "Structural Studies on Oncofetal Carbohydrate . . . " Carbohydr. Res. 178:29-47 (1988).
Hawker et al., "Unimolecular Micelles and Globular Amphiphiles: Dendritic Macromolecules as Novel Recyclable Solubilization Agents," J. Chem. Soc. Perkins Trans. 12:1287-1297 (1993).
Hinoda et al., "Immunochemical Characterization of Adenocarcinoma-Associated Antigen YH206," Cancer J. 42:653-658 (1988).
Hockenbery et al., "Bcl-2 Functions in an Antioxidant Pathway to Prevent Apoptosis," Cell 75:241 (1993).
Holister et al., "Dendrimers" 2003 Technology White Papers pp. 1-15.
Huse, et al., "Generation of a Large Combinatorial Library of the Immunoglobulin Repertoire in Phage Lambda," Science 246:1275-1281 (1989).
International Search Report mailed Sep. 8, 2008, PCT/US2007/15976.
International Search Report dated Jul. 8, 2002, PCT/US01/15204.
International Search Report dated Nov. 20, 2001, PCT/US01/40824.
International Search Report mailed Jul. 17, 2006, PCT/US05/30278.
Lester et al., "Infrared Microspectroscopic Imaging of the Cerebellum of Normal and Cytarabine Treated Rats," Cell Mol. Biol. 44:29 (1998).
International Search Report, PCT/Us2008/061023, dated Dec. 16, 2008.
Ishida et al., "Related Glycoproteins from Normal Secretory and Malignant Breast Cells," Tumor Biol. 10:12-22 (1989).
Jain et al., "Controlled Drug Delivery by Biodegradable Poly(Ester) Devices: Different Preparative Approaches," Drug Dev Ind Pharm 24:703 (1998).
Jane et al., "Vector development: a major obstacle in human gene therapy," Annals of Med 30:413 (1998).
Jansen et al., "The Dendritic Box: Shape-Selective Liberation of Encapsulated Guests," J. Am. Chem. Soc. 117:4417-4418 1995.
Jellinek, et al., "Inhibition of Receptor Binding by High-Affinity RNA Ligands to Vascular Endothelial Growth Factor," Biochem 83(34):10450-6 (1994).
Kaner et al., "Fibroblast Growth Factor Receptor is a Portal of Cellular Entry for Herpes Simplex Virus Type 1," Science 248:1410 (1990).
Kannon and Garrett, "Moist Wound Healing with Occlusive Dressings," Ermatol. Surg. 21:583 (1995).
Kerr et al., "Apoptosis: Its Significance in Cancer and Cancer Therapy," Cancer 73:2013 (1994).
Klatzman et al., "T-lymphocyte T4 molecule behaves as the receptor for human retrovirus LAV," Nature 312:767 (1984).
Kirpotin et al., "Sterically Stabilized Anti-HER2 Immunoliposomes: Design and Targeting to Human Breast Cancer Cells in Vitro," Biochem., 36:66 (1997).
Kjeldsen et al., "Preparation and Characterization of Monoclonal Antibodies Directed to the Tumor-associated O-linked . . . " Cancer Res. 48:2214-2220 (1988).
Kohler and Milstein, "Continuous cultures of fused cells secreting antibody of predefined specificity," Nature 256:495-497 (1975).
Kozbor et al.,, "the production of monoclonal antibodies from human lymphocytes," Immunol. Today 4:72 (1983).
Krah, "Characterization of Octyl Glucoside-Solubilized Cell Membrane Receptors for Binding Measles Virus," Virology 172:386 (1989).
Kuhlmann et al., "Reduction of cisplatin toxicity in cultured renal tubular cells by the bioflavonoid quercetin," Arch. Toxicol. 72:536 (1998).
Kukowska-Latallo et al., "Efficient transfer of genetic material into mammalian cells using Starburst polyamidoamine dendrimers," Proc. Natl. Acad. Sci. USA 93:4897-4902 (1996).
Lan et al., "Isolation and Properties of a Human Pancreatic Adenocarcinoma-associated . . . " Cancer Res. 45:305-310 (1985).
Lanni et al., "p53-independent apoptosis induced by paclitaxel througho an indirect mechanism," Proc. Natl. Acad. Sci., 94:9679 (1997).
Lentz, et al., "Is the Acetylcholine Rectpor a Rabies Virus Receptor," Science 215:182 (1982).
Damen, E.W.P., et al., Biorganic & Medicinal Chemistry (2002) 10(1), pp. 71-77.
Hay, M.P., et al., Journal of Medicinal Chemistry (2003) 46(25), pp. 5533-5545.
Hay, M.P., et al., Journal of the Chemical Society-Perkin Transactions 1 (1999 (19), pp. 2759-2770.
Daniels, T.R., et al., Clinical Immunology (2006) 121(2), pp. 144-176.
Smith, M.W., and m. Gumbleton, Journal of Drug Targeting (2006) 14(4), pp. 191-214.
Koch, 1990, Angew. Chem. Int. Ed. Engl., 29:183-5.
Tomalia, et al., Chem. Int. Ed. Engl. 29:5305 (1990).
Yin, et al., J. Am. Chem. Soc., 120:2678 (1998).
Carelli, V., et al., Bioorganic & Medicinal Chemistry Letters (2003) 13(21), pp. 3765-3769.
Christrup, L.L., et al., International Journal of Pharmaceutics (1997). 154(2): pp. 157-165.
Drustrup, J., et al., International Journal of Pharmaceutics (1991), 71(1-2), pp. 105-116.
Groth, L., et al., International Journal of Pharmaceutics (1997) 154(2), pp. 149-155.
Mignat, C., et al., Journal of Pharmaceutical Sciences (1996) 85(7), pp. 690-694.
Hay, M.P., W.R. Wilson and W.A. Denny, Tetrahedron (2000) 56(4):, pp. 645-657.
de Groot, F.M.H., E.W.P. Damen, and H.W. Scheeren, Curr. Med. Chem.—Anti-Cancer Agents (2001) 8, pp. 1093-1122.
Dubowchik, G.M., and M.A. Walker, Pharmacology & Therapeutics (1999) 83, pp. 67-123.
Papot, S., et al., 2002, "Design of selectively activated anticancer prodrugs: elimination and cyclization strategies.", Curr Med Chem Anticancer Agents.; 2(2):155-85.
De Groot, F.M.H., et al., J. Org. Chem., 2001. 66, pp. 8815-8830.
Greenwald, R.B., et al., J. Med. Chem. (1999). 42: pp. 3657-3667.
Greenwald, R.B., et al., Bioconjugate Chem. (2003) 14, pp. 395-403.
Zhang, Z., et al., Pharmaceutical Research (2005) 22, pp. 381-389.
Antczak, C., et al., Bioorg. & Med. Chem (2001), 9: pp. 2843-2848.
Pohl, T., and H. Waldmann, J. Am. Chem. Soc. (1997), 119, pp. 6702-6710.
Sauerbrei, B., V. Jungmann, and H. Waldmann, Angew. Chem. Int. Ed. (1998), 37: pp. 1143-1146.
Leung, L.Y. and T.A. Baillie, J. Med. Chem. (1986), 29, pp. 2396-2399.
Woolf, T., et al., J. Org. Chem. (1984) 49. pp. 3305-3310.
Nudelman, A., R.J. McCaully and S.C. Bell, J. Pharm. Sci. (1974) 63, pp. 1880-1885.
Esfand, R. and D.A. Tomalila, Drug Discovery Today (2001). 6, pp. 427-436.
Jansen, J.F.G.A., E.M.M. de Brabander van den Berg and E.W. Maijer, Science (1994). 266, pp. 1226-1229.
Kolhe, P., et al., International Journal of Pharmaceutics (2003), 259, pp. 143-160.
Man, N., et al., European Journal of Medicinal Chemistry (2006), 41, pp. 670-674.
Morgan, M.T., et al., J. Am. Chem., Soc. (2003), 125(50): pp. 15485-15489.
Papagiannaros, A., et al., International Journal of Pharmaceutics (2005), 302, pp. 29-38.
Patri, A.K., J.F. Kukowska-Latallo, and J.R. Baker, Advanced Drug Delivery Reviews (2005) 57(15), pp. 2203-2214.
Patri, A.K., I.J Majoros and J.R. Baker Jr., Current Opinion in Chemical Biology (2002) 6, pp. 466-471.
Qiu, L.Y., and Y.H. Bae, Pharmaceutical Research (2006) 23, p. 1-30.
Schcharbin, D. and B.M., Biochmica et Biophysica Acta (2006) 1760, pp. 1021-1026.
Shi, X., et al., Electrophoresis (2006) 27(9), pp. 1758-1767.

(56) References Cited

OTHER PUBLICATIONS

Islam, M.T., I.J., Majoros and J.R. Baker, Journal of Chromatography B-Analytical Technologies in the Biomedical and Life Sciences (2005) 822(1-2): p. 21-26.
Islam, MT., et al., Analytical Chemistry (2005) 77(7): p. 2063-2070.
Shi, X., et al., Polymer (2005) 46: p. 3022-3034.
Shi, X., et al. Colloids Surf., A., (2006), 272, pp. 139-150.
Shi, X., I.J, Majoros and J.R. Baker, Jr., Mol. Pharm (2005), 2, pp. 278-294.
Shi, X.Y., et al., Electrophoresis (2005) 26(15), pp. 2949-2959.
Shi, X.Y., et al., Analysis (2006) 131(7): p. 842-848.
Shi, X.Y., et al. Analysis (2006) 131(3), pp. 374-381.
Shi, X.Y., et al. Electrophoresis (2005) 26(15): pp. 2960-2967.
Kuracka, L., et al., Clinical Chemistry (1996) 42(5), pp. 756-760.
Orlovic, D., et al., Chromatographia (2000) 52(11/12), pp. 732-734.
Svensson, J., et al., Journal of Chromatography B: Biomedical Sciences and Applications (1982), 230(2), pp. 427-432.
Wang, et al., "Synthesis and Application of Carbohydrate-Containing Polymers", Chem. Mater. (2002) 14, pp. 3232-3244.
Sottosanti, "Calcium Sulfate: A Biodegradable and Biocompatible Barrier for Guided Tissue Regeneration," Compendium 13(3):226-8, 230, 232-4 (1992).
Springer et al., "Blood Group Tn-Active Macromolecules from Human . . . " Carbohydr. Res. 178:271-292 (1988).
Stoddart, "Gene Delivery with Dendrimers", Chemical Biology 2006.
Talanian et al., "Substrate Specificities of Caspase Family Proteases," J. Biol. Chem., 272:9677 (1997).
Tang et al., "In Vivo Gene Delivery by Degraded Polyamidoamine Dendrimers," Biocong Chem 7:703 (1996).
Tjandra et al., "Application of mammary serum antigen assay in the management of breast cancer: a preliminary report," Br. J. Surg. 75:811-817 (1988).
Tomalia et al., "Starburst Dendrimers: Molecular-Level Control of Size, Shape, Surface chemistry, Topology, and Flexibility from Atoms to Macroscopic Matter," Chem. Int. Ed. Engl., 29:138-175(1990).
Tomalia et al., "Comb-Burst Dendrimer Topology. New Macromolecular Architecture Derived from Dendritic Grating,"Macromolecule 24:1435-1438 (1999).
Tomalia, "Starburst/Cascade Dendrimers: Fundamental Building Blocks for a New Nanoscopic Chemistry Set," Advanced Materials 6:529 (1994).
Tortora et al., "Synergistic Inhibition of Growth and Induction of Apoptosis by 8-Chloro-cAMP and Paclitaxel or Cisplatin in Human Cancer Cells," Cancer Research 57:5107 (1997).
Trainer, et al., "Gene delivery to the epidermis," Human Mol. Gen 6:1761 (1997).
Tuerk et al., "In vitro evolution of functional nucleic acids: high-affinity FNA ligands of HIV-1 proteins," Gene 137 (1):33-9 (1993).
Uppuluri et al., Tecto(Dendrimer) Core-Shell Molecules: . . . PMSE 80:55 (1999).
Urdea and Horn, "Dendrimer Development," Science 261:534 (1993).
Van Hest et al., "Polystyrene-Dendrimer Amphiphilic Block Copolymers with a Generation-Dependent Aggregation," Science 268:1592-1595 (1995).
Vasey et al., "Phase I Clinicial and Pharmacokinetic Study of PK1 . . . ", Clin. Cancer Res. 5:83 (1999).
Wagner, "Effects of membrane-active agents in gene delivery," Journal of controlled Release 53:155-158 (1998).
Webber et al., "Characterisation of soluble, salt-loaded, degradable PLGA films and their release of tetracycline," J. Biomed Mater Res 41:18 (1998).
White, et al., "Viral Recptors of the Immunoglobulin Superfamily," Cell 56:725 (1989).
Wiener et al., "Dendrimer-Based Metal Chelates: A New Class of Magnetic Resonance Imaging Contrast Agents," Magn Reson. Med. 31:1 (1994).
Wiener et al., "Targeting Dendrimer-Chelates to Tumors and Tumor Cells Expressing the High-Affinity Folate Receptor," Invest. Radiol. 32:748 (1997).
Wies, et al., "Structure of the influenza virus haemagglutinin complexed with its recptor, sialic acid," Nature 333:426 (1988).
Wilbur et al., "Biotin Reagents for Antibody Pretargeting . . . " Bioconjugate Chem., 9:813 (1998).
Winter, "Formation of the Scab and the Rate of Epithelization of Superficial Wounds in the Skin of the Young Domestic Pig," Nature 193:293 (1962).
Wong et al., "Accuracy and Precision of In Vitro Volumetric Measurements by Three-Dimensional Sonography," Ivest. Rad.31:26 (1996).
Wu et al., "Metal-Chelate-Dendrimer-Antibody Constructs for Use in Radioimmunotherapy and Imaging," Bioorg. Med. Chem. Lett., 4:449 (1994).
Wyrick et al., "Entry of Genital *Chlamydia trachomatis* into Polarized Human Epithelial Cells," Infect. Imm. 57:2378 (1989).
Ye, et al., "Targeted gene correction: a new strategy for molecular medicine" Mol. Med. Today 4:431 (1998).
Yew et al., "Optimization of Plasmid Vectors for High-Level Expression in Lung Epithelial Cells," Human Gene Ther. 8:575 (1997).
Yin et al., "Architectural Copolymers: Rod-Shaped, Cylindrical Dendrimers," J. Am. Chem. Soc., 120:2678 (1998).
Yu, et al., "Overexpression of ErbB2 blocks Taxol-Induced Apoptosis by Upregulation of p21(cip1), which Inhibits p34 (Cdc2) Kinase," Molecular Cell, 2:581 (1998).
Zaffaroni et al., "Induction of apoptosis by taxol and cisplatin and effect on cell cycle-related proteins in cisplatin-sensitive and resistance human ovarian cancer cells," Brit. J. Cancer 77:1378 (1998).
Zhuo et al. 1999, In vitro release of 5-fluorouracil with cyclic core dendritic polymer, J. of Controlled Release 57:249-257.
Zimmerman et al., "Self-Assembling Dendrimers," Science 271:1095-1098 (1996).
Suzawa, et al., "Synthesis of a Novel Duocarmycin Derivative DU-257 . . . ", Bioorganic & Medicinal Chemistry 8 (2000) 2175-2184.
Yang, Cancer Research, 1997, vol. 53, pp. 4333-4339.
Mojoros et al., Macromolecules, 2003, vol. 36, pp. 5526-5529.
Wu et al., Anti-Cancer Agents in Medicinal Chemistry, Mar. 2006, vol. 6, pp. 167-184.
International Search Report dated Jan. 5, 2010, PCT/US2009/036992, filed Mar. 12, 2009.
Jesse B. Wolinsky and Mark W. Grinstaff, "Therapeutic and diagnostic application of dendrimers for cancer treatment," Advanced Drug Delivery Reviews, Mar. 4, 2008, vol. 60, pp. 1037-1055.
Ulrik Boas and Peter M. H. Heegaard, "Dendrimers in drug research," Chemical Society Review, 2004, vol. 33, pp. 43-63.
Istvan J. Majoros, et al., "Poly(amidoamine) dendrimer-based multifunctional engineered nanodevice for cancer therapy," Journal of Medicinal Chemistry, 2005, vol. 48, pp. 5892-5899.
Tooru Ooya, Jaehwei Lee and Kinam Park, "Hydrotropic dendrimers of generations 4 and 5: Synthesis, characterization and hydrotropic solubilization of paclitaxel," Bioconjugate Chemistry, 2004, vol. 15, pp. 1221-1229.
Anil K. Patri, et al., "Synthesis and in vitro testing of J591 antibody-dendrimer conjugates for targeted prostage cancer therapy," Bioconjugate Chemistry 2004, vol. 15, pp. 1174-1181.
Thomas, Thommey, et al., "Detection and Analysis of Tumor Fluorescence Using a Two-Photon Optical Fiber Probe," Biophysical Journal, vol. 86, Jun. 2004, pp. 3959-3965.
Kolb, et al. (2001) Angewandte Chemie Intl. Ed. 40:2004-2011.
Evans (2007) Australian J. Chem. 60:384-395.
Carlmark, et al. (2009) Chem. Soc. Rev. 38:352-362.
Allen, T.M., Nature Reviews Cancer (2002) 2, (1), pp. 750-763.
Peer, D., et al., Nature Nanotechnology (2007), 2, pp. 751-760.
Majithia V, et al. Am. J. Med. (2007) 120 (11): 936-9.
Eichman et al. (2000) Pharm. Sci. Technolo. Today 3:232-245.
Lou et al. (2002) Macromol. 35:3456-3462.
Kobayashi et al. (2003) Bioconj. Chem. 14:388-394.
Wangler, C., et al., "Antibody-dendrimer conjugates: the number, not the size of the dendrimers, determines the immunoreactivity," Bioconjug Chem., Apr. 2008, vol. 19(4), pp. 813-820.

(56) References Cited

OTHER PUBLICATIONS

Dirks, A. (Ton) J., et al., "Monitoring Protein--Polymer Conugation by a Fluorogenic (Cu(I)—Catalyzed Azide——Alkyne 1,3-Dipolar Cycloaddition," Bioconjugate Chemistry, vol. 20, No. 6, pp. 1129-1138 (Jun. 2009).
Lalwani, Sanjiv, et al., "Mimicking PAMAM Dendrimers with Amphoteric, Hybrid Triazine Dendrimers: A Comparison of Dispersity and Stability," Macromolecules, vol. 42, No. 17, pp. 6723-6732 (Aug. 12, 2009).
Rheumatoid arthiritis, Merck Manual Home Ed. Avaialble at http://wwww.merckmanuals.com/home/print/sec05/ch066/ch066b.html (printed Apr. 19, 2011).
CN Office Action mailed Aug. 14, 2013, CN Patent Application No. 201080059383.
Hong, S., et al., Chemistry & Biology (2007), 14 (1), pp. 105-113.
Mammen, M., et al., Angewandte Chemie-International Edition (1998), 37 (20), pp. 2755-2794.
Hong, S.P., et al., Bioconjugate Chmistry (2004) 15, (4), pp. 774-782.
Svenson, S., et al., Advanced Drug Delivery Reviews (2005), 57 (15), pp. 2106-2129.
Hong, S.P., et al., Bioconjugate Chmistry (2006) 17(3), pp. 728-734.
Leroueil, P.R., Acc. Chem. Res. 40(5) (2007) pp. 335-342.
Thomas, T.P., et al., Biomacromoledules (2004) 5, (6) pp. 2269-2274.
Shukla, R., et al., Bioconjugate Chemistry (2006), 17 (5), pp. 1109-1115.
Wu, G., et al., Molecular Cancer Therapeutics (2006) 5(1) pp. 52-59.
Wu, G., et al., Bioconjugate Chemistry (2004) 15(1), pp. 185-194.
Backer, M.V., et al., Molecular Cancer Therapeutics (2005) 4(9), pp. 1423-1429.
Shukla, R., et al., Chemical Communications (2005) 46, pp. 5739-5741.
Sheng, K.C., et al., European Journal of Immunology (2008), 38, pp. 424-436.
Baek, M.G., et al., Bioorganic & Medicinal Chemistry (2002) 10 (1) pp. 11-17.
Taite, L.J, et al., Journal of Biomaterials Science-Polymer Edition (2006) 17(10), pp. 1159-1172.
Kono, K., et al., Bioconjugate Chemistry (1999) 10(6), pp. 1115-1121.
Shukla, S., et al., Bioconjugate Chemistry (2003) 14(1), pp. 158-167.
Thomas, t.p., et al., Journal of Medicinal Chemistry (2005), 48 (11), pp. 3729-3735.
Myc, A., et al., Anti-Cancer Drugs (2008) 19, pp. 143-149.
Majoros, I.J., et al., Journal of Medicinal Chmistry (2005) 48 (19) pp. 5892-5899.
Kukowska-Latallo, J.F., et al., Cancer Research (2005) 65(12) pp. 5317-5324.
Myc, A., et al., Biomacromolecules (2007) 8, pp. 2986-2989.
Myc, A., et al., Biomacromolcules (2007) 8 (1), pp. 13-18.
Landmark, K.J., et al., ACS Nano (2008) 2 (4), pp. 773-783.
Mullen, D.G., Bioconjug. Chem. 19(9) (2008) pp. 1748-1752.
Choi, Y., Nanostructured Supramolecular Arrays Based on Dendrimers Using DNA: Desgin, Synthesis and Biological Evaluation. Biomed. Eng. (NY), vol. Ph.D., Dissertation, University of Michigan, Ann Arbor, MI (2005), p. 191.
Lee, J.W., Macromolecules 39(6) (2006), pp. 2418-2422.
Wu, P., Chem. Commun. (46) (2005), pp. 5775-5777.
Goyal, P., Chem. Eur. J. 13 (2007), pp. 8801-8810.
Yoon, K., Org. Letter 9(11) (2007), pp. 2051-2054.
Choi, Y.S., et al., Nano Letter 4(3) (2004), pp. 391-397.
Demattie, C.R., et al., Nano Letters 4(5) (2004), pp. 771-777.
Choi, Y., et al., Chem. Biol. 12(1) (2005), pp. 35-43.
Rostovtsev, V.V., et al., Angewandte Chemie-Inernational Edition (2002) 41 (14), p. 2596.
Wu, P., et al., Angewandte Chemie-International Edition (2004) 43 (30) pp. 3928-3932.
Wu, P., et al., Aldrichimica Acta 40(1) (2007), pp. 7-17.
Lee, J.W., et al., Bioconjugate Chemistry (2007) 18(2), pp. 579-584.
Lee, J.W., et al., Journal of Polymer Science Part a-Pollymer Chemistry (2008) 46, pp. 1083-1097.
Lee, J.W., et al., Tetrahedron (2006) 62(5), pp. 894-900.
Hoffman, R.E., Magn. Reson. Chem. (2006), 44, pp. 606-616.
De Groot, Franciscus, M.H., "Cascade-Release Dendrimers", Liberate All End Groups Upon a Single Triggering Event in the Dendritic Core, Angew. Chem. Int. Ed. (2003), vol. 42, pp. 4490-4494.
Lee, Cameron C., et al., "Designing Dendrimers for Biological Applications," Nature Biotechnology, Dec. 2005, vol. 23, No. 12, pp. 1517-1526.
Bloodworth, D., Phys. Med. Rehabil Clin. N. Am., (2006) 17(2), pp. 355-79.
Liu, J.K., et al., Neurobiology of Disease (2005) 1993), pp. 407-418.
Beall, H.D., et al., Journal of Medicinal Chemistry (1998) 41(24), pp. 4755-4766.
Ferrer, S., D.P. Naughton and M.D. Threadgill, Tetrahedron (2003) 59(19), pp. 3445-3454.
Naylor, M.A., et al., Journal of Medicinal Chemistry (1997) 40(15), pp. 2335-2346.
Zhang, Z., et al., Organic & Biomolecular Chemistry (2005) 3(10), pp. 1905-1910.
Phillips, R.M., et al., Journal of Medicinal Chemistry (1999) 42(20), pp. 4071-4080.
Svensson, J.-O, Journal of Chromatography B., Biomedical Sciences and Applications ()1986) 375, pp. 174-178.
Tebbett, I.R. Chromatographia 23(5), pp. 377-378, 1987.
Stamford, J.A., Journal of Neuroscience Methods, (1990), 34(1-3), pp. 67-72.
Toner, C.C., and J.A. Stamford, Journal of Neuroscience Methods (1996) 67(2), pp. 133-140.
Toner, C.D. and J.A. Stamford, Neuroscience (1997), 81(4), pp. 999-1007.
Kimiskidis, V., et al., 2007, "Development and validation of a high performance liquid chromatographic method for the determination of oxcarbazepine and its main metabolites in human plasma and cerebrospinal fluid and its application to pharmacokinetic study", J Pharm Biomed Anal.; 43(2):763-8.
Achilli, G., et al., Journal of Chromatography, A. (1996) 729(1-2), pp. 273-277.
Horner, K.A., et al., Brain Research (2004) 1028(2): pp. 121-32.
Childers, S.R. and S.R. Childers, Life Sciences (1991) 48(21): pp. 1991-2003.
Adams, J.D., Jr., et al. Biomedical Mass Spectometry (1981) 8(11): pp. 527-38.
Millhorn et al, 1996, "Regulation of ionic conductances and gene expression by hypoxia in an oxygen sensitive cell line.", Adv Exp Med Biol. 410:135-42.
Cai, Y.C., et al., "Molecular Pharmacology," (1997) 51(4), pp. 583-7.
Franklin, R,B., et al., BMC Biochemistry (2006) 7: p. 10.
Kukanich, B., et al., Therapeutic Drug Monitoring (2005) 27(3), pp. 389-92.
Cucullo, L., et al., Current Opinion in Drug Discovery & Development (2005) 8(1), pp. 88-99.
Nambiar, M.P., et al., Toxicology and Applied Pharmacology (2007) 219(2-3), pp. 142-150.
Shih, T.M., T.C. Rowland and J.H. McDonough, Journal of Pharmacology and Experimental Therapeutics (2007) 320 (1), pp. 154-161.
Schulte, H., A. Sollevi and M. Segeradahl, Pain, (2005) 116(3), pp. 366-374.
Loetsch, J., et al., Clinical Pharmacology and Therapeutics (1996) 60(3): pp. 316-325.
Hill, H.F., et al., Pain (1990) 43(1), pp. 57-79.
Worek, F., et al., Toxicology (2008). 244: pp. 35-41.

* cited by examiner

Divergent            Convergent

FIGURE 2

| | Branch growth<br>Pre-made $AB_n$ (n=2,3) | Re-generation of reactive functionality | |
|---|---|---|---|
| Fréchet | A HO–⟨⟩–OH B, OH B; Br–◯ C | OH → Br<br>A → C | Convergent |
| Parquette | A Cl–⟨pyridine⟩(C(O)Cl B)(C(O)Cl B); H₂N–◯ C | Cl → NH₂<br>A → C | Convergent |
| Newkome | ◯–Br C; A Na–C(CO₂Et B)₃ | CO₂Et → CH₂Br<br>B → C | Divergent |
| | Branch growth<br>Michael addition | | |
| Fögtle (PPI) | ◯–NH₂ + ⟵CN; ◯–N(CH₂CH₂CN)₂ | CN → CH₂NH₂ | Divergent |
| Tomalia (PAMAM) | ◯–NH₂ + ⟵C(O)OMe; ◯–N(CH₂CH₂C(O)OMe)₂ | –C(O)OMe → –C(O)NH–CH₂CH₂NH₂ | Divergent |

FIGURE 19
A)
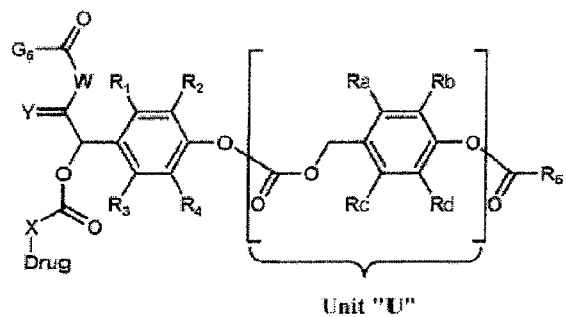
B)
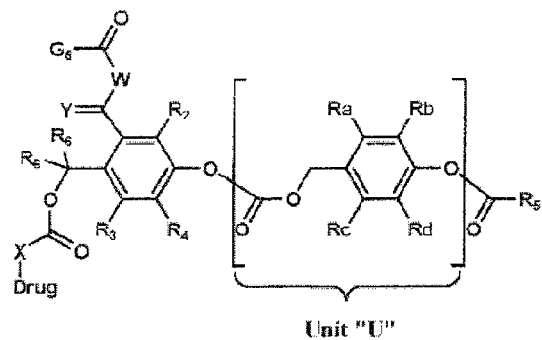
C)
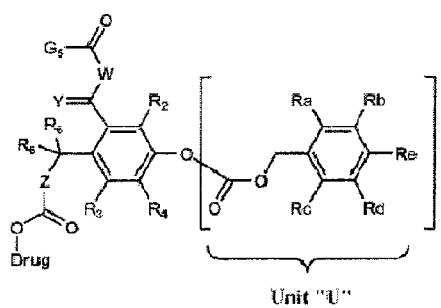

FIGURE 23
A)
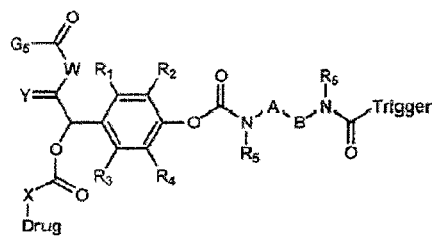
B)
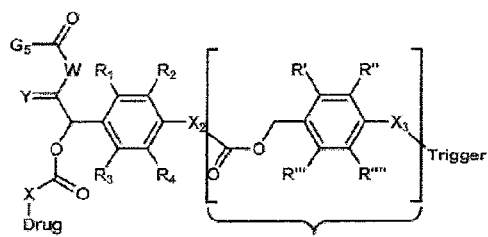
C)
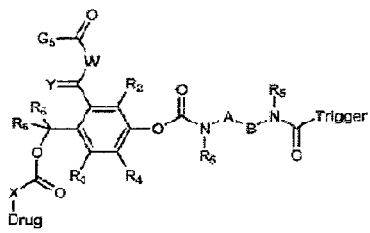
D)
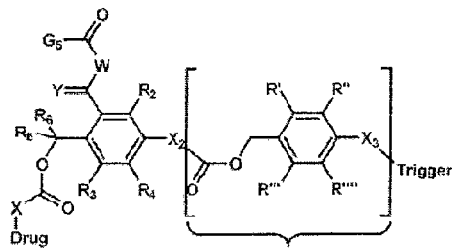

FIGURE 31
A
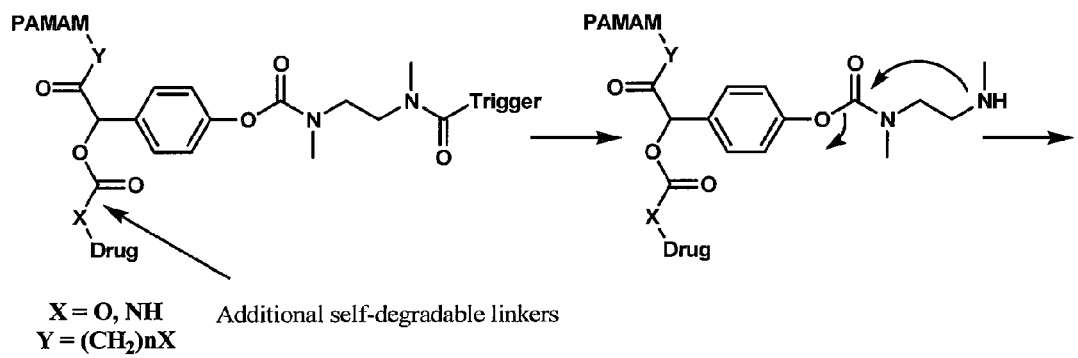
X = O, NH   Additional self-degradable linkers
Y = (CH$_2$)nX
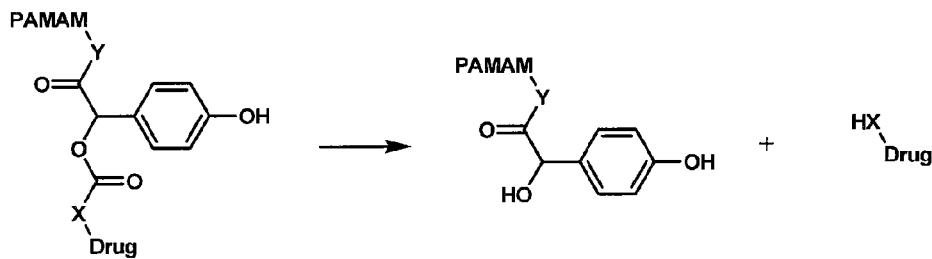
B
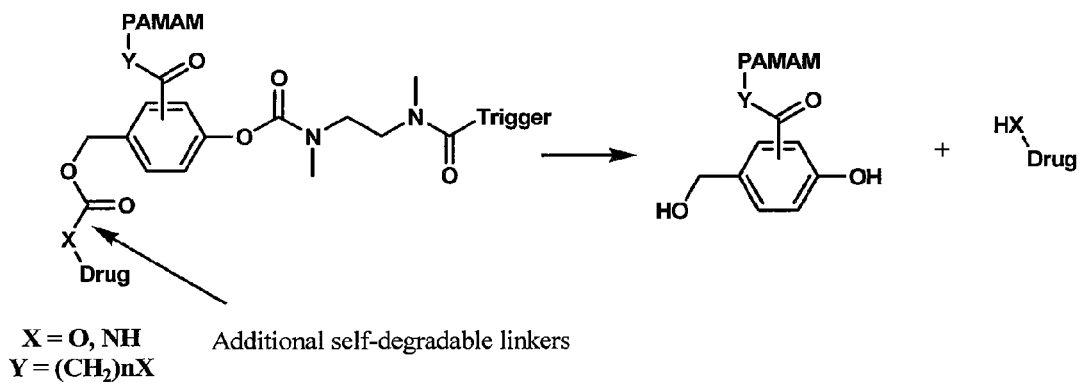
X = O, NH   Additional self-degradable linkers
Y = (CH$_2$)nX FIGURE 32
Simple esters
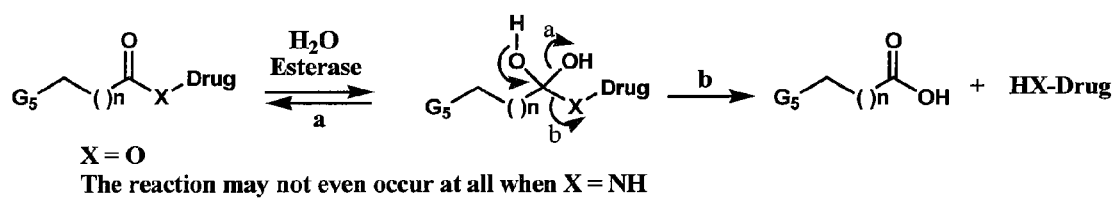
X = O
The reaction may not even occur at all when X = NH
Esters with an 1,6-elimination spacer will drive the hydrolysis to completion:
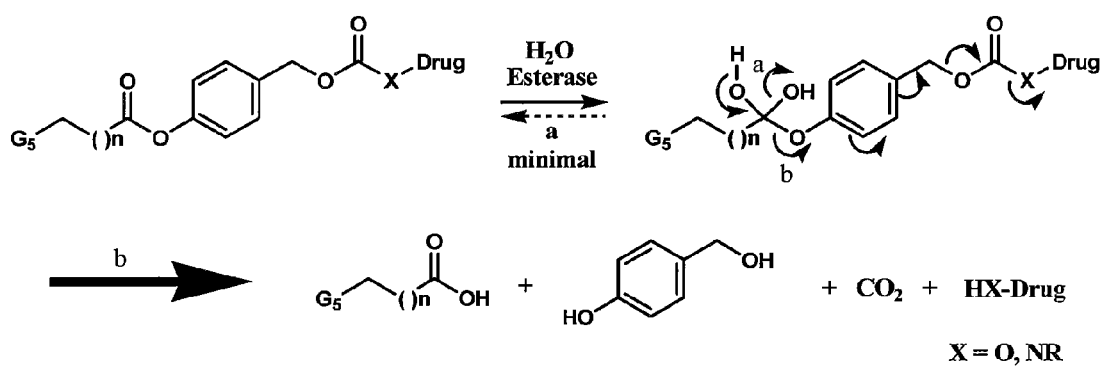
X = O, NR

DENDRIMER COMPOSITIONS AND METHODS OF SYNTHESIS

CROSS-REFERENCE TO RELATED APPLICATION

This application is a U.S. 371 National Phase Entry of pending International Patent Application No. PCT/US2010/051835, International Filing Date Oct. 7, 2010, which claims priority to U.S. Provisional Patent Application No. 61/251,244, filed Oct. 13, 2009, the contents of which are herein incorporated by reference in their entireties.

STATEMENT REGARDING FEDERALLY SPONSORED RESEARCH OR DEVELOPMENT

This invention was made with government support under Contract No. W911NF-07-1-0437 awarded by the Army Research Office. The government has certain rights in the invention.

FIELD OF THE INVENTION

The present invention relates to novel dendrimer compounds and methods of synthesizing the same. In particular, the present invention is directed to novel polyamidoamine (PAMAM) dendrimers, novel dendrimer branching units, methods for synthesizing such novel PAMAM dendrimers and functionalized dendrimers, as well as systems and methods utilizing the dendrimers (e.g., in diagnostic and/or therapeutic settings (e.g., for the delivery of therapeutics, imaging, and/or targeting agents (e.g., in disease diagnosis and/or therapy, etc.))).

BACKGROUND OF THE INVENTION

Dendritic molecules are repeatedly branched species that are characterised by structural perfection. This is based on the evaluation of both symmetry and polydispersity. The field of dendritic molecules can roughly be divided into low-molecular weight and high-molecular weight species. The first category includes dendrimers and dendrons, and the second includes dendronised polymers, hyperbranched polymers and brush-polymers (called also bottle-brushes).

The first dendrimers were synthesised divergently by Vögtle in 1978 (see, e.g., Buhleier, et al., Synthesis 1978: 155-158; herein incorporated by reference in its entirety), by Denkewalter as polylysine dendrimers in 1981 (see, e.g., U.S. Pat. No. 4,289,872 and U.S. Pat. No. 4,410,688; each herein incorporated by reference in their entireties), by Tomalia in 1983 (see, e.g., U.S. Pat. No. 4,507,466) (see, e.g., Tomalia, et al., Polymer Journal 1985 17:117; each herein incorporated by reference in their entireties), and by Newkome in 1985 (see, e.g., Newkome, et al., 1985 J. Org. Chem. 50: 2003; herein incorporated by reference in its entirety). In 1990 a convergent synthesis method was introduced by Fréchet (see, e.g., Hawker, et al., 1990, J. Am. Chem. Soc. 112: 7638; herein incorporated by reference in its entirety). Dendrimers then experienced an explosion of scientific interest because of their unique molecular architecture. This resulted in more than 5,000 scientific papers and patents published by the end of 2005.

Polyamidoamine (PAMAM) dendrimers are a common class of dendrimers suitable for many materials science and biotechnology applications. PAMAM dendrimers consist of alkyl-diamine core and tertiary amine branches. They are available in generations G 0-10 with 5 different core types and 10 functional surface groups. Methods for synthesizing PAMAM dendrimers, however, have limitations. For example intramolecular dendrimer polymerization, intermolecular looping, and dendrimers having missing branches are common problems associated with classical synthesis methods. Accordingly, there exists a need for improved methods for synthesizing PAMAM dendrimers.

SUMMARY

The present invention relates to novel dendrimer compounds and methods of synthesizing the same. In particular, the present invention is directed to novel polyamidoamine (PAMAM) dendrimers, novel dendrimer branching units, methods for synthesizing such novel PAMAM dendrimers and functionalized dendrimers, as well as systems and methods utilizing the dendrimers (e.g., in diagnostic and/or therapeutic settings (e.g., for the delivery of therapeutics, imaging, and/or targeting agents (e.g., in disease diagnosis and/or therapy, etc.).

Experiments conducted during the course of developing embodiments for the present invention demonstrated improved dendrimer compositions and methods of synthesis thereof. Specifically, it was discovered that convergent synthesis methods of generating dendrimers (e.g., PAMAM dendrimers; Baker-Huang PAMAM dendrimers) resulted in improved dendrimer compositions that lacked the common structural defects associated with classical dendrimers (e.g., Tomalia PAMAM dendrimers). Such structural defects include but are not limited to intramolecular dendrimer polymerization, intermolecular looping, and dendrimers having missing branches. Compositions related to the present invention (e.g., Baker-Huang PAMAM dendrimers) include additional structurally advantageous features including but not limited to central regions bearing functional groups (e.g., —OH and/or —NH functional groups) that find use for attachments of functional ligands (e.g., therapeutic agents, imaging agents, targeting agents, trigger agents) and/or which find use for drug delivery or drug encapsulation, and which are not present in classical (e.g., Tomalia) PAMAM dendrimers. Finally, experiments conducted during the course of developing the present invention demonstrated novel synthetic methods that result in products with improved structural uniformity and that therefore require fewer downstream processing steps as compared to classical (e.g., divergent) PAMAM synthesis methods.

In certain embodiments, the present invention provides compositions comprising novel PAMAM dendrimers (e.g., Baker-Huang dendrimers) conjugated with one or more ligands (e.g., functional groups (e.g., imaging agents, targeting agents, therapeutic agents, locking agents, etc.)). In some embodiments, conjugation of a ligand (e.g., functional group) with the dendrimer is accomplished with a linker and/or a trigger agent and/or a scaffold (see, e.g., PCT/US2010/050893; herein incorporated by reference in its entirety).

In some embodiments, the functional group(s) is attached (e.g., conjugated) with the dendrimer via a linker. The present invention is not limited to a particular type or kind of linker. In some embodiments, the linker comprises a spacer comprising between 1 and 8 straight or branched carbon chains. In some embodiments, the straight or branched carbon chains are unsubstituted. In some embodiments, the straight or branched carbon chains are substituted with alkyls.

In some embodiments, conjugation between a ligand and a functional group or between functional groups is accomplished through use of a 1,3-dipolar cycloaddition reaction ("click chemistry"). 'Click chemistry' involves, for example, the coupling of two different moieties (e.g., a therapeutic agent and a functional group) (e.g., a first functional group and a second functional group) via a 1,3-dipolar cycloaddition reaction between an alkyne moiety (or equivalent thereof) on the surface of the first moeity and an azide moiety (or equivalent thereof) (or any active end group such as, for example, a primary amine end group, a hydroxyl end group, a carboxylic acid end group, a thiol end group, etc.) on the second moiety. 'Click chemistry' is an attractive coupling method because, for example, it can be performed with a wide variety of solvent conditions including aqueous environments. For example, the stable triazole ring that results from coupling the alkyne with the azide is frequently achieved at quantitative yields and is considered to be biologically inert (see, e.g., Rostovtsev, V. V.; et al., Angewandte Chemie-International Edition 2002, 41, (14), 2596; Wu, P.; et al., Angewandte Chemie-International Edition 2004, 43, (30), 3928-3932; each herein incorporated by reference in their entireties).

The present invention is not limited to particular functional groups (e.g., for conjugation with dendrimers). Examples of functional groups include but are not limited to therapeutic agents, targeting agents, trigger agents, and imaging agents.

The present invention is not limited to particular type or kind of trigger agent. In some embodiments, the trigger agents are configured to delay release of a functional group (e.g., a therapeutic agent) from the PAMAM dendrimer (e.g., Baker-Huang dendrimer) (e.g., via an ester bond trigger agent). For example, in some embodiments, the trigger agents are configured to constitutively release a therapeutic agent from a PAMAM dendrimer (e.g., Baker-Huang dendrimer) (e.g., an amide bond, an ether bond). In some embodiments, the trigger agent is configured to facilitate a constitutive release of a functional group (e.g., a therapeutic agent, an imaging agent, a targeting agent) from the PAMAM dendrimer (e.g., Baker-Huang dendrimer). In some embodiments, the trigger agent is configured to release a functional group from the PAMAM dendrimer (e.g., Baker-Huang dendrimer) under conditions of acidosis. In some embodiments, the trigger agent is configured to release the functional group from the PAMAM dendrimer (e.g., Baker-Huang dendrimer) under conditions of hypoxia (e.g., indoquinones, nitroheterocyles, and nitroimidazoles). In some embodiments, the trigger agent is configured to release a functional group from the PAMAM dendrimer (e.g., Baker-Huang dendrimer) in the presence of a brain enzyme (e.g., the trigger agent is indolequinone and the brain enzyme is diaphorase). Examples of trigger agents include, but are not limited to, an ester bond, an amide bond, an ether bond, an indoquinone, a nitroheterocyle, and a nitroimidazole.

The present invention is not limited to a particular type or kind of targeting agent. In some embodiments, the targeting agent is configured to permit the composition to cross the blood brain barrier (e.g., transferrin). In some embodiments, the targeting agent is configured to permit the composition to bind with a neuron within the central nervous system (e.g., the targeting agent is a synthetic tetanus toxin fragment (e.g., an amino acid peptide fragment (e.g., HLNILSTLWKYR (SEQ ID NO: 2))). In some embodiments, the targeting agent is configured to target the composition to cancer cells. In some embodiments, the targeting agent comprises FA. In some embodiments, the targeting agent binds a receptor selected from the group consisting of CFTR, EGFR, estrogen receptor, FGR2, folate receptor, IL-2 receptor, and VEGFR. In some embodiments, the targeting agent comprises an antibody that binds to a polypeptide selected from the group consisting of p53, Muc1, a mutated version of p53 that is present in breast cancer, HER-2, T and Tn haptens in glycoproteins of human breast carcinoma, and MSA breast carcinoma glycoprotein. In some embodiments, the targeting agent comprises an antibody selected from the group consisting of human carcinoma antigen, TP1 and TP3 antigens from osteocarcinoma cells, Thomsen-Friedenreich (TF) antigen from adenocarcinoma cells, KC-4 antigen from human prostrate adenocarcinoma, human colorectal cancer antigen, CA125 antigen from cystadenocarcinoma, DF3 antigen from human breast carcinoma, and p97 antigen of human melanoma, carcinoma or orosomucoid-related antigen.

The present invention is not limited to a particular type or kind of locking agent. In some embodiments, the locking agent, upon activation, prevents transfer of the composition across the blood brain barrier. In some embodiments, the locking agent is a pyridinium molecule which is activated by enzymes specific to the central nervous system. In some embodiments, the locking agent is a re-dox system. In some embodiments, the re-dox system is the 1,4-dihydrotrigonelline ↔ trigonelline (coffearine) re-dox system, wherein conversion of lipophilic 1,4-dihydro form (L) in vivo to the hydrophilic quaternary form ($L^+$) by oxidation prevents the composition from diffusing across the blood brain barrier.

The present invention is not limited to a particular type or kind of therapeutic agent. Examples of therapeutic agents include, but are not limited to, a chemotherapeutic agent, an anti-oncogenic agent, an anti-angiogenic agent, a tumor suppressor agent, an anti-microbial agent, an expression construct comprising a nucleic acid encoding a therapeutic protein, a pain relief agent, a pain relief agent antagonist, anesthetic drugs, antipsychotic drugs, hypnotic drugs, sedative drugs, muscle relaxant drugs, an agent designed to treat an inflammatory disorder, an agent designed to treat an autoimmune disorder, an agent designed to treat inflammatory bowel disease, and an agent designed to treat inflammatory pelvic disease. In some embodiments, the agent designed to treat an inflammatory disorder includes, but is not limited to, an antirheumatic drug, a biologicals agent, a nonsteroidal anti-inflammatory drug, an analgesic, an immunomodulator, a glucocorticoid, a TNF-α inhibitor, an IL-1 inhibitor, and a metalloprotease inhibitor. In some embodiments, the antirheumatic drug includes, but is not limited to, leflunomide, methotrexate, sulfasalazine, and hydroxychloroquine. Examples of biologicals agents include, but are not limited to, rituximab, infliximab, etanercept, adalimumab, and golimumab. In some embodiments, the nonsteroidal anti-inflammatory drug includes, but is not limited to, ibuprofen, celecoxib, ketoprofen, naproxen, piroxicam, and diclofenac. In some embodiments, the analgesic includes, but is not limited to, acetaminophen, and tramadol. In some embodiments, the immunomodulator includes but is not limited to anakinra, and abatacept. In some embodiments, the glucocorticoid includes, but is not limited to, prednisone, and methylprednisone. In some embodiments, the TNF-α inhibitor includes but is not limited to adalimumab, certolizumab pegol, etanercept, golimumab, and infliximab. In some embodiments, the autoimmune disorder and/or inflammatory disorder includes, but is not limited to, arthritis, psoriasis, lupus erythematosus, Crohn's disease, and sarcoidosis. In some embodiments, examples of arthritis include, but are not limited to, osteoarthritis, rheumatoid arthritis, septic arthritis, gout and pseudo-gout, juvenile idiopathic arthritis, psoriatic arthritis, Still's disease, and ankylosing spondylitis.

In some embodiments, the PAMAM dendrimer (e.g., Baker-Huang dendrimer) composition comprises a plurality of therapeutic agents (e.g., 2, 3, 4, 5, 10, 15, 50, 100, at any desired ratio).

The present invention is not limited to a particular type or kind of imaging agent. Examples of imaging agents include, but are not limited to, fluorescein isothiocyanate (FITC), 6-TAMARA, acridine orange, and cis-parinaric acid.

In some embodiments, the present invention provides methods for treating a disorder or condition (e.g., arthritis, cancer) comprising administering to a subject (e.g., a human patient) a novel PAMAM dendrimer (e.g., Baker-Huang dendrimer) conjugated with functional groups configured for treating the disorder or condition.

In certain embodiments, the present invention provides compositions comprising a compound having repeating [(tertiary amine-amide)n-(tertiary amine-amide-amide-tertiary amine)-(amide-tertiary amine)n]dendrimer structure wherein n is limitless (e.g., 1, 2, 3, 4, 5, 10, 25, 50, 75, 100, 1000, 10000, etc.). In some embodiments, the tertiary amines and amide components are independently separated by alkyl chains of any length (e.g., methyl, ethyl, propyl, butyl, pentyl, hexyl, heptyl, octyl, etc.). In some embodiments, the terminal tertiary amines are conjugated with functional ligands (e.g.,

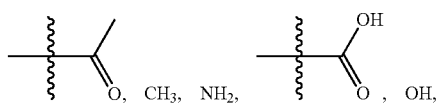

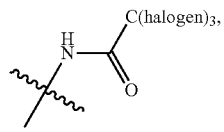

a targeting agent, a therapeutic agent, a pro-drug, an imaging agent, and a trigger agent).

In certain embodiments, the present invention provides compositions comprising a compound having the following formula:

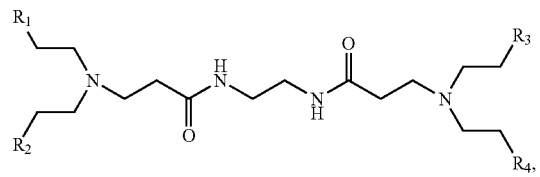

wherein R1, R2, R3, R4 are wherein R5 is a targeting agent, a therapeutic agent, a pro-drug, an imaging agent, a trigger agent (e.g., a lone trigger agent or a trigger agent conjugated with a functional group (e.g., a targeting agent, a therapeutic agent, a pro-drug, an imaging agent, a linker (e.g., a linker conjugated with a targeting agent, a therapeutic agent, a pro-drug, an imaging agent))), and a linker conjugated with a functional group (e.g., a targeting agent, a therapeutic agent, a pro-drug, an imaging agent, a trigger agent (e.g., a lone trigger agent or a trigger agent conjugated with a functional group (e.g., a targeting agent, a therapeutic agent, a pro-drug, an imaging agent, a linker (e.g., a linker conjugated with a targeting agent, a therapeutic agent, a pro-drug, an imaging agent))).

In some embodiments, the compound has the following formula:

The compositions are not limited to a particular manner of synthesis. In some embodiments, the composition is produced by a convergent synthesis reaction.

In some embodiments, the compositions further comprise nanomaterials (e.g., gold nanoparticles, iron oxide nanoparticles, polymers, silica, albumin, quantum dots, and carbon nanotubes).

In some embodiments, the compound is selected from the group consisting of

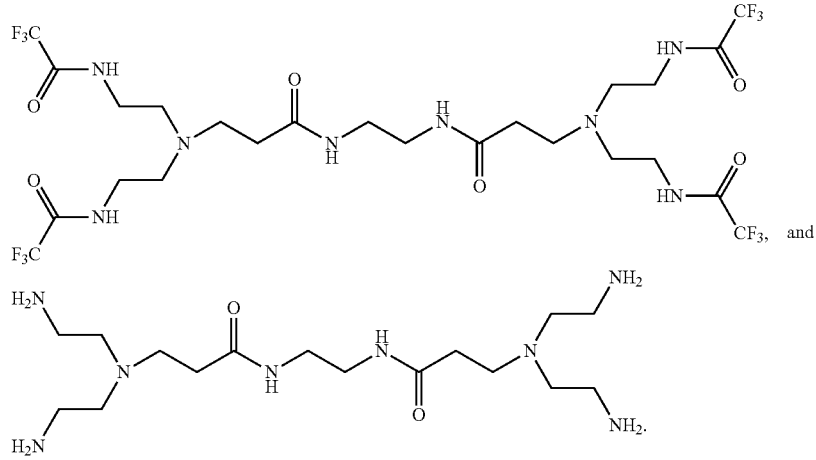

In certain embodiments, the present invention provides compositions comprising a compound having the following formula: $AB_2$, wherein A comprises a carboxylic acid, wherein B comprises a protected amine. In some embodiments, the compound has the following formula:

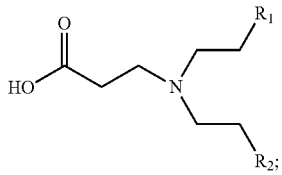

wherein R1 and R2 are independently selected from the group consisting of

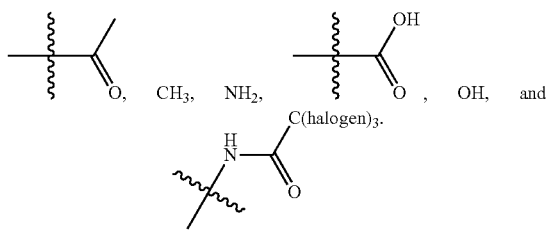

In certain embodiments, the present invention provides methods for synthesizing a composition comprising one or more dendrimer molecules, comprising a) providing two or more dendrimer branch unit agents, wherein the dendrimer branch unit agents have the following formula: $AB_2$, wherein A comprises a carboxylic acid, wherein B comprises a protected amine, and b) reacting the two or more dendrimer branch unit agents under conditions such that the two or more dendrimer branch unit agents assemble into a dendrimer molecule.

The methods are not limited to particular reaction conditions. In some embodiments, the reacting involves addition of EDA and/or TSTU (O—(N-succinimidyl)-1,1,3,3-tetramethyluronium tetrafluoroborate). In some embodiments, the reacting occurs in the presence of agents selected from the group consisting of MeCN and DIPEA.

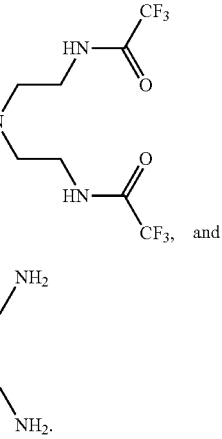

In some embodiments, the dendrimer branch unit agent has the following formula:

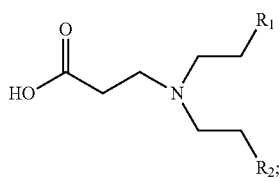

wherein R1 and R2 are independently selected from the group consisting of

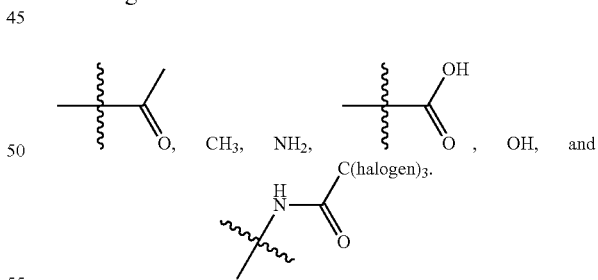

In some embodiments, the methods further comprise purification of the dendrimer molecule by crystallization with $CHCl_2$. In some embodiments, the methods further comprise treatment of the dendrimer molecule with $K_2CO_3$.

In some embodiments, the methods further comprise conjugating the dendrimer molecule with a functional ligand independently selected from the group consisting of $CH_3$, $NH_2$, OH, C(halogen)$_3$, targeting agent, a therapeutic agent, a pro-drug, an imaging agent, and a trigger agent. In some embodiments, the methods further comprise conjugating the dendrimer molecule with nanomaterials selected from the group consisting of gold nanoparticles, iron oxide nanoparticles, polymers, silica, albumin, quantum dots, and carbon nanotubes.

In certain embodiments, the present invention provides dendrimer molecules as generated with the methods of the present invention.

In certain embodiments, the present invention provides kits for generating dendrimer molecules. The present invention is not limited to particular ingredients for such kits. In some embodiments, the kits comprise two or more dendrimer branching unit agents having the following formula:

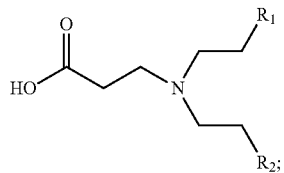

wherein R1 and R2 are independently selected from the group consisting of

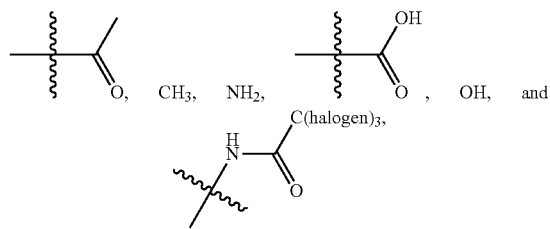

and one or more reaction agents (e.g., EDA, TSTU (O—(N-succinimidyl)-1,1,3,3-tetramethyluronium tetrafluoroborate), MeCN or DIPEA). In some embodiments, the kits further comprise instructions for generating dendrimer molecules with ingredients.

In certain embodiments, the present invention provides methods for treating a disorder (e.g., any type of cancer or cancer-related disorder (e.g., tumor, a neoplasm, a lymphoma, or a leukemia), a neoplastic disease, an inflammatory disorder, an autoimmune disorder) comprising administering to a subject suffering from the disorder a dendrimer generated with the methods of the present invention (e.g., Baker-Huang PAMAM dendrimer) (e.g., a Baker-Huang PAMAM dendrimer conjugated with functional groups (e.g., one or more therapeutic agents). In some embodiments, the autoimmune disorder and/or inflammatory disorder includes, but is not limited to, arthritis, psoriasis, lupus erythematosus, Crohn's disease, and sarcoidosis. In some embodiments, examples of arthritis include, but are not limited to, osteoarthritis, rheumatoid arthritis, septic arthritis, gout and pseudo-gout, juvenile idiopathic arthritis, psoriatic arthritis, Still's disease, and ankylosing spondylitis. In some embodiments, the dendrimer is co-administered with an additional agent(s) so as to enhance such a treatment.

Additional embodiments will be apparent to persons skilled in the relevant art based on the teachings contained herein.

DESCRIPTION OF THE DRAWINGS

FIG. 2 shows various branch units and how re-generation of reactive functionality is achieved in various dendrimer systems.

FIG. 19 (A, B, and C) shows a diagram of a dendrimer conjugate provided in some embodiments of the present invention.

FIG. 23 (A, B, C, and D) shows a diagram of a dendrimer conjugate provided in some embodiments of the present invention.

FIGS. 31A and B depicts dendrimer conjugates provided in some embodiments of the present invention.

FIG. 32 shows a dendrimer comprising a simple ester (top portion of figure) and a dendrimer conjugate comprising an elimination linker (e.g., a 1,6, elimination linker/spacer as shown in the bottom portion).

DEFINITIONS

Figure 1:
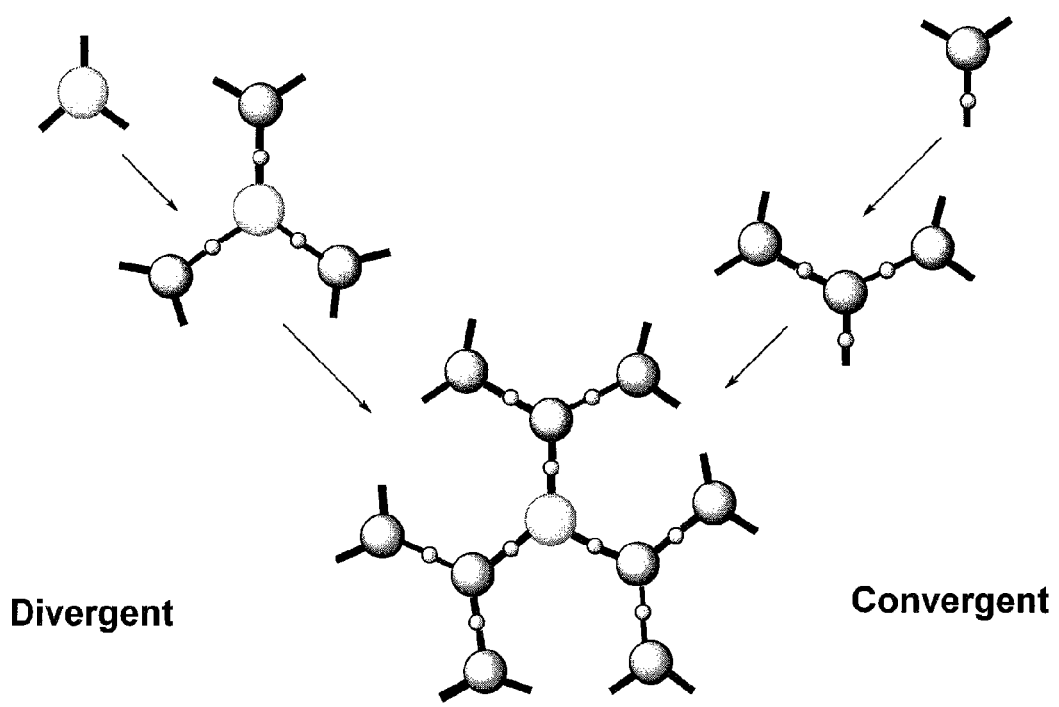
FIG. 1 shows a diagram illustrating divergent dendrimer synthesis in comparison to convergent synthesis.
Figure 3:
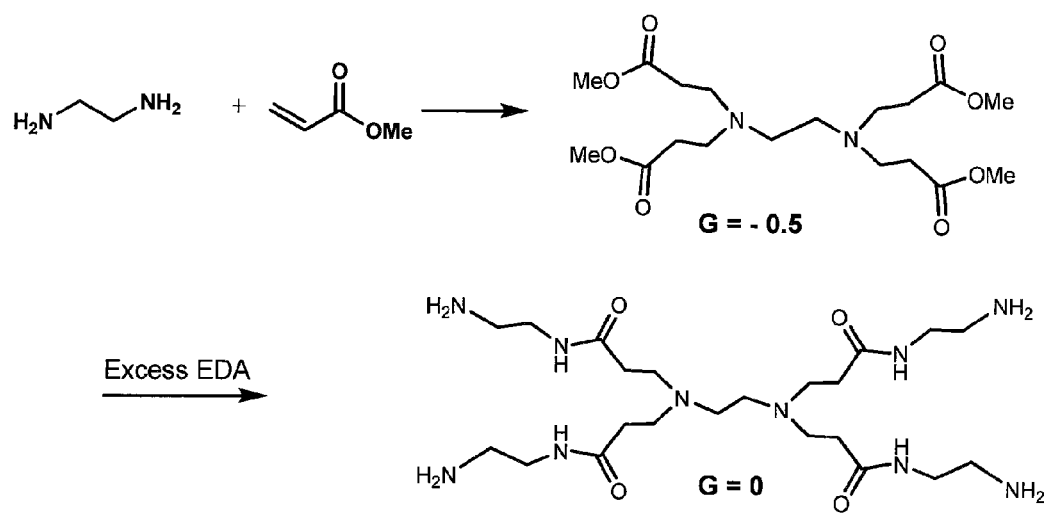
FIG. 3 shows the classical synthesis reaction for Tomalia PAMAM dendrimers

To facilitate an understanding of the present invention, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass) but for whom a confirmatory test (e.g., biopsy and/or histology) has not been done or for whom the stage of cancer is not known. The term further includes people who once had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention.

As used herein, the term "initial diagnosis" refers to a test result of initial cancer diagnosis that reveals the presence or absence of cancerous cells (e.g., using a biopsy and histology).

As used herein, the term "identifying the risk of said tumor metastasizing" refers to the relative risk (e.g., the percent chance or a relative score) of a tumor metastasizing.

As used herein, the term "identifying the risk of said tumor recurring" refers to the relative risk (e.g., the percent chance or a relative score) of a tumor recurring in the same organ as the original tumor.

As used herein, the term "subject at risk for cancer" refers to a subject with one or more risk factors for developing a specific cancer. Risk factors include, but are not limited to, gender, age, genetic predisposition, environmental expose, and previous incidents of cancer, preexisting non-cancer diseases, and lifestyle.

As used herein, the term "characterizing cancer in subject" refers to the identification of one or more properties of a cancer sample in a subject, including but not limited to, the presence of benign, pre-cancerous or cancerous tissue and the stage of the cancer.

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

As used herein, the term "characterizing tissue in a subject" refers to the identification of one or more properties of a tissue sample (e.g., including but not limited to, the presence of cancerous tissue, the presence of pre-cancerous tissue that is likely to become cancerous, and the presence of cancerous tissue that is likely to metastasize.

As used herein, the term "providing a prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "non-human animals" refers to all non-human animals including, but not limited to, vertebrates such as rodents, non-human primates, ovines, bovines, ruminants, lagomorphs, porcines, caprines, equines, canines, felines, ayes, etc.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

As used herein, the term "drug" is meant to include any molecule, molecular complex or substance administered to an organism for diagnostic or therapeutic purposes, including medical imaging, monitoring, contraceptive; cosmetic, nutraceutical, pharmaceutical and prophylactic applications. The term "drug" is further meant to include any such molecule, molecular complex or substance that is chemically modified and/or operatively attached to a biologic or biocompatible structure.

As used herein, the term "purified" or "to purify" or "compositional purity" refers to the removal of components (e.g., contaminants) from a sample or the level of components (e.g., contaminants) within a sample. For example, unreacted moieties, degradation products, excess reactants, or byproducts are removed from a sample following a synthesis reaction or preparative method.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using screening methods known in the art.

As used herein, the term "NAALADase inhibitor" refers to any one of a multitude of inhibitors for the neuropeptidase NAALADase (N-acetylated-alpha linked acidic dipeptidase). Such inhibitors of NAALADase have been well characterized. For example, an inhibitor can be selected from the group comprising, but not limited to, those found in U.S. Pat. No. 6,011,021, herein incorporated by reference in its entirety.

As used herein, the term "nanodevice" or "nanodevices" refer, generally, to compositions comprising dendrimers of the present invention. As such, a nanodevice may refer to a composition comprising a dendrimer and metal nanoparticles (e.g., iron oxide nanoparticles (e.g., poly(styrene sulfonate) (PSS)-coated iron oxide nanoparticles)) of the present invention that may contain one or more functional groups (e.g., a therapeutic agent) conjugated to the dendrimer. A nanodevice may also refer to a composition comprising two or more different dendrimers of the present invention.

As used herein, the term "degradable linkage," when used in reference to a polymer (e.g., PEG-hRNase conjugate of the present invention), refers to a conjugate that comprises a physiologically cleavable linkage (e.g., a linkage that can be hydrolyzed (e.g., in vivo) or otherwise reversed (e.g., via enzymatic cleavage). Such physiologically cleavable linkages include, but are not limited to, ester, carbonate ester, carbamate, sulfate, phosphate, acyloxyalkyl ether, acetal, and ketal linkages (See, e.g., U.S. Pat. No. 6,838,076, herein incorporated by reference in its entirety). Similarly, the conjugate may comprise a cleavable linkage present in the linkage between the polymer and hRNase, or, may comprise a cleavable linkage present in the polymer itself (e.g., such that when cleaved, a small portion of the polymer remains on the hRNase molecule) (See, e.g., U.S. Pat. App. Nos. 20050158273 and 20050181449, each of which is herein incorporated by reference in its entirety). For example, a PEG polymer comprising an ester linkage can be utilized for conjugation to hRNase to create a PEG-hRNase conjugate (See, e.g., Kuzlowski et al., Biodrugs, 15, 419-429 (2001). A conjugate that comprises a degradable linkage of the present invention is capable of generating hRNase that is free (e.g., completely or partially free) of the polymer (e.g., in vivo after hydrolysis of the linkage).

A "physiologically cleavable" or "hydrolysable" or "degradable" bond is a bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides and oligonucleotides.

An "enzymatically degradable linkage" means a linkage that is subject to degradation by one or more enzymes.

A "hydrolytically stable" linkage or bond refers to a chemical bond (e.g., typically a covalent bond) that is substantially stable in water (i.e., does not undergo hydrolysis under physiological conditions to any appreciable extent over an extended period of time). Examples of hydrolytically stable linkages include, but are not limited to, carbon-carbon bonds (e.g., in aliphatic chains), ethers, amides, urethanes, and the like.

As used herein, the term "click chemistry" refers to chemistry tailored to generate substances quickly and reliably by joining small modular units together (see, e.g., Kolb et al. (2001) Angewandte Chemie Intl. Ed. 40:2004-2011; Evans (2007) Australian J. Chem. 60:384-395; Carlmark et al. (2009) Chem. Soc. Rev. 38:352-362; each herein incorporated by reference in its entirety).

As used herein, the term "triazine" refers to a compound comprising a ring structure bearing three nitrogen atoms. In some embodiments, the ring structure is six-membered (e.g., the molecular formula comprises $C_3H_3N_3$). In some embodiments, the ring is a conjugated system. Triazine moieties with six-membered rings may have nitrogen atoms at any possible placement so long as three nitrogen atoms occur in the ring (e.g., 1,2,3-triazine; 1,2,4-triazine, 1,3,5-triazine, 1,2,5-triazine, 1,2,6-triazine, etc.).

As used herein, the term "scaffold" refers to a compound to which other moieties are attached (e.g., conjugated). In some embodiments, a scaffold is conjugated to bioactive functional conjugates (e.g., a therapeutic agent, a targeting agent, a trigger agent, an imaging agent). In some embodiments, a scaffold is conjugated to a dendrimer (e.g., a PAMAM Baker-Huang dendrimer). In some embodiments, conjugation of a scaffold to a dendrimer and/or a functional conjugate(s) is direct, while in other embodiments conjugation of a scaffold to a dendrimer and/or a functional conjugate(s) is indirect, e.g., an intervening linker is present between the scaffold compound and the dendrimer, and/or the scaffold and the functional conjugate(s).

As used herein, the term "one-pot synthesis reaction" or equivalents thereof, e.g., "1-pot", "one pot", etc., refers to a chemical synthesis method in which all reactants are present in a single vessel. Reactants may be added simultaneously or sequentially, with no limitation as to the duration of time elapsing between introduction of sequentially added reactants. In some embodiments, conjugation between a dendrimer (e.g., a terminal arm of a dendrimer) and a functional ligand is accomplished during a "one-pot" reaction. In some embodiments, a one-pot reaction occurs wherein a hydroxyl-terminated dendrimer (e.g., HO-PAMAM dendrimer) is reacted with one or more functional ligands (e.g., a therapeutic agent, a pro-drug, a trigger agent, a targeting agent, an imaging agent) in one vessel, such conjugation being facilitated by ester coupling agents (e.g., 2-chloro-1-methylpyridinium iodide and 4-(dimethylamino) pyridine) (see, e.g., International Patent Application No. PCT/US2010/042556, herein incorporated by reference in its entirety).

As used herein, the term "solvent" refers to a medium in which a reaction is conducted. Solvents may be liquid but are not limited to liquid form. Solvent categories include but are not limited to nonpolar, polar, protic, and aprotic.

As used herein, the term "dialysis" refers to a purification method in which the solution surrounding a substance is exchanged over time with another solution. Dialysis is generally performed in liquid phase by placing a sample in a chamber, tubing, or other device with a selectively permeable membrane. In some embodiments, the selectively permeable membrane is cellulose membrane. In some embodiments, dialysis is performed for the purpose of buffer exchange. In some embodiments, dialysis may achieve concentration of the original sample volume. In some embodiments, dialysis may achieve dilution of the original sample volume.

As used herein, the term "precipitation" refers to purification of a substance by causing it to take solid form, usually within a liquid context. Precipitation may then allow collection of the purified substance by physical handling, e.g. centrifugation or filtration.

As used herein, an "ester coupling agent" refers to a reagent that can facilitate the formation of an ester bond between two reactants. The present invention is not limited to any particular coupling agent or agents. Examples of coupling agents include but are not limited to 2-chloro-1-methylpyridium iodide and 4-(dimethylamino)pyridine, or dicyclohexylcarbodiimide and 4-(dimethylamino)pyridine or diethyl azodicarboxylate and triphenylphosphine or other carbodiimide coupling agent and 4-(dimethylamino)pyridine.

As used herein, the term "glycidolate" refers to the addition of a 2,3-dihydroxylpropyl group to a reagent using glycidol as a reactant. In some embodiments, the reagent to which the 2,3-dihydroxylpropyl groups are added is a dendrimer. In some embodiments, the dendrimer is a PAMAM dendrimer. Glycidolation may be used generally to add terminal hydroxyl functional groups to a reagent.

As used herein, the term "ligand" refers to any moiety covalently attached (e.g., conjugated) to a dendrimer branch; in preferred embodiments, such conjugation is indirect (e.g., an intervening moiety exists between the dendrimer branch and the ligand) rather than direct (e.g., no intervening moiety exists between the dendrimer branch and the ligand). Indirect attachment of a ligand to a dendrimer may exist where a scaffold compound (e.g., triazine scaffold (see, e.g., PCT/US2010/050893; herein incorporated by reference in its entirety)) (e.g., a trigger agent) (e.g., a linker) intervenes. In preferred embodiments, ligands have functional utility for specific applications, e.g., for therapeutic, targeting, imaging, or drug delivery function(s). The terms "ligand", "conjugate", and "functional group" may be used interchangeably.

As used herein, the term "Baker-Huang dendrimer" or "Baker-Huang PAMAM dendrimer" refers to a dendrimer comprised of branching units of structure:

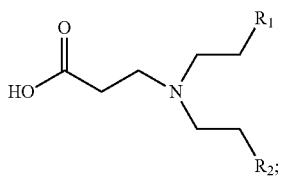

wherein R1 and R2 are independently selected from the group consisting of

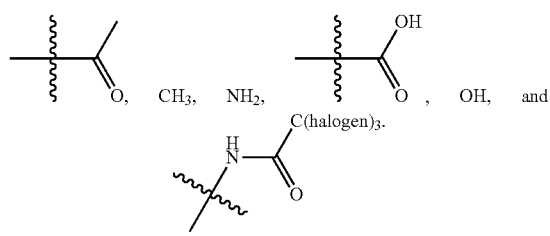

In some embodiments, the branching unit is activated to its HNS ester. In some embodiments, such activation is achieved using TSTU (O—(N-succinimidyl)-1,1,3,3-tetramethyluronium tetrafluoroborate). In some embodiments, EDA is added. In some embodiments, the dendrimer is further treated to replace, e.g., $CF_3$ functional groups with $NH_2$ functional groups; for example, in some embodiments, a $CF_3$-containing version of the dendrimer is treated with $K_2CO_3$ to yield a dendrimer with terminal $NH_2$ groups (for example, as shown in Scheme 2). In some embodiments, terminal groups of a Baker-Huang dendrimer are further derivatized and/or further conjugated with other moieties. For example, one or more functional ligands (e.g., for therapeutic, targeting, imaging, or drug delivery function(s)) may be conjugated to a Baker-Huang dendrimer, either via direct conjugation to terminal branches or indirectly (e.g., through linkers, through other functional groups (e.g., through an OH— functional group)). In some embodiments, the order of iterative repeats from core to surface is amide bonds first, followed by tertiary amines, with ethylene groups intervening between the amide bond and tertiary amines. In preferred embodiments, a Baker-Huang dendrimer is synthesized by convergent synthesis methods.

As used herein, the term "branching unit agent" refers to a repeating structure present in a dendrimer. In some embodiments, the dendrimer is a PAMAM dendrimer. In some embodiments, the dendrimer is a Baker-Huang PAMAM dendrimer. In some embodiments, the branch unit is an $AB_2$ branch unit wherein A comprises a carboxylic acid, and B comprises a protected amine. In some embodiments, amide bond formation between $AB_2$ branch units finds use for addition of subsequent generations of dendrimer branches. In some embodiments, the branching unit agent has the following formula:

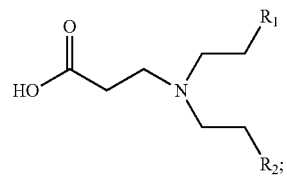

wherein R1 and R2 are independently selected from the group consisting of

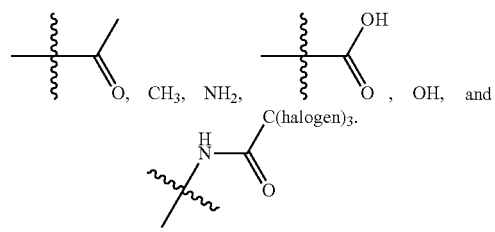

As used herein, the term "Tomalia PAMAM dendrimer" or "Tomalia dendrimer" refers to a PAMAM dendrimer with iterative repeats (stated in order from core to surface) of tertiary amines followed by amide bonds, with ethylene groups intervening between the tertiary amines and amide bonds.

As used herein, the term "classical PAMAM synthesis" or "classical PAMAM synthesis method" refer to divergent synthesis methods involving branch growth through Michael addition in the presence of large excesses of EDA, e.g., as described herein and in Fréchet, J. M. J., Tomalia, D. A., Editors, Dendrimers and other Dendritic Polymers (2001) J. Wiley and Sons, Chichester and New York, herein incorporated by reference in its entirety.

DETAILED DESCRIPTION OF THE INVENTION

Dendrimeric polymers have been described extensively (See, e.g., Tomalia, Advanced Materials 6:529 (1994); Angew, Chem. Int. Ed. Engl., 29:138 (1990); incorporated herein by reference in their entireties). Dendrimer polymers are synthesized as defined spherical structures typically ranging from 1 to 20 nanometers in diameter. Methods for manufacturing a G5 PAMAM dendrimer with a protected core is shown (FIGS. 18-22) (e.g., the protected core diamine is $NH_2$—$CH_2$—$CH_2$—NHPG). Molecular weight and the number of terminal groups increase exponentially as a function of generation (the number of layers) of the polymer (See, e.g., FIG. 23A, B, C and D). Different types of dendrimers can be synthesized based on the core structure that initiates the polymerization process (See e.g., FIGS. 18-22).

The dendrimer core structures dictate several characteristics of the molecule such as the overall shape, density and surface functionality (See, e.g., Tomalia et al., Chem. Int. Ed. Engl., 29:5305 (1990)). Spherical dendrimers can have ammonia as a trivalent initiator core or ethylenediamine (EDA) as a tetravalent initiator core (See, e.g., FIG. 23A, B, C and D). Recently described rod-shaped dendrimers (See, e.g., Yin et al., J. Am. Chem. Soc., 120:2678 (1998)) use polyethyleneimine linear cores of varying lengths; the longer the core, the longer the rod. Dendritic macromolecules are available commercially in kilogram quantities and are produced under current good manufacturing processes (GMP) for biotechnology applications.

Numerous U.S. patents describe methods and compositions for producing dendrimers. Examples of some of these patents are given below in order to provide a description of some dendrimer compositions that may be useful in the present invention, however it should be understood that these are merely illustrative examples and numerous other similar dendrimer compositions could be used in the present invention.

U.S. Pat. No. 4,507,466, U.S. Pat. No. 4,558,120, U.S. Pat. No. 4,568,737, and U.S. Pat. No. 4,587,329 each describe methods of making dense star polymers with terminal densities greater than conventional star polymers. These polymers have greater/more uniform reactivity than conventional star polymers, i.e. 3rd generation dense star polymers. These patents further describe the nature of the amidoamine dendrimers and the 3-dimensional molecular diameter of the dendrimers.

U.S. Pat. No. 4,631,337 describes hydrolytically stable polymers. U.S. Pat. No. 4,694,064 describes rod-shaped dendrimers. U.S. Pat. No. 4,713,975 describes dense star polymers and their use to characterize surfaces of viruses, bacteria and proteins including enzymes. Bridged dense star polymers are described in U.S. Pat. No. 4,737,550. U.S. Pat. No. 4,857,599 and U.S. Pat. No. 4,871,779 describe dense star polymers on immobilized cores useful as ion-exchange resins, chelation resins and methods of making such polymers.

U.S. Pat. No. 5,338,532 is directed to starburst conjugates of dendrimer(s) in association with at least one unit of carried agricultural, pharmaceutical or other material. This patent describes the use of dendrimers to provide means of delivery of high concentrations of carried materials per unit polymer, controlled delivery, targeted delivery and/or multiple species such as e.g., drugs antibiotics, general and specific toxins, metal ions, radionuclides, signal generators, antibodies, interleukins, hormones, interferons, viruses, viral fragments, pesticides, and antimicrobials.

U.S. Pat. No. 6,471,968 describes a dendrimer complex comprising covalently linked first and second dendrimers, with the first dendrimer comprising a first agent and the second dendrimer comprising a second agent, wherein the first dendrimer is different from the second dendrimer, and where the first agent is different than the second agent.

Other useful dendrimer type compositions are described in U.S. Pat. No. 5,387,617, U.S. Pat. No. 5,393,797, and U.S. Pat. No. 5,393,795 in which dense star polymers are modified by capping with a hydrophobic group capable of providing a hydrophobic outer shell. U.S. Pat. No. 5,527,524 discloses the use of amino terminated dendrimers in antibody conjugates.

The use of dendrimers as metal ion carriers is described in U.S. Pat. No. 5,560,929. U.S. Pat. No. 5,773,527 discloses non-crosslinked polybranched polymers having a comb-burst configuration and methods of making the same. U.S. Pat. No. 5,631,329 describes a process to produce polybranched polymer of high molecular weight by forming a first set of branched polymers protected from branching; grafting to a core; deprotecting first set branched polymer, then forming a second set of branched polymers protected from branching and grafting to the core having the first set of branched polymers, etc.

U.S. Pat. No. 5,902,863 describes dendrimer networks containing lipophilic organosilicone and hydrophilic polyanicloamine nanoscopic domains. The networks are prepared from copolydendrimer precursors having PAMAM (hydrophilic) or polyproyleneimine interiors and organosilicon outer layers. These dendrimers have a controllable size, shape and spatial distribution. They are hydrophobic dendrimers with an organosilicon outer layer that can be used for specialty membrane, protective coating, composites containing organic organometallic or inorganic additives, skin patch delivery, absorbents, chromatography personal care products and agricultural products.

U.S. Pat. No. 5,795,582 describes the use of dendrimers as adjuvants for influenza antigen. Use of the dendrimers produces antibody titer levels with reduced antigen dose. U.S. Pat. No. 5,898,005 and U.S. Pat. No. 5,861,319 describe specific immunobinding assays for determining concentration of an analyte. U.S. Pat. No. 5,661,025 provides details of a self-assembling polynucleotide delivery system comprising dendrimer polycation to aid in delivery of nucleotides to target site. This patent provides methods of introducing a polynucleotide into a eukaryotic cell in vitro comprising contacting the cell with a composition comprising a polynucleotide and a dendrimer polyeation non-covalently coupled to the polynucleotide.

Classical preparation of PAMAM dendrimers is performed according to a typical divergent (building up the macromolecule from an initiator core) synthesis. It involves a two-step growth sequence that includes of a Michael addition of amino groups to the double bond of methyl acrylate (MA) followed by the amidation of the resulting terminal carbomethoxy, —($CO_2$ $CH_3$) group, with ethylenediamine (EDA).

In the first step of this process, ammonia is allowed to react under an inert nitrogen atmosphere with MA (molar ratio: 1:4.25) at 47° C. for 48 hours. The resulting compound is referred to as generation=0, the star-branched PAMAM tri-ester. The next step involves reacting the tri-ester with an excess of EDA to produce the star-branched PAMAM tri-amine (G=O). This reaction is performed under an inert atmosphere (nitrogen) in methanol and requires 48 hours at 0° C.

for completion. Reiteration of this Michael addition and amidation sequence produces generation=1.

Preparation of this tri-amine completes the first full cycle of the divergent synthesis of PAMAM dendrimers. Repetition of this reaction sequence results in the synthesis of larger generation (G=1-5) dendrimers (i.e., ester- and amine-terminated molecules, respectively). For example, the second iteration of this sequence produces generation 1, with an hexa-ester and hexa-amine surface, respectively. The same reactions are performed in the same way as for all subsequent generations from 1 to 9, building up layers of branch cells giving a core-shell architecture with precise molecular weights and numbers of terminal groups as shown above. Carboxylate-surfaced dendrimers can be produced by hydrolysis of ester-terminated PAMAM dendrimers, or reaction of succinic anhydride with amine-surfaced dendrimers (e.g., full generation PAMAM, POPAM or POPAM-PAMAM hybrid dendrimers).

Various dendrimers can be synthesized based on the core structure that initiates the polymerization process. These core structures dictate several important characteristics of the dendrimer molecule such as the overall shape, density, and surface functionality (See, e.g., Tomalia et al., Angew. Chem. Int. Ed. Engl., 29:5305 (1990)). Spherical dendrimers derived from ammonia possess trivalent initiator cores, whereas EDA is a tetra-valent initiator core. Recently, rod-shaped dendrimers have been reported which are based upon linear poly (ethyleneimine) cores of varying lengths the longer the core, the longer the rod (See, e.g., Yin et al., J. Am. Chem. Soc., 120:2678 (1998)).

Figure 4:
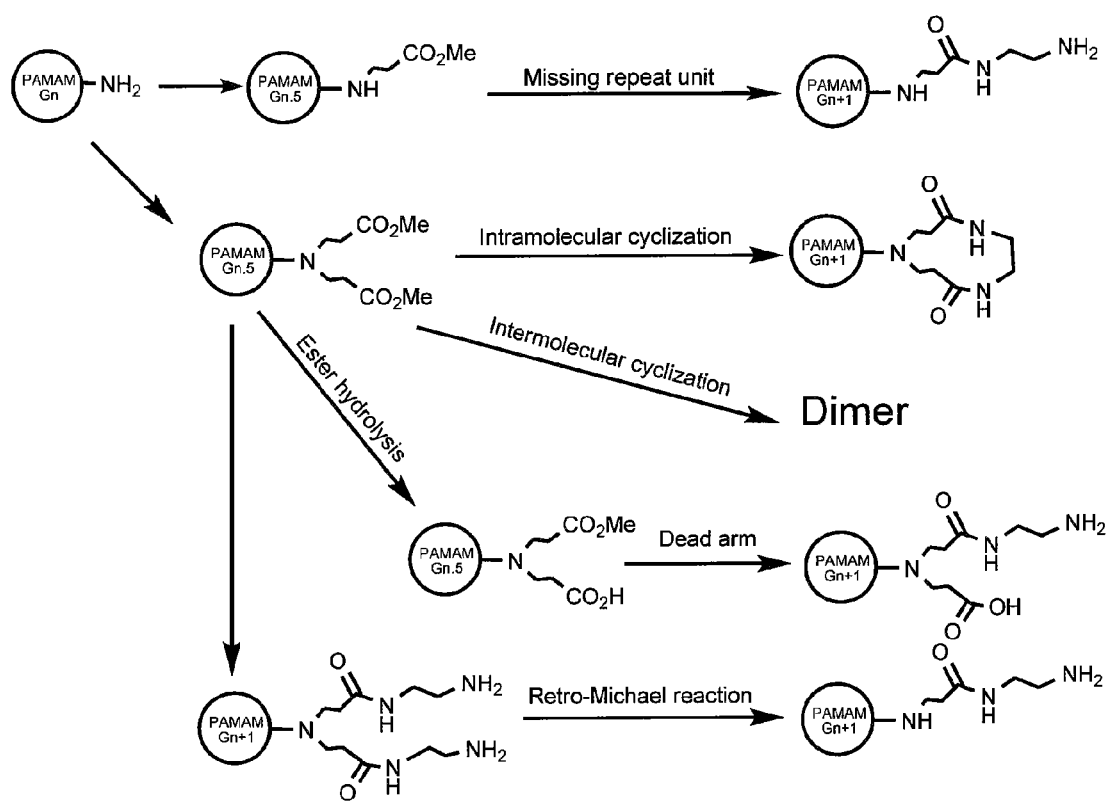
FIG. 4 shows common structural defects occurring in classically-synthesized Tomalia PAMAM dendrimers, and how such defects arise.
Figure 5:
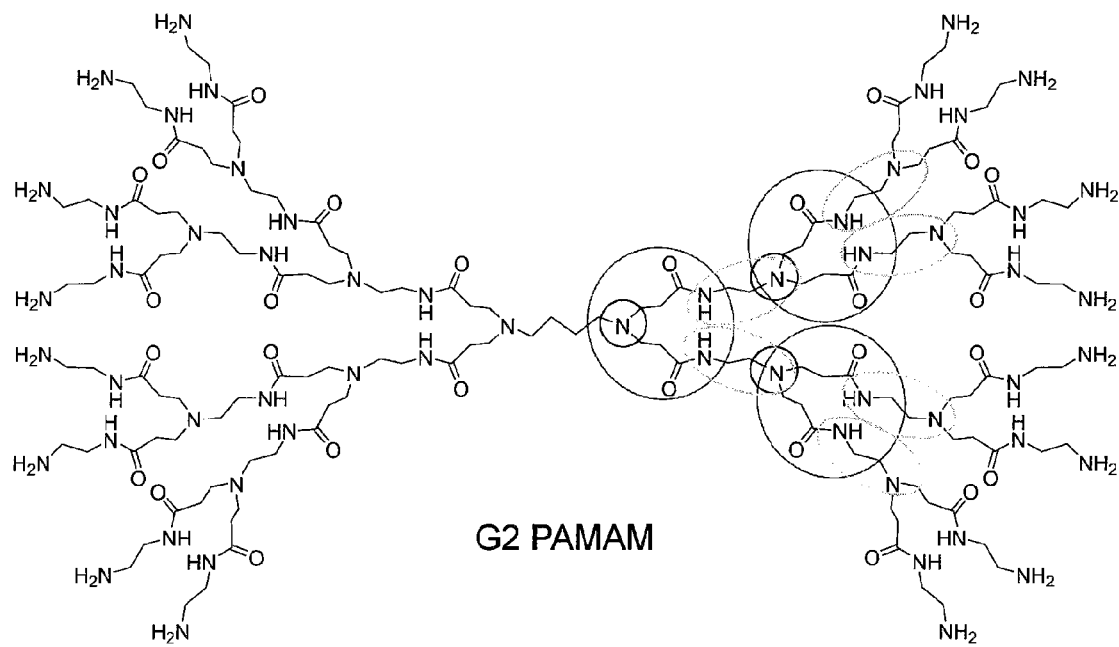
FIG. 5 shows the structure of a generation 2 (G2) classical Tomalia PAMAM dendrimer.

Therefore, classical methods of synthesizing PAMAM dendrimers (e.g., Tomalia PAMAM dendrimers) include two repeated steps, Michael addition and amidation. These synthesis methods require a large excess of ethylene diamine for the amidation step to avoid structural flaws in the resulting dendrimers, such flaws including but not limited to (a) intramolecular polymerization of dendrimer (e.g., resulting in dimers, trimers, and tetramers); and (b) intermolecular looping. In classical methods of synthesizing PAMAM dendrimers (e.g., Tomalia PAMAM dendrimers), the excess of EDA typically required for the synthesis of G0 from G(−0.5) is 101 equivalents per ester, and the excess of EDA doubles for every generation beyond this. Therefore, in classical methods of synthesizing PAMAM dendrimers (e.g., Tomalia PAMAM dendrimers), for the synthesis of G5, the EDA excess required is up to 3,232 equivalents per ester. Such requirements preclude the scale up for PAMAM dendrimers (e.g., Tomalia PAMAM dendrimers) in a chemistry lab setting using such classical synthesis methods. In addition, classical PAMAM dendrimers are prone to several other structural defects that are artifacts of the synthesis method and that are difficult, if not impossible, to avoid. Such problems include, for example, retro-Michael reactions and incomplete amidations resulting in missing branches. Examples of common structural defects occurring in classically synthesized PAMAM dendrimers (e.g., Tomalia PAMAM dendrimers) are shown in FIG. 4. FIG. 5 shows the desired structure of a generation 2 (G2) classically synthesized Tomalia PAMAM dendrimer, including indications of branch points and branching units arising via iterative Michael addition reactions and incorporation of EDA.

The present invention overcomes such limitations. In particular, some embodiments of the present invention are directed to novel polyamidoamine (PAMAM) dendrimers, novel dendrimer branching units for generating such novel PAMAM dendrimers, methods for synthesizing such novel PAMAM dendrimers, as well as systems and methods utilizing the dendrimers (e.g., in diagnostic and/or therapeutic settings (e.g., for the delivery of therapeutics, imaging, and/or targeting agents (e.g., in disease diagnosis and/or therapy, etc.))).

Figure 10:
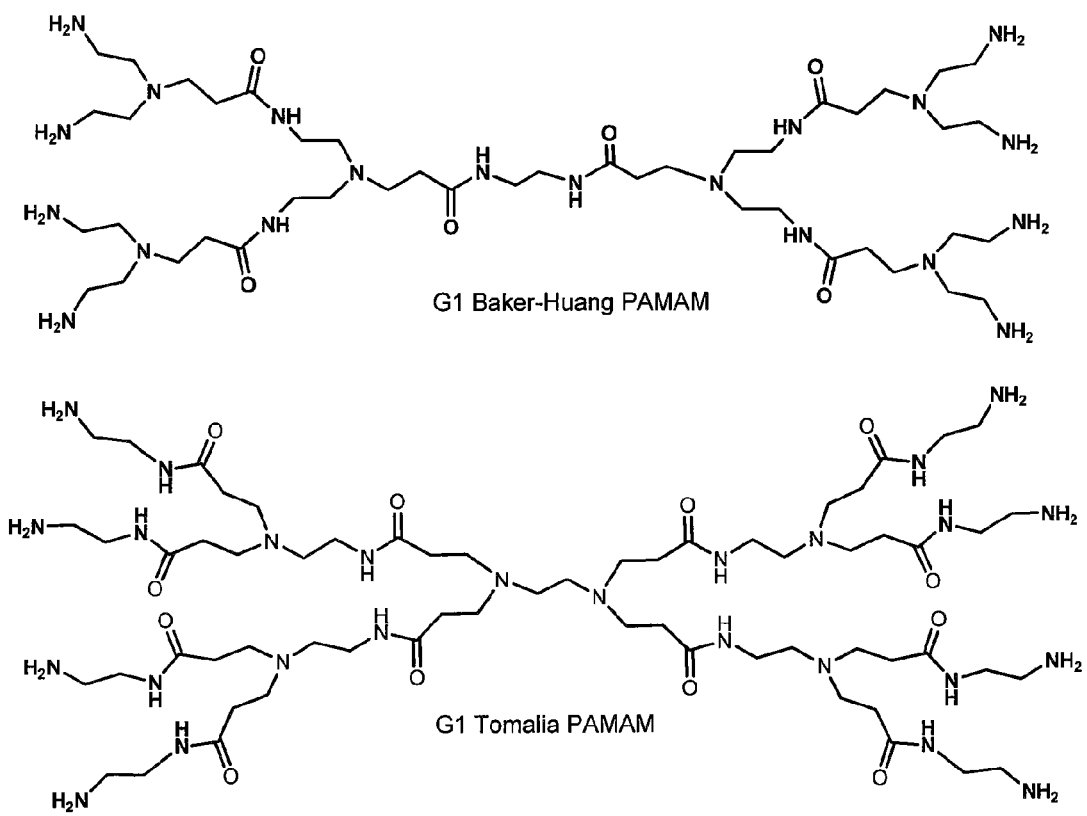
FIG. 10 shows the structure of one embodiment of a generation 1 (G1) Baker-Huang $NH_2$-terminated PAMAM dendrimer as compared to the structure of a generation 1 (G1) Tomalia $NH_2$-terminated PAMAM dendrimer. Notably, the central region of the Baker-Huang dendrimer embodiment includes additional NH— and =O groups, which provide potential points of attachment for functional ligands (e.g., targeting agents, therapeutic agents, imaging agents, trigger agents).

The PAMAM dendrimer embodiments of the present invention (e.g., Baker-Huang PAMAM dendrimers) are structurally distinct from classical PAMAM dendrimers (e.g., Tomalia PAMAM dendrimers). FIG. 10 shows a comparison of an embodiment of a generation 1 (G1) Baker-Huang PAMAM dendrimer and a classical Tomalia G1 PAMAM dendrimer. While both dendrimers are poly-amido-amine (PAMAM) dendrimers, they are structurally distinct. The Tomalia PAMAM dendrimer structure includes (listed in order from the core to the surface) iterative repeats of tertiary amines followed by amide bonds with ethylene groups intervening between the tertiary amines and amide bonds. In contrast, in one embodiment of a dendrimer composition of the present invention (e.g., a Baker-Huang PAMAM dendrimer), the order of iterative repeats from core to surface changes to amide bonds first, followed by tertiary amines, again with ethylene groups intervening between the amide bond and tertiary amines.

Table 1 shows additional structural differences and similarities existing between classical (e.g., Tomalia PAMAM dendrimers) and dendrimer embodiments of the present invention (e.g., Baker-Huang PAMAM dendrimers). The first two columns of Table 1 indicate the number of surface amino groups, which find use, e.g., with regard to conjugation of functional ligands (e.g., a therapeutic agent, an imaging agent, a targeting agent, a trigger agent). Both types of PAMAM dendrimer have the same number of surface groups at a given generation (generations 3 or 4 are considered in Table 1). The second two columns of Table 1 indicate the numbers of bonds counting from core to surface, which are also similar; for G3 it is 29.5, and G4 it is 36.5. This number determines approximate size of the dendrimer, especially at higher generations. The third two columns indicate the numbers of tertiary amine throughout the dendrimer structure, are similar for the two types of PAMAM dendrimers. The next two parameters illustrated are the number of amide bonds and the molecular weight of these two PAMAM dendrimers.

TABLE 1

Structural comparison of Baker-Huang PAMAM dendrimers ("Baker PAMAM") and classical PAMAM dendrimers ("Tomalia PAMAM"), using generation 3 (G3) and generation 4 (G4) dendrimers as examples.

| Generation | # of surface amine | | # of bonds core-surface | | # of tertiary amine | | # of amide bond | | Molecular Weight | |
|---|---|---|---|---|---|---|---|---|---|---|
| | G3 | G4 | G3 | G4 | G3 | G4 | G3 | G4 | G3 | G4 |
| Baker PAMAM | 32 | 64 | 29.5 | 36.5 | 30 | 62 | 30 | 62 | 4,777 | 9,801 |
| Tomalia PAMAM | 32 | 64 | 29.5 | 36.5 | 30 | 62 | 60 | 124 | 6,909 | 14,214 |

While structural similarities exist between classical (e.g., Tomalia PAMAM dendrimers) and dendrimer embodiments of the present invention (e.g., Baker-Huang PAMAM dendrimers), there are also structural distinctions. Notably, Baker-Huang PAMAM dendrimers have fewer amide bonds and a less crowded interior (core) (see, Table 1 and FIG. 10). In particular, the interior core of some dendrimer embodiments of the present invention (see, e.g., FIG. 10) permits increased interior space and less steric hindrance, which finds use, e.g., for encapsulation of agents or attachment of additional functional ligands (e.g., therapeutic agents, imaging agents, trigger agents, targeting agents).

In certain embodiments, the Baker-Huang dendrimers have a repeating [(tertiary amine-amide)n-(tertiary amine-amide-amide-tertiary amine)-(amide-tertiary amine)n]dendrimer structure wherein n is limitless (e.g., 1, 2, 3, 4, 5, 10, 25, 50, 75, 100, 1000, 10000, etc.). In some embodiments, the tertiary amines and amide components are independently separated by alkyl chains of any length (e.g., methyl, ethyl, propyl, butyl, pentyl, hexyl, heptyl, octyl, etc.). In some embodiments, the terminal tertiary amines are conjugated with functional ligands (e.g., a targeting agent, a therapeutic agent, a pro-drug, an imaging agent, and a trigger agent).

In certain embodiments, the Baker-Huang dendrimers have the following formula:

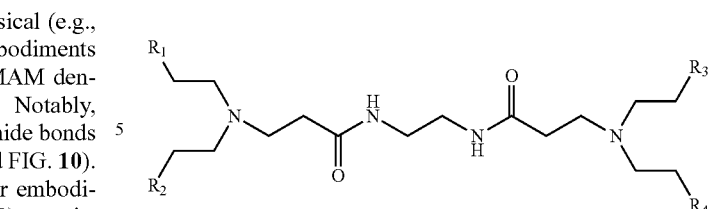

wherein R1, R2, R3, R4 are

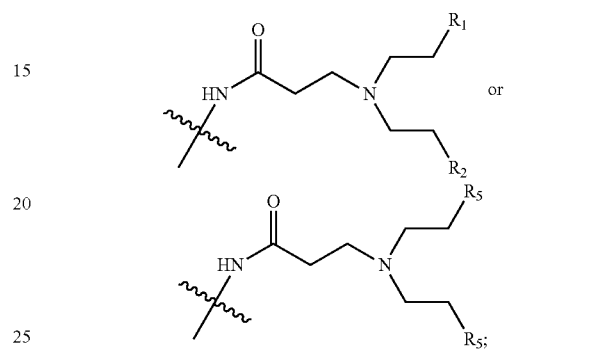

wherein R5 is a targeting agent, a therapeutic agent, a pro-drug, an imaging agent, or a trigger agent.

In some embodiments, the Baker-Huang dendrimers have the following formula:

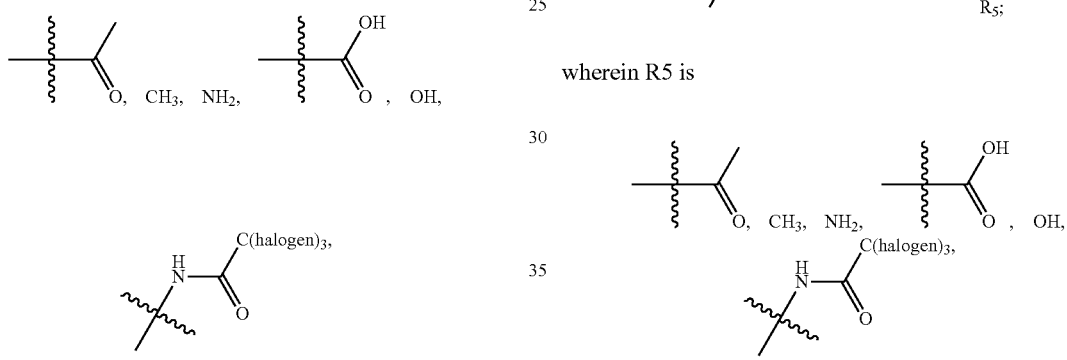

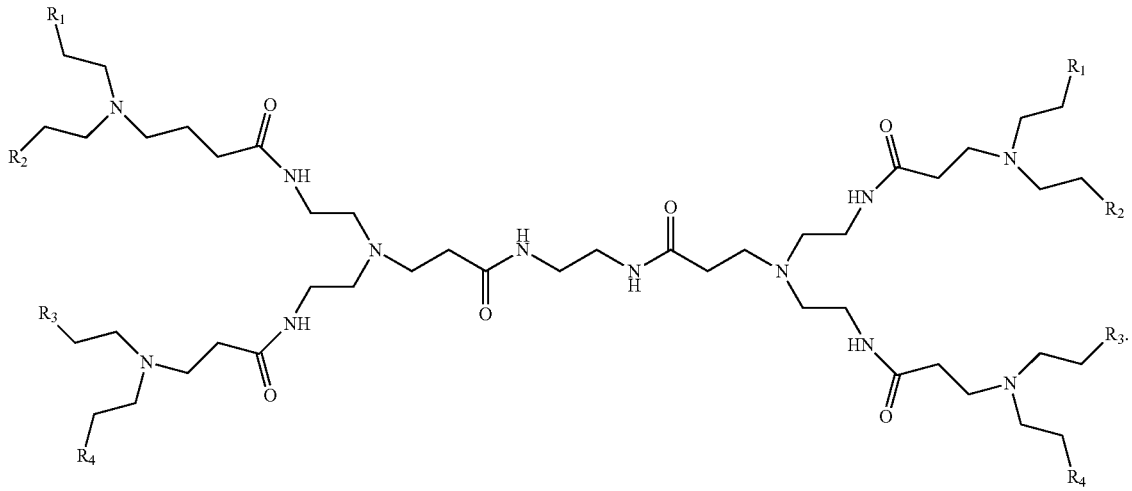

The compositions are not limited to a particular manner of synthesis. In some embodiments, the composition is produced by a convergent synthesis reaction.

Figure 6:
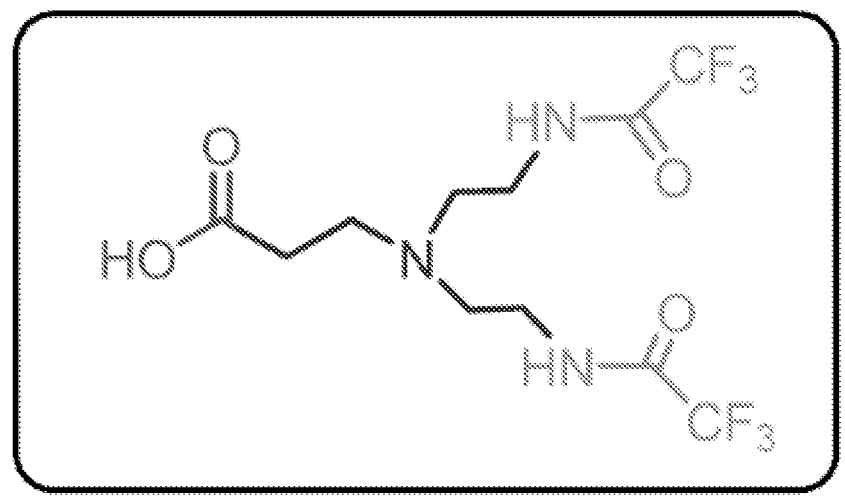
FIG. 6 shows an embodiment of an $AB_2$ branch unit of the present invention.

The present invention is not limited to a particular method for synthesizing Baker-Huang PAMAM dendrimers. In certain embodiments, the present invention provides novel dendrimer branching units for generating Baker-Huang PAMAM dendrimers. FIG. 6 shows one embodiment of an $AB_2$ branch unit of the present invention. In the terminology used herein regarding branch units, A may comprise a carboxylic acid, and B may comprise a protected amine. In some synthesis method embodiments, amide bond formation is utilized for generation growth of dendrimers constructed using $AB_2$, branch unit embodiments of the present invention. For example, for a EDA core, the $AB_2$ branch unit embodiment shown in FIG. 6 reacts at both end of the EDA molecule, thereby forming a G0 dendrimer (e.g., Baker-Huang PAMAM G0 dendrimer). In the embodiment shown in FIG. 6, the selection of trifluoroacetamide as a protection group for the primary amine has several advantages. For example, trifluoroacetamide is very stable under acidic conditions; therefore, the solubility of the branch unit embodiment in organic solvent is desirable because the coupling reactions may be performed in organic solvent. Additionally, trifluoroacetamide can be removed under mild conditions.

In certain embodiments, the present invention provides compositions comprising novel PAMAM dendrimers (e.g., Baker-Huang dendrimers) conjugated with one or more functional groups (e.g., imaging agents, targeting agents, therapeutic agents, scaffold agents, linkers, trigger agents, locking agents, etc.). In some embodiments, conjugation of a functional group with the dendrimer is accomplished with a linker and/or a trigger agent.

In some embodiments, a dendrimer (e.g., a Baker-Huang PAMAM dendrimer) conjugated to a linker that is conjugated to a functional group (e.g., therapeutic agent, imaging agent, targeting agent, triggering agent) decreases the number of conjugation steps required to form a dendrimer conjugate (e.g., a dendrimer conjugated to a targeting agent, imaging agent, therapeutic agent and/or triggering agent). For example, in some embodiments, the present invention provides a customizable dendrimer (e.g., a Baker-Huang PAMAM dendrimer) wherein one or a plurality of linkers (e.g. attached to one or a plurality of targeting agents, triggering agents and/or therapeutic agents) are conjugated to the dendrimer, thereby decreasing the number of conjugation steps used to form a dendrimer conjugate (e.g., versus a dendrimer that is conjugated to a targeting moiety in one step and that is separately conjugated to a linker (e.g., comprising a therapeutic agent, imaging agent, triggering agent or other moiety) in an additional conjugation step). In some embodiments, a linker conjugated to one or more agents (e.g., therapeutic agents, imaging agents, targeting agents, triggering agents) is conjugated to one or more additional moieties including, but not limited to, a therapeutic agent, a triggering agent, an imaging agent, a triggering agent, etc. Thus, in some embodiments, the present invention provides a dendrimer (e.g., a Baker-Huang PAMAM dendrimer) with increased load capacity (e.g., increased load of therapeutic, imaging agent, etc. on the dendrimer). In some embodiments, two or more linkers (e.g., conjugated to one or a plurality of targeting agents) are conjugated to a dendrimer (e.g., a Baker-Huang PAMAM dendrimer) via the same or different linkage (e.g., covalent linkage).

Several different schemes were evaluated for generating dendrimer conjugates (e.g., Baker-Huang PAMAM dendrimer conjugates) wherein a dendrimer is conjugated to one or more linkers that comprise multiple sites for binding (e.g., covalent binding) moieties. For example, in one embodiment, a linker may comprise a chemical structure that allows, for example, conjugation of a targeting moiety and a therapeutic compound to the linker. Thus, in some embodiments, a dendrimer conjugate of the present invention (e.g., a Baker-Huang PAMAM dendrimer conjugate) permits control of the stoichiometry between targeting agent and therapeutic compound (e.g., generation of one to one ratio, two to one ratio, one to two ratio, one to three ratio etc. between targeting and therapeutic moieties).

In some embodiments, the present invention provides compositions facilitating one-step (e.g., "click chemistry") conjugation of functional groups to dendrimers (e.g., terminal arms of dendrimers). In some embodiments, such compositions comprise multifunctional small molecule architectures (e.g., scaffolds) which permit conjugation to functional groups (e.g., therapeutic groups, imaging groups, targeting groups, pro-drugs complexes, trigger groups). In some embodiments, such functional group-conjugated compositions are used for one-step conjugation to dendrimers (e.g., to terminal branches of dendrimers or modified dendrimers). In some embodiments, compositions of the present invention comprise triazine compositions. In some embodiments, a triazine composition is trifunctional such that two sites are used for conjugation or binding to functional groups (e.g., bioactive molecules) and an azide linker is conjugated (e.g., linked) to the third site. Compositions of the present invention are not limited by the numerical functionality, e.g., bifunctional, trifunctional, quadfunctional or embodiments with higher degrees of multifunctionality are contemplated.

In some embodiments, a dendrimer (e.g., a Baker-Huang dendrimer) conjugated to a linker that is conjugated to a functional group (e.g., targeting agent and/or therapeutic agent) comprises a linker that is configured to be irreversibly degraded (e.g., that is non-reversible (e.g., that permits drug delivery at the correct time and/or at the correct place)).

In some embodiments, the present invention provides dendrimer molecules (e.g., Baker-Huang dendrimers) conjugated to one or more therapeutic agents configured for controlled and/or sustained release of the therapeutic agents (e.g., through use of targeting agents, linking agents, and/or trigger agents conjugated to the dendrimer and/or therapeutic agent). In some embodiments, the therapeutic agent conjugated to the dendrimer is active upon administration to a subject. In some embodiments, sustained release (e.g., slow release over a period of 24-48 hours) of the therapeutic agent is accomplished through conjugating the therapeutic agent to the dendrimer through, for example, a linkage agent connected to a trigger agent that slowly degrades in a biological system (e.g., amide linkage, ester linkage, ether linkage). In some embodiments, constitutively active release of the therapeutic agent is accomplished through conjugating the therapeutic agent to the dendrimer through, for example, a linkage agent connected to a trigger agent that renders the therapeutic agent constitutively active in a biological system (e.g., amide linkage, ether linkage). In some embodiments, the dendrimers conjugated to one or more therapeutic agents are simultaneously configured for sustained release (e.g., a slow release mechanism that achieves therapeutic concentrations over a period of, for example, 24-48 hours) of the therapeutic agent.

In some embodiments, the dendrimer conjugates (e.g., Baker-Huang dendrimer conjugates) comprise i) a targeting agent that enables the conjugate to cross the blood-brain-barrier (BBB) and target neurons, ii) a locking agent (e.g., a re-dox locking module) to prevent the dendrimer conjugate from diffusing back across the BBB, and iii) a therapeutic agent. The dendrimer conjugates are not limited to particular targeting agents. In some embodiments, the targeting agent for CNS targeting through crossing the BBB is transferrin (see, e.g., Daniels, T. R., et al., Clinical Immunology, 2006. 121(2): p. 159-176; Daniels, T. R., et al., Clinical Immunology, 2006. 121(2): p. 144-158; each herein incorporated by reference in their entireties). In some embodiments, the targeting agent for neuron targeting is a 12 amino acid peptide (Tet 1) (see, e.g., Liu, J. K., et al., Neurobiology of Disease, 2005. 19(3): p. 407-418; herein incorporated by reference in its entirety). The dendrimer conjugates are not limited to particular locking agents. In some embodiments, the locking agent for locking the dendrimer conjugate within the CNS is the 1,4-dihydrotrigonelline↔trigonelline (coffearine) re-dox system where the lipophilic 1,4-dihydro form (L) is converted in vivo to the hydrophilic quaternary form ($L^+$) by oxidation to prevent the dendrimer conjugate from diffusing back into the circulation (see, e.g., Bodor, N. and P. Buchwald, Drug Discovery Today, 2002. 7(14): p. 766-774; herein incorporated by reference in its entirety). In some embodiments, the dendrimer conjugate device is eliminated from the CNS (e.g., because of acquired hydrophilicity due to loss of the quaternary form).

Figure 18:
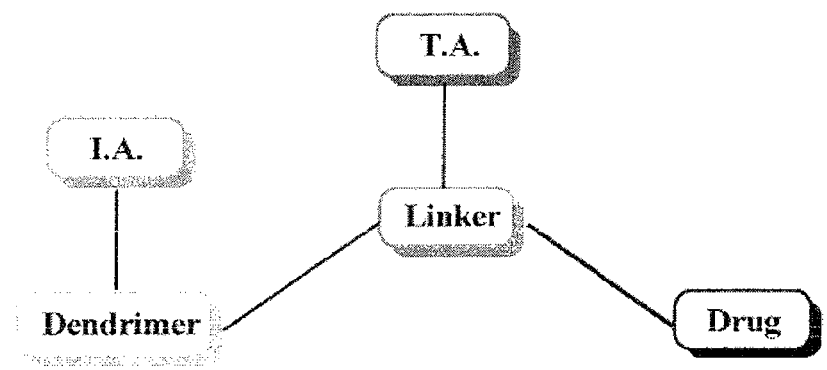
FIG. 18 shows a diagram of a dendrimer conjugate provided in some embodiments of the present invention.

In some embodiments, the present invention provides a dendrimer conjugate as shown in FIG. 18. For example, FIG. 18 shows a targeting agent (T.A.) conjugated to a linker that is also conjugated to a drug, wherein the linker conjugated to a drug and targeting agent is conjugated to a dendrimer conjugated to an imaging agent (I.A.). In some embodiments, the present invention provides a dendrimer conjugate as shown in FIG. 19 (A, B, and C) (e.g., possessing targeted anticancer therapeutic moiety). For example, FIG. 19 (A, B, and C) shows several structures of dendrimer conjugates, wherein R1, R2, R3 and R4 are each independently selected from hydrogen, halogen, and alkyl. In some embodiments, the alkyl is straight or cyclic, unsubstituted or substituted (e.g., by from 1 to 4 substituents (e.g., selected from the group comprising, but not limited to, halogen, amino, monoalkylamino, dialkylamino, hydroxy, alkoxy, nitro, aryl, cyano, carboxyl, carboxyl amide, monoalkylcarboxamide, dialkylcarboxamide, thiol, thioalkyl and sulfonic acid)). In some embodiments, the "U" moiety is present or absent. In some embodiments, when the "U" moiety is absent, one of the R1, R2, R3 and/or R4 groups is linked to a targeting agent through a linker and/or spacer. In some embodiments, R5 is an alkyl (e.g., that is straight chained, branched, cyclic (e.g., that is substituted or unsubstituted)). In some embodiments, R6 is a hydrogen or an alkyl (e.g., of 1-4 carbons (e.g., that are straight chained or cyclic (e.g., that is substituted or unsubstituted)). In some embodiments, Ra, Rb, Rc, Rd and Re are each independently selected from hydrogen, halogen, and alkyl. In some embodiments, the alkyl is straight or cyclic, unsubstituted or substituted (e.g., by from 1 to 4 substituents (e.g., selected from halogen, amino, monoalkylamino, dialkylamino, hydroxy, alkoxy, nitro, awl, cyano, carboxyl, carboxamide, monoalkylcarboxamide, dialkylcarboxamide, thiol, thioalkyl and sulfonic acid. In some embodiments, the "U" moiety is present or absent. In some embodiments, when the "U" moiety is absent, one of the Ra, Rb, Rc, Rd and Re groups is linked to a targeting agent through a linker and/or spacer. In some embodiments, "Y" is an oxygen atom. In some embodiments, "Y" is two hydrogen atoms. In some embodiments, G5 is a generation five poly (amidoamine) (PAMAM) dendrimer (e.g., Baker-Huang PAMAM dendrimer) (e.g., conjugated to one or more imaging agents (e.g., FITC, etc.), although higher (e.g., G6, G7, G8, G9, G10 or higher, or lower, G4, G3, or G2 dendrimers) may also be used.

In some embodiments, "W" is a linker comprising 1-8 carbon and/or nitrogen atoms (e.g., straight chained, branched, or cyclic, unsubstituted or substituted by "R" groups as described above.

Figure 20:
FIG. 20 shows a diagram of a dendrimer conjugate provided in some embodiments of the present invention.
Figure 21:
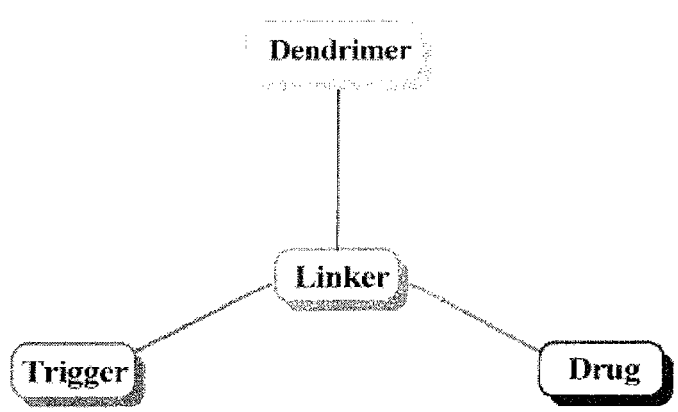
FIG. 21 shows a diagram of a dendrimer conjugate provided in some embodiments of the present invention.

In some embodiments, the present invention provides a dendrimer conjugate as shown in FIGS. 20 and 21. In particular, a dendrimer conjugate as shown in FIG. 20 comprises a dendrimer (e.g., a G5 PAMAM dendrimer conjugated to an imaging agent (e.g., FITC) and/or targeting agent) conjugated to a trigger molecule that is conjugated to a linker that is conjugated to a therapeutic. A dendrimer conjugate as shown in FIG. 21 comprises a dendrimer (e.g., a G5 PAMAM dendrimer conjugated to an imaging agent (e.g., FITC) and/or targeting agent) conjugated to a linker that is conjugated to a trigger and to a therapeutic moiety. The conjugates of FIGS. 20 and 21 are configured to be non-toxic to normal cells. For example, the conjugates are configured in such a way so as to release their therapeutic agent only at a specific, targeted site (e.g., through activation of a trigger molecule that in to leads to release of the therapeutic agent) For example, once a conjugate arrives at a target site in a subject (e.g., a tumor, or a site of inflammation), components in the target site (e.g., a tumor associated factor, or an inflammatory or pain associated factor) interacts with the trigger moiety thereby initiating cleavage of this unit from the linker. In some embodiments, once the trigger is cleaved from the linker (e.g., by a target associated moiety) the linker proceeds through spontaneous chemical breakdown thereby releasing the therapeutic agent at the target site (e.g., in its active form). The present invention is not limited to any particular target associated moiety (e.g., that interacts with and initiates cleavage of a trigger). In some embodiments, the target associated moiety is a tumor associated factor (e.g., an enzyme (e.g., glucuronidase and/or plasmin), a cathepsin, a matrix metalloproteinase, a hormone receptor (e.g., integrin receptor, hyaluronic acid receptor, luteinizing hormone-releasing hormone receptor, etc.), cancer and/or tumor specific DNA sequence), an inflammatory associated factor (e.g., chemokine, cytokine, etc.) or other moiety.

Figure 22:
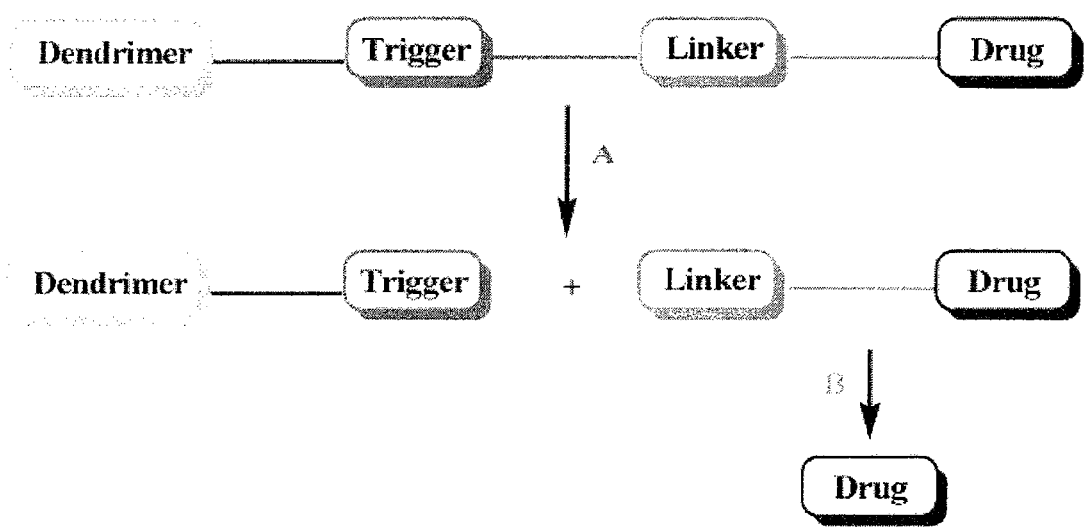
FIG. 22 shows a diagram of a dendrimer conjugate provided in some embodiments of the present invention.
Figure 24:
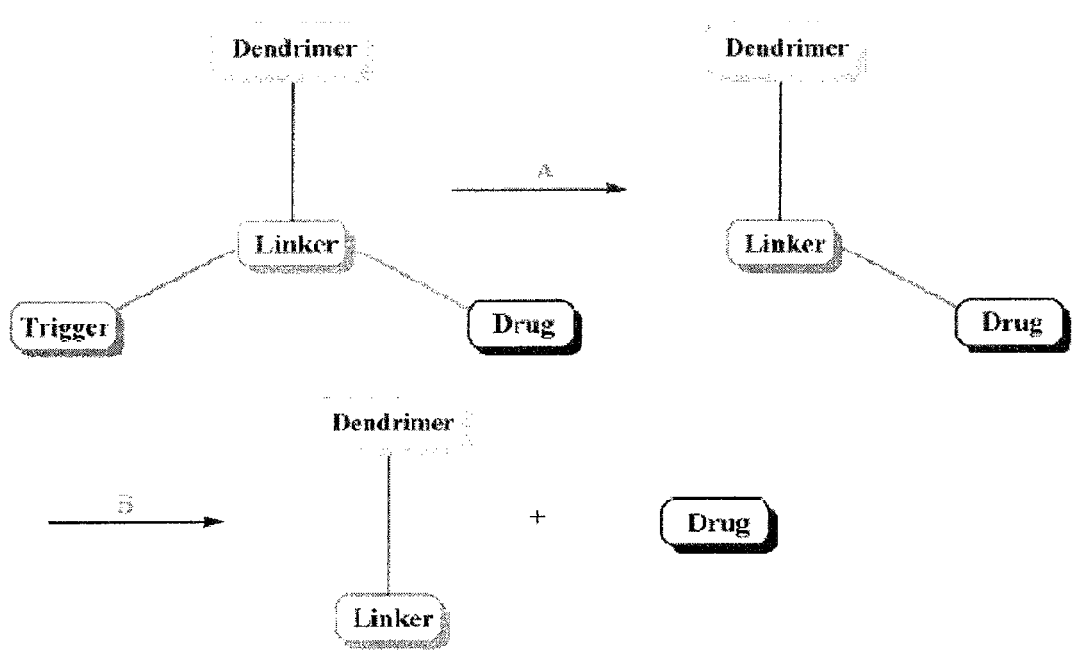
FIG. 24 shows a diagram of a dendrimer conjugate provided in some embodiments of the present invention.
Figure 25:
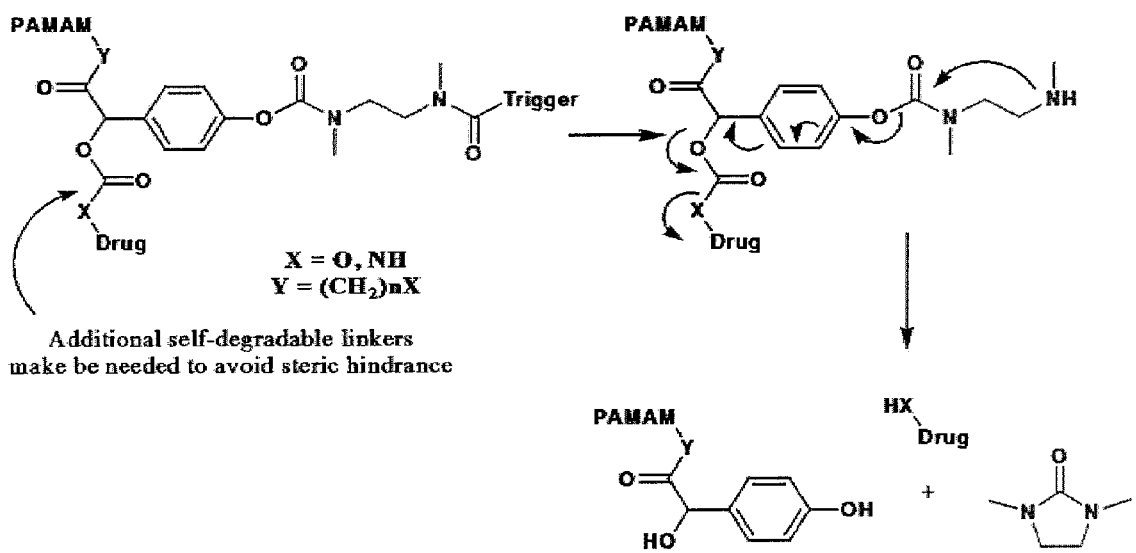
FIG. 25 shows the release of a therapeutic compound from a dendrimer conjugate in one embodiment of the invention.
Figure 26:
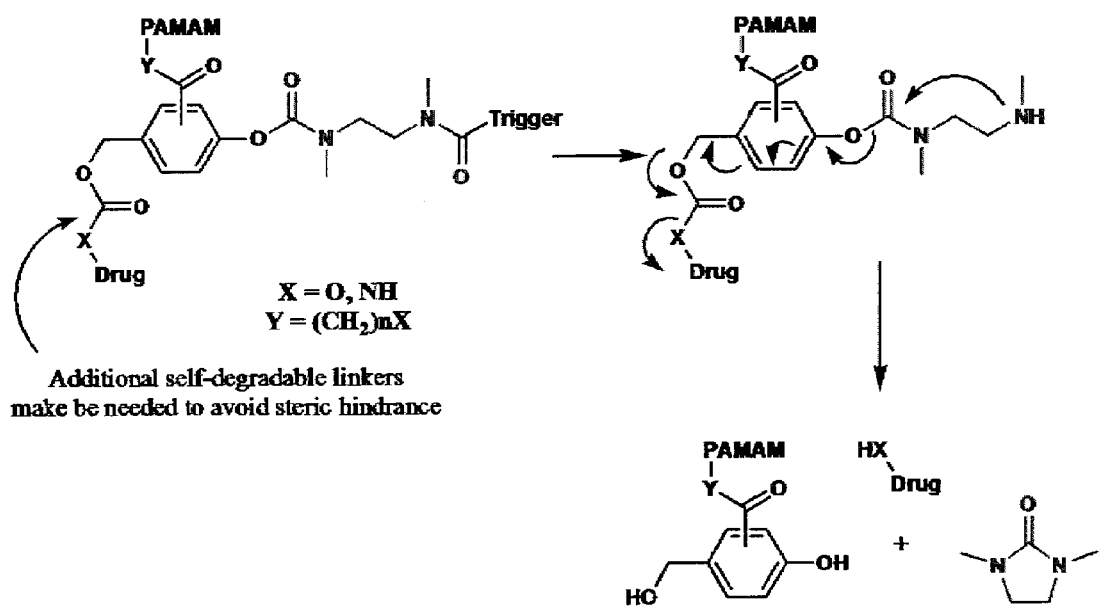
FIG. 26 shows the release of a therapeutic compound from a dendrimer conjugate in one embodiment of the invention.
Figure 28:
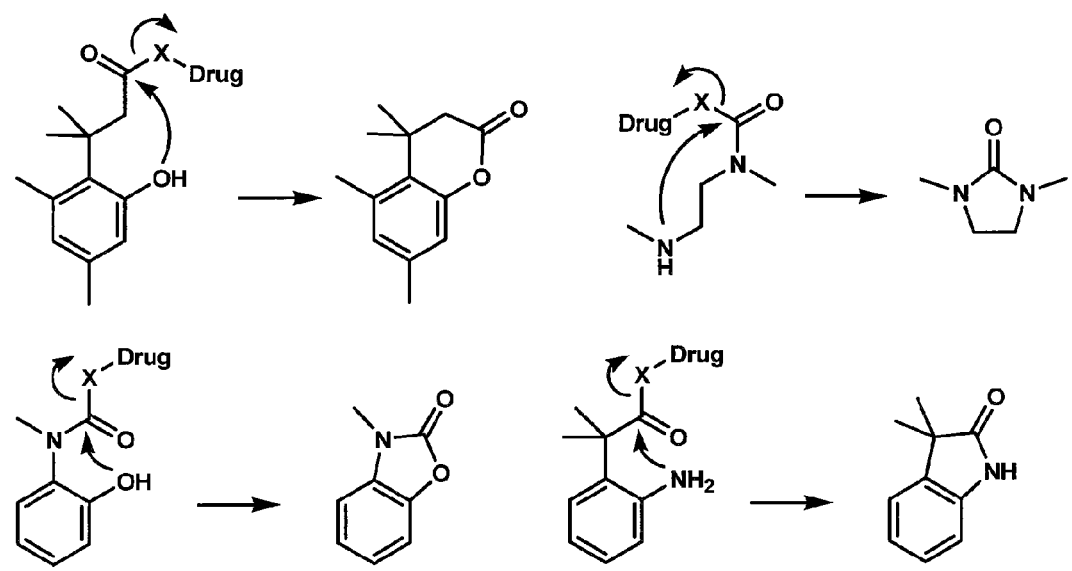
FIG. 28 depicts cyclization based linkers in some embodiments of the invention.

Although an understanding of a mechanism of action is not necessary to practice the present invention, and the present invention is not limited to any particular mechanism of action, in some embodiments, a dendrimer conjugate as described in FIG. 20 or 21 provides a therapeutic to a site by a mechanism as shown in FIG. 22 or 24. For example, as shown in FIG. 22, a dendrimer conjugate comprising a dendrimer (e.g., a G5 PAMAM dendrimer (e.g., a Baker-Huang PAMAM dendrimer) conjugated to an imaging agent (e.g., FITC) and/or targeting agent) conjugated to a trigger molecule that is conjugated to a linker that is conjugated to a therapeutic (A) interacts with a target associated moiety thereby activating the trigger and initiating cleavage of same, releasing the linker therapeutic drug conjugate. Once cleavage of the trigger occurs, the linker (B) proceeds through a spontaneous chemical breakdown at the target site, releasing (e.g., irreversibly releasing) the therapeutic drug at the target site. In some embodiments, as shown in FIG. 24, a dendrimer conjugate comprising a dendrimer (e.g., a G5 PAMAM dendrimer (e.g., Baker-Huang dendrimer) conjugated to an imaging agent (e.g., FITC) and/or targeting agent) conjugated to a linker that is conjugated to a trigger and to a therapeutic moiety (A) interacts with a target associated moiety thereby activating the trigger and initiating cleavage of same, releasing a dendrimer-linker-therapeutic moiety from the trigger. Once cleavage of the trigger occurs, the linker (B) proceeds through a spontaneous chemical breakdown (e.g., to a point where the therapeutic drug is released from the dendrimer linker conjugate) at the target site, releasing (e.g., irreversibly releasing) the therapeutic drug at the target site. In some embodiments, cleavage of the trigger and subsequent linker breakdown is not necessary to deliver the therapeutic drug to the target site. Several design processes for generating a dendrimer conjugate comprising a trigger are shown in FIGS. 25 and 28. In some embodiments, one or more amino groups present on the dendrimer are linked (e.g., through a covalent bond) to one or more targeting agents (e.g., folic acid) and/or imaging agents (e.g., FITC) (e.g., as described in U.S. Pat. Nos. 6,471,968 and 7,078,461; U.S. Patent Pub. Nos. 20020165179 and 20070041934 and WO 06/033766, each of which is hereby incorporated by reference in its entirety for all purposes).

In some embodiments, the present invention provides a dendrimer conjugate as shown in FIG. 23 (A, B, C and D). In particular, a dendrimer conjugate as shown in FIG. 23 (A, B, C and D) comprises a dendrimer (e.g., a G5 Baker-Huang PAMAM dendrimer conjugated to an imaging agent (e.g., FITC) and/or targeting agent) conjugated to a trigger molecule that is conjugated to a linker that is conjugated to a therapeutic, or a dendrimer (e.g., a G5 PAMAM dendrimer conjugated to an imaging agent (e.g., FITC) and/or targeting agent) conjugated to a linker that is conjugated to a trigger and to a therapeutic moiety). For example, FIG. 23 (A, B, C and D) shows several structures of dendrimer conjugates, wherein R1, R2, R3 and R4 are each independently selected from hydrogen, halogen, and alkyl. In some embodiments, the alkyl is straight or cyclic, unsubstituted or substituted (e.g., by from 1 to 4 substituents (e.g., selected from the group comprising, but not limited to, halogen, amino, monoalkylamino, dialkylamino, hydroxy, alkoxy, nitro, aryl, cyano, carboxyl, carboxamide, monoalkylcarboxamide, dialkylcarboxamide, thiol, thioalkyl and sulfonic acid. In some embodiments, R5 is an alkyl that is straight, branched or cyclic, that is unsubstituted or substituted. In some embodiments, R6 is a hydrogen or alkyl of 1-4 carbons that are straight, branched or cyclic, that is unsubstituted or substituted. In some embodiments, the two R6 are connected together to form a ring of 3o6 members. In some embodiments, R', R'', R''' and R'''' are each independently selected from hydrogen, halogen, and alkyl. In some embodiments, the alkyl is straight or cyclic, unsubstituted or substituted (e.g., by from 1 to 4 substituents (e.g., selected from the group comprising, but not limited to, halogen, amino, monoalkylamino, dialkylamino, hydroxy, alkoxy, nitro, aryl, cyano, carboxyl, carboxamide, monoalkylcarboxamide, dialkylcarboxamide, thiol, thioalkyl and sulfonic acid. In some embodiments, X, X2 and X3 are either oxygen or "NR", wherein "N" is a nitrogen atom, and "R" is an alkyl that is straight or branched or cyclic (e.g., substituted or unsubstituted). In some embodiments, "Y" is an oxygen atom or two hydrogen atoms. In some embodiments, A-B is an ethylene group (e.g., unsubstituted or substituted by alkyls (e.g., straight or cyclic). In some embodiments, A-B are connected by a carbon chain (e.g., of 2, 3, 4, 5, or more carbons) and/or hetero atoms (e.g., forming a saturated or unsaturated aromatic ring structure (e.g., comprising substituents such as R1, R2, R3 and R4). In some embodiments, G5 is a dendrimer (e.g., a G5 PAMAM dendrimer conjugated to an imaging agent (e.g., FITC) and/or targeting agent). As described herein, the present invention is not limited to any particular dendrimer. In some embodiments, "W" is a linker (e.g., comprising a carbon or nitrogen chain (e.g., 2, 3, 4, 5, 6, 7, 8, 9, or more carbons or nitrogens (e.g., straight or branched or cyclic (e.g., substituted or unsubstituted (e.g., with R groups as described above))).

The present invention is not limited by the type of dendrimer conjugate (e.g., comprising a trigger) for use in treating a subject. In some embodiments, the dendrimer conjugates (e.g., Baker-Huang PAMAM dendrimer conjugates) of the present invention are used as delivery agents for therapeutic agents and therapeutic agent antagonists. Such dendrimer conjugates are not limited to uses within particular settings. Indeed, the dendrimer conjugates of the present invention may be used in any setting requiring treatment (e.g., battlefield, ambulance, hospital, clinic, rescue, etc.). In addition, the present invention contemplates dendrimer conjugates comprising one or more therapeutic agent prodrugs and/or therapeutic agent antagonist prodrugs developed for site specific conversion to drug based on tumor associated factors (e.g., hypoxia and pH, tumor-associated enzymes, and/or receptors). In some embodiments, dendrimer conjugates of the present invention are configured such that a prodrug (e.g., therapeutic agent prodrug, therapeutic agent antagonist prodrug) is conjugated to a linker that is further conjugated to a targeting moiety (e.g., that targets the conjugate to a particular body region (e.g., CNS)). Although an understanding of the mechanism is not necessary for the present invention, and the present invention is not limited to any particular mechanism of action, in some embodiments, a trigger component serves as a precursor for site-specific activation. For example, in some embodiments, once the trigger recognizes a particular condition (e.g., hypoxia), cleavage and/or processing of the trigger is induced, thereby releasing the therapeutic agent and/or therapeutic antagonist.

In some embodiments, the present invention provides a dendrimer conjugate comprising a linker that connects to a therapeutic compound. In some embodiments, the linker is configured such that its decomposition leads to the liberation (e.g., non-reversible liberation) of the therapeutic agent (e.g., at the target site (e.g., site of tumor, CNS, and/or inflammatory site)). The linker may influence multiple characteristics of a dendrimer conjugate including, but not limited to, properties of the therapeutic agent (e.g., stability, pharmacokinetic, organ distribution, bioavailability, and/or enzyme recognition (e.g., when the therapeutic agent (e.g., prodrug)) is enzymatically activated)).

In some embodiments, the linker is an elimination linker. For example, in some embodiments, in a dendrimer conjugate of the present invention (e.g., a Baker-Huang PAMAM dendrimer conjugate), when a trigger is cleaved (e.g., enzymatically and/or chemically), a phenol or an aniline promotes a facile 1,4 or 1,6 elimination, followed by release of a $CO_2$ molecule and the unmasked therapeutic agent (e.g., drug). In some embodiments, a dendrimer conjugate of the present invention utilizes this configuration and/or strategy to mask one or more hydroxyl groups and/or amino groups of the therapeutic agents. In some embodiments, a linker present within a dendrimer conjugate of the present invention is fine tuned (e.g., to optimize stability and/or drug release from the conjugate). For example, the sizes of the aromatic substituents can be altered (e.g., increased or decreased) and/or alkyl substitutions at the benzylic position may be made to alter (e.g., increase or decrease) degradation of the linker and/or release of the therapeutic agent (e.g., prodrug). In some embodiments, elongated analogs (e.g., double spacers) are used (e.g., to decrease steric hindrance (e.g., for large therapeutic agents)). In some embodiments, a dendrimer conjugate of the present invention comprises an enol based linker (e.g., that undergoes an elimination reaction to release therapeutic agent (e.g., prodrug)).

Figure 27:
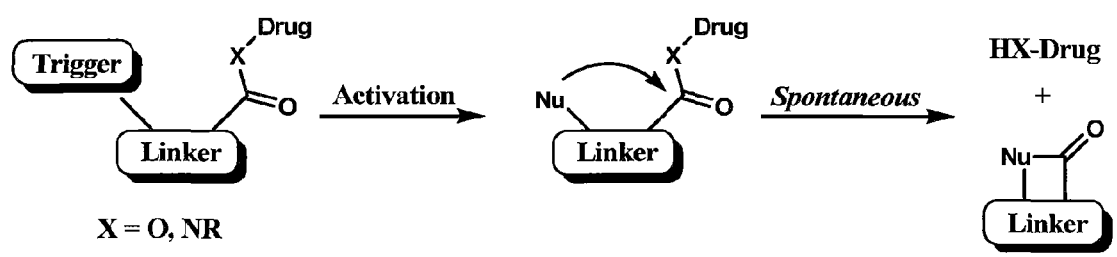
FIG. 27 depicts a dendrimer conjugate comprising a cyclization based linker in some embodiments of the present invention.

In some embodiments, the linker is a cyclization based linker. For example, one configuration for this approach is shown in FIG. 27. A nucleophilic group (e.g., OH or NHR) that becomes available once the trigger is cleaved attacks the carbonyl of the C(O)X— Therapeutic agent/drug (e.g., thereby leading to release of therapeutic agent-XH) and thereby to quickly release the Drug-XH. In some embodiments, a driving force that permits the reaction to reach completion is the stability of the cyclic product. In some embodiments, a cyclization based linker of a dendrimer conjugate of the present invention include, but are not limited to, those shown in FIG. 28.

Figure 29:
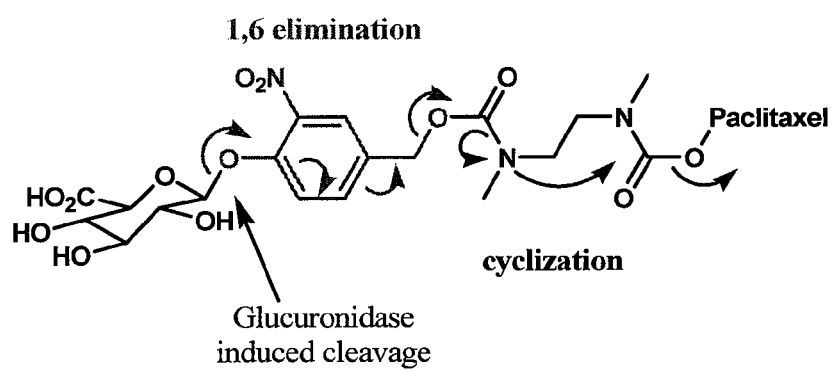
FIG. 29 depicts a linker utilized in a dendrimer conjugate in some embodiments of the present invention.

In some embodiments, a dendrimer conjugate (e.g., a Baker-Huang PAMAM dendrimer conjugate) of the present invention comprises a combination of one or more linkers. For example, in some embodiments, a dendrimer conjugate comprises a combination of two or more elimination linkers. In some embodiments, a dendrimer conjugate of the present invention comprises two or more cyclization linkers. In some embodiments, a dendrimer conjugate of the present invention comprises a one or more elimination linkers and one or more cyclization linkers, or a combination of one or more different types of linkers described herein. For example, in some embodiments, a dendrimer conjugate comprises a linker as shown in FIG. 29.

Figure 30:
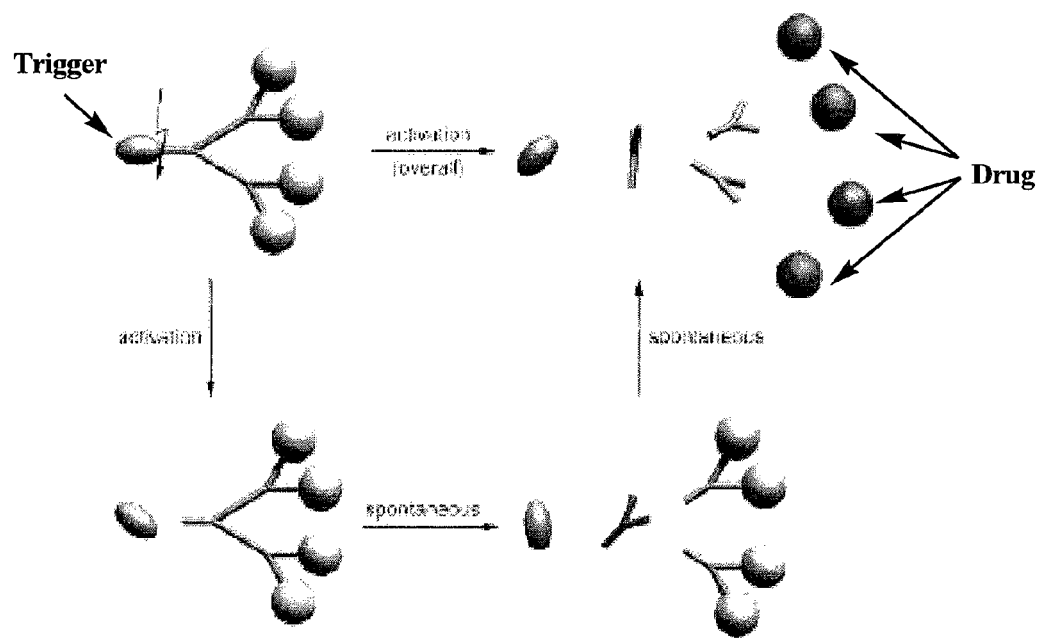
FIG. 30 shows branched self-elimination linkers utilized in a dendrimer conjugate in some embodiments of the present invention.

In some embodiments, a dendrimer conjugate of the present invention comprises branched self-elimination linkers (e.g., as shown in FIG. 30). Thus, in some embodiments, use of branched linkers provides a conjugate that can present increased concentrations of a therapeutic agent to a target site (e.g., inflammatory site, tumor site, etc.).

In some embodiments, a dendrimer conjugate of the present invention is generated by a process comprising conjugating a pre-formed tripartite piece (e.g., trigger, linker, and therapeutic agent) to a dendrimer (e.g., a G5 Baker-Huang PAMAM dendrimer (e.g., conjugated to one or more different types of agents (e.g., imaging agent)). In some embodiments, linkage between a tripartite piece and a dendrimer comprises a non-cleavable bond (e.g., an ether or an amide bond (e.g., thereby decreasing unwanted activation of a trigger and/or degradation of a linker and/or release of therapeutic drug). In some embodiments, a linker (e.g., linear or other type of linker described herein) is utilized to attach a tripartite moiety (e.g., trigger, linker, and therapeutic agent) to a dendrimer (e.g., in order to increase drug release, decrease steric hindrance, and/or increase stability of the dendrimer). For example, in some embodiments, the present invention provides a dendrimer conjugate as shown in FIG. 31A-B.

In some embodiments, a dendrimer conjugate of the present invention (e.g., a Baker-Huang PAMAM dendrimer conjugate) comprises a dendrimer conjugated to a linker (e.g., optionally conjugated to a trigger) that is conjugated to a therapeutic agent. In some embodiments, the dendrimer conjugate comprises a self-immolative connector between an ester bond (e.g., that is to be cleaved) and the therapeutic agent (e.g., thereby enhancing drug release). For example, although a mechanism is not necessary to practice the present invention and the present invention is not limited to any particular mechanism of action, in some embodiments, a dendrimer conjugate of the present invention comprising an ester linkage undergoes esterase catalyzed hydrolysis (e.g., as shown in FIG. 32 (e.g., G5 dendrimer comprising a self-degradable spacer and therapeutic agent)). Thus, in contrast to a dendrimer comprising a simple ester (e.g., a dendrimer in the top portion of FIG. 32 wherein therapeutic agent release may or may not occur, e.g., if x=NH), in some embodiments, the present invention provides a dendrimer conjugate comprising an elimination linker (e.g., a 1,6, elimination linker/ spacer as shown in the bottom portion of FIG. 32 (e.g., that permits complete hydrolysis of the linker (e.g., at a target site))).

The present invention is not limited by the type of linker configuration. In some embodiments, the linker is conjugated via a free amino group via an amide linkage (e.g., formed from an active ester (e.g., the N-hydroxysuccinimide ester)). In some embodiments, an ester linkage remains in the conjugate after conjugation. In some embodiments, linkage occurs through a lysine residue. In some embodiments, conjugation occurs through a short-acting, degradable linkage. The present invention is not limited by the type of degradable linkage utilized. Indeed, a variety of linkages are contemplated to be useful in the present invention including, but not limited to, physiologically cleavable linkages including ester, carbonate ester, carbamate, sulfate, phosphate, acyloxyalkyl ether, acetal, and ketal linkages. In some embodiments, a dendrimer conjugate comprises a cleavable linkage present in the linkage between the dendrimer and linker and/or targeting agent and/or therapeutic agent present therein (e.g., such that when cleaved, no portion of the linkage remains on the dendrimer). In some embodiments, a dendrimer conjugate comprises a cleavable linkage present in the linker itself (e.g., such that when cleaved, a small portion of the linkage remains on the dendrimer).

The present invention is not limited to a particular trigger agent or to any particular cleavage and/or processing of the trigger agent. In some embodiments, the present invention provides therapeutic agents and/or therapeutic agent antagonists coupled to dendrimers with a linkage agent connected to a trigger agent that slowly degrades in a biological system (e.g., amide linkage, ester linkage, ether linkage).

In some embodiments, the present invention provides a dendrimer conjugate comprising a trigger agent that is sensitive to (e.g., is cleaved by) hypoxia. Hypoxia is a feature of several disease states, including cancer, inflammation and rheumatoid arthritis, as well as an indicator of respiratory depression (e.g., resulting from analgesic drugs). Advances in the chemistry of bioreductive drug activation have led to the design of various hypoxia-selective drug delivery systems in which the pharmacophores of drugs are masked by reductively cleaved groups. In some embodiments, a dendrimer conjugate of the present invention (e.g., a Baker-Huang PAMAM dendrimer conjugate) utilizes a quinone, N-oxide and/or (hetero)aromatic nitro groups. For example, a quinone present in a dendrimer conjugate of the present invention is reduced to phenol under hypoxia conditions, with spontaneous formation of lactone that serves as a driving force for drug release. In some embodiments, a heteroaromatic nitro compound present in a dendrimer conjugate of the present invention is reduced to either an amine or a hydroxylamine, thereby triggering the spontaneous release of a therapeutic agent/ drug. In some embodiments, the present invention provides therapeutic agents and/or therapeutic agent antagonists coupled to dendrimers with a linkage agent connected to a trigger agent that degrades upon detection of reduced pO2 concentrations (e.g., through use of a re-dox linker).

The concept of prodrug systems in which the pharmacophores of drugs are masked by reductively cleavable groups has been widely explored by many research groups and pharmaceutical companies (see, e.g., Beall, H. D., et al., Journal of Medicinal Chemistry, 1998. 41(24): p. 4755-4766; Ferrer, S., D. P. Naughton, and M. D. Threadgill, Tetrahedron, 2003. 59(19): p. 3445-3454; Naylor, M. A., et al., Journal of Medicinal Chemistry, 1997. 40(15): p. 2335-2346; Phillips, R. M., et al., Journal of Medicinal Chemistry, 1999. 42(20): p. 4071-4080; Zhang, Z., et al., Organic & Biomolecular Chemistry, 2005. 3(10): p. 1905-1910; each of which are herein incorporated by reference in their entireties). Several such hypoxia activated prodrugs have been advanced to clinical investigations, and work in relevant oxygen concentrations to prevent cerebral damage. The present invention is not limited to particular hypoxia activated trigger agents. In some embodiments, the hypoxia activated trigger agents include, but are not limited to, indoquinones, nitroimidazoles, and nitroheterocycles (see, e.g., Damen, E. W. P., et al., Bioorganic & Medicinal Chemistry, 2002. 10(1): p. 71-77; Hay, M. P., et al., Journal of Medicinal Chemistry, 2003. 46(25): p. 5533-5545; Hay, M. P., et al., Journal of the Chemical Society-Perkin Transactions 1, 1999(19): p. 2759-2770; each herein incorporated by reference in their entireties).

In some embodiments, the present invention provides a dendrimer conjugate (e.g., a Baker-Huang dendrimer conjugate) comprising a trigger agent that is sensitive to (e.g., is cleaved by) and/or that associates with a tumor associated enzyme. In some embodiments, the present invention provides a dendrimer conjugate comprising a trigger that is sensitive to (e.g., is cleaved by) and/or that associates with a glucuronidase. Glucuronic acid can be attached to several anticancer drugs via various linkers. These anticancer drugs include, but are not limited to, doxorubicin, paclitaxel, docetaxel, 5-fluorouracil, 9-aminocamptothecin, as well as other drugs under development. These prodrugs are generally stable at physiological pH and are significantly less toxic than the parent drugs. In some embodiments, dendrimer conjugates comprising anticancer prodrugs find use for treating necrotic tumors (e.g., that liberate β-glucuronidase) or for ADEPT with antibodies that can deliver β-glucuronidase to target tumor cells.

In some embodiments, the present invention provides a dendrimer conjugate comprising a trigger agent that is sensitive to (e.g., is cleaved by) and/or that associates with brain enzymes. For example, trigger agents such as indolequinone are reduced by brain enzymes such as, for example, diaphorase (see, e.g., Damen, E. W. P., et al., Bioorganic & Medicinal Chemistry, 2002. 10(1): p. 71-77; herein incorporated by reference in its entirety). For example, in such embodiments, the antagonist is only active when released during hypoxia to prevent respiratory failure.

In some embodiments, the present invention provides a dendrimer conjugate comprising a trigger agent that is sensitive to (e.g., is cleaved by) and/or that associates with a protease. The present invention is not limited to any particular protease. In some embodiments, the protease is a cathepsin. In some embodiments, a trigger comprises a Lys-Phe-PABC moiety (e.g., that acts as a trigger). In some embodiments, a Lys-Phe-PABC moiety linked to doxorubicin, mitomycin C, and paclitaxel are utilized as a trigger-therapeutic conjugate in a dendrimer conjugate provided herein (e.g., that serve as substrates for lysosomal cathepsin B or other proteases expressed (e.g., overexpressed) in tumor cells. In some embodiments, utilization of a 1,6-elimination spacer/linker is utilized (e.g., to permit release of therapeutic drug post activation of trigger).

In some embodiments, the present invention provides a dendrimer conjugate comprising a trigger agent that is sensitive to (e.g., is cleaved by) and/or that associates with plasmin. The serine protease plasmin is over expressed in many human tumor tissues. Tripeptide specifiers (e.g., including, but not limited to, Val-Leu-Lys) have been identified and linked to anticancer drugs through elimination or cyclization linkers.

In some embodiments, the present invention provides a dendrimer conjugate comprising a trigger agent that is sensitive to (e.g., is cleaved by) and/or that associates with a matrix metalloproteases (MMPs). In some embodiments, the present invention provides a dendrimer conjugate comprising a trigger that is sensitive to (e.g., is cleaved by) and/or that associates with β-Lactamase (e.g., a β-Lactamase activated cephalosporin-based prodrug).

In some embodiments, the present invention provides a dendrimer conjugate comprising a trigger agent that is sensitive to (e.g., is cleaved by) and/or activated by a receptor (e.g., expressed on a target cell (e.g., a tumor cell)). Thus, in some embodiments, a dendrimer conjugate comprises a receptor binding motif conjugated to a therapeutic agent (e.g., cytotoxic drug) thereby providing target specificity. Examples include, but are not limited to, a dendrimer conjugate comprising a prodrug (e.g., of doxorubicin and/or paclitaxel) targeting integrin receptor, a hyaluronic acid receptor, and/or a hormone receptor In some embodiments, the present invention provides a dendrimer conjugate comprising a trigger agent that is sensitive to (e.g., is cleaved by) and/or activated by a nucleic acid. Nucleic acid triggered catalytic drug release can be utilized in the design of chemotherapeutic agents. Thus, in some embodiments, disease specific nucleic acid sequence is utilized as a drug releasing enzyme-like catalyst (e.g., via complex formation with a complimentary catalyst-bearing nucleic acid and/or analog). In some embodiments, the release of a therapeutic agent is facilitated by the therapeutic component being attached to a labile protecting group, such as, for example, cisplatin or methotrexate being attached to a photolabile protecting group that becomes released by laser light directed at cells emitting a color of fluorescence (e.g., in addition to and/or in place of target activated activation of a trigger component of a dendrimer conjugate). In some embodiments, the therapeutic device also may have a component to monitor the response of the tumor to therapy. For example, where a therapeutic agent of the dendrimer induces apoptosis of a target cell (e.g., a cancer cell (e.g., a prostate cancer cell)), the caspase activity of the cells may be used to activate a green fluorescence. This allows apoptotic cells to turn orange, (combination of red and green) while residual cells remain red. Any normal cells that are induced to undergo apoptosis in collateral damage fluoresce green.

The present invention is not limited to the use of particular therapeutic agents. In some embodiments, the therapeutic agents are effective in treating autoimmune disorders and/or inflammatory disorders (e.g., arthritis). Examples of such therapeutic agents include, but are not limited to, disease-modifying antirheumatic drugs (e.g., leflunomide, methotrexate, sulfasalazine, hydroxychloroquine), biologic agents (e.g., rituximab, infliximab, etanercept, adalimumab, golimumab), nonsteroidal anti-inflammatory drugs (e.g., ibuprofen, celecoxib, ketoprofen, naproxen, piroxicam, diclofenac), analgesics (e.g., acetaminophen, tramadol), immunomodulators (e.g., anakinra, abatacept), glucocorticoids (e.g., prednisone, methylprednisone), TNF-α inhibitors (e.g., adalimumab, certolizumab pegol, etanercept, golimumab, infliximab), IL-1 inhibitors, and metalloprotease inhibitors. In some embodiments, the therapeutic agents include, but are not limited to, infliximab, adalimumab, etanercept, parenteral gold or oral gold.

In some embodiments, the therapeutic agents are effective in treating cancer (see, e.g., U.S. Pat. Nos. 6,471,968, 7,078, 461; U.S. patent application Ser. Nos. 09/940,243, 10/431, 682, 11/503,742, 11,661,465, 11/523,509, 12/403,179, 12/106,876, 11/827,637, 10/039,393, 10/254,126, 09/867, 924, 12/570,977, and Ser. No. 12/645,081; U.S. Provisional Patent Application Ser. Nos. 61/140,480, 61/091,608, 61/097,780, 61/101,461, 60/604,321, 60/690,652, 60/707,991, 60/208,728, 60/718,448, 61/035,949, 60/830,237, and 60/925,181; and International Patent Application Nos. PCT/US2010/050893, PCT/US2010/042556, PCT/US2001/015204, PCT/US2005/030278, PCT/US2009/069257, PCT/US2009/036992, PCT/US2009/059071, PCT/US2007/015976, and PCT/US2008/061023; each herein incorporated by reference in their entireties).

In some embodiments of the present invention, the therapeutic agent includes, but is not limited to, a chemotherapeutic agent, an anti-oncogenic agent, an anti-angiogenic agent, a tumor suppressor agent, an anti-microbial agent, or an expression construct comprising a nucleic acid encoding a therapeutic protein, although the present invention is not limited by the nature of the therapeutic agent. In further embodiments, the therapeutic agent is protected with a protecting group selected from photo-labile, radio-labile, and enzyme-labile protecting groups. In some embodiments, the chemotherapeutic agent is selected from a group consisting of, but not limited to, platinum complex, verapamil, podophylltoxin, carboplatin, procarbazine, mechloroethamine, cyclophosphamide, camptothecin, ifosfamide, melphalan, chlorambucil, bisulfan, nitrosurea, adriamycin, dactinomycin, daunorubicin, doxorubicin, bleomycin, plicomycin, mitomycin, bleomycin, etoposide, tamoxifen, paclitaxel, taxol, trans-platinum, 5-fluorouracil, vincristin, vinblastin, bisphosphonate (e.g., CB3717), chemotherapeutic agents with high affinity for folic acid receptors, ALIMTA (Eli Lilly), and methotrexate. In some embodiments, the anti-oncogenic agent comprises an antisense nucleic acid (e.g., RNA, molecule). In certain embodiments, the antisense nucleic acid comprises a sequence complementary to an RNA of an oncogene. In preferred embodiments, the oncogene includes, but is not limited to, abl, Bcl-2, Bcl-xL, erb, fms, gsp, hst, jun, myc, neu, raf; ras, ret, src, or trk. In some embodiments, the nucleic acid encoding a therapeutic protein encodes a factor including, but not limited to, a tumor suppressor, cytokine, receptor, inducer of apoptosis, or differentiating agent. In preferred embodiments, the tumor suppressor includes, but is not limited to, BRCA1, BRCA2, C-CAM, p16, p21, p53, p73, Rb, and p27. In preferred embodiments, the cytokine includes, but is not limited to, GMCSF, IL-1, IL-2, IL-3, IL-4, IL-5, IL-6, IL-7, IL-8, IL-9, IL-10, IL-11, IL-12, IL-13, IL-14, IL-15, β-interferon, γ-interferon, and TNF. In preferred embodiments, the receptor includes, but is not limited to, CFTR, EGFR, estrogen receptor, IL-2 receptor, and VEGFR. In preferred embodiments, the inducer of apoptosis includes, but is not limited to, AdE1B, Bad, Bak, Bax, Bid, Bik, Bim, Harakid, and ICE-CED3 protease. In some embodiments, the therapeutic agent comprises a short-half life radioisotope.

Dendrimer conjugates of the present invention are not limited by the type of anti-angiogenic agent used. Indeed, a variety of anti-angiogenic agents are contemplated to be useful in the compositions of the present invention including, but not limited to, Batimastat, Marimastat, AG3340, Neovastat, PEX, TIMP-1, -2, -3, -4, PAI-1, -2, uPA Ab, uPAR Ab, Amiloride, Minocycline, tetracyclines, steroids, cartilage-derived TIMP, αvβ3 Ab: LM609 and Vitaxin, RGD containing peptides, αvβ5 Ab, Endostatin, Angiostatin, aaAT, IFN-α, IFN-γ, IL-12, nitric oxide synthase inhibitors, TSP-1, TNP-470, Combretastatin A4, Thalidomide, Linomide, IFN-α, PF-4, prolactin fragment, Suramin and analogues, PPS, distamycin A analogues, FGF-2 Ab, antisense-FGF-2, Protamine, SU5416, soluble Flt-1, dominant-negative Flk-1, VEGF receptor ribosymes, VEGF Ab, Aspirin, NS-398, 6-AT, 6A5BU, 7-DX, Genistein, Lavendustin A, Ang-2, bati-mastat, marimastat, anti-αvβ3 monoclonal antibody (LM609) thrombospondin-1 (TSP-1) Angiostatin, endostatin, TNP-470, Combretastatin A-4, Anti-VEGF antibodies, soluble Flk-1, Flt-1 receptors, inhibitors of tyrosine kinase receptors, SU5416, heparin-binding growth factors, pentosan polysulfate, platelet-derived endothelial cell growth factor/Thymidine phosphorylase (PD-ECGF/TP), cox (e.g., cox-1 an cox-2) inhibitors (e.g., Celebrex and Vioxx), DT385, Tissue inhibitor of metalloprotease (TIMP-1, TIMP-2), Zinc, Plasminogen activator-inhibitor-1 (PAI-1), p53 Rb, Interleukin-10 Interleukin-12, Angiopoietin-2, Angiotensin, Angiotensin II (AT2 receptor), Caveolin-1, caveolin-2, Angiopoietin-2, Angiotensin, Angiotensin II (AT2 receptor), Caveolin-1, caveolin-2, Endostatin, Interferon-alpha, Isoflavones, Platelet factor-4, Prolactin (16 Kd fragment), Thrombospondin, Troponin-1, Bay 12-9566, AG3340, CGS 27023A, CGS 27023A, COL-3, (Neovastat), BMS-275291, Penicillamine, TNP-470 (fumagillin derivative), Squalamine, Combretastatin, Endostatin, Penicillamine, Farnesyl Transferase Inhibitor (FTI), -L-778,123, —SCH66336, —R115777, anti-VEGF antibody, Thalidomide, SU5416, Ribozyme, Angiozyme, SU6668, PTK787/ZK22584, Interferon-alpha, Interferon-alpha, Suramin, Vitaxin, EMD121974, Penicillamine, Tetrathiomolybdate, Captopril, serine protease inhibitors, CAI, ABT-627, CM101/ZDO101, Interleukin-12, IM862, PNU-145156E, those described in U.S. Patent App. No. 20050123605, herein incorporated by reference in its entirety, and fragments or portions of the above that retain anti-angiogenic (e.g., angiostatic or inhibitory properties).

In some embodiments, the therapeutic agent is a pain relief agent. The dendrimer conjugates of the present invention are not limited to a particular type or kind of pain relief agent.

In some embodiments, the pain relief agents include several medications that have been used for field deployment and have a proven efficacy for military medical applications (see, e.g., Emergency war surgery. 3rd ed. 2004, Department of Defense, USA; herein incorporated by reference in its entirety) (see Table 2). These drugs include, but are not limited to, Ketamine, narcotics (e.g., Morphine, fentanyl, hydromorphone), benzodiazepines (e.g., midazolam, diazepam, Lorazepam) and the selective antagonist of narcotics (e.g., Naloxone) and benzodiazepines (e.g., flumazenil). Military relevance is supported by the fact, for example, that small amounts of Morphine and Ketamine are used by medics during extraction-evacuation of the injured from the battle field.

TABLE 2

Drug Levels to Target Per 12-Hour Period

| Drug | Infusion | Per Hour Delivery | 12-hour Coverage |
|---|---|---|---|
| Ketamine | 1 mg/kg/hr will provide analgesia and anesthesia. | 1 mg × 75 kg => 75 mg/hr release | 900 mg |
| Lorazepam | 50 μg/kg/hr for sedation | 50 μg × 75 = 3750 μg/hr or 3.75 mg/hr release | 45000 μg (45 mg) |
| Morphine | 30 μg/kg/hr provides "basal—low end" analgesia | 30 μg × 75 kg is 2250 μg/hr released | 27000 μg (27 mg) |
| Naloxone | 5 μg/k/hr provides basal reversal of narcotic induced side effects | 5 μg × 75 kg is 375 μg/hr released | 9000 μg (9 mg) |
| Doxapram | 2 (to 3) mg/kg/hr | 2 mg × 75 kg is 150 mg/hr released | 1800 mg |

μg = Micrograms Reference: Micromedex 2006. Assumptions: Requirements for a 75 Kg individual over a 12 hours period; delivered in one subcutaneous or intramuscular administration of maximal volume 5 ml.

In some embodiments, the pain relief agent is Ketamine. Ketamine is a potent analgesic, amnestic and anxiolytic, even in the low dose range while amnesia extends beyond its analgesic duration. Ketamine's therapeutic index is large and as levels are increased, general anesthesia is achieved. Unlike other current general anesthetic agents, vital functions (e.g., neuromuscular tone, airway patency, respirations, and cardiovascular function) are maintained. All narcotic agents (e.g., Morphine) display effects opposite of those of Ketamine with respect to vital functions. As narcotic levels are increased, respirations, neuromuscular tone, and airway patency are decreased while cardiovascular function may also be compromised, particularly due to peripheral vasodilatation. Ketamine also induces bronchodilation, which is particularly useful when irritants cause bronchoconstriction and coughing. Morphine suppresses coughing and either leaves bronchomotor tone unaltered or increases it (see, e.g., *Anesthesia*. 4th ed. 1994, Churchill Livingstone: New York; *Goodman & Gilman's the pharmacological basis of therapeutics*. 9th ed. 1996, McGraw-Hill, Health Professions Division New York; each herein incorporated by reference in its entirety). When faced with severe injuries and blood loss, low dose Ketamine provides analgesia and amnesia while preserving homeostatic mechanisms and vital functions. Ketamine levels can be increased to achieve a state of "dissociation" in which major procedures (e.g., an amputation) can be accomplished with cardio respiratory stability while the individual seems unattached to the procedure. Dissociation is unique to Ketamine.

In some embodiments, the present invention provides dendrimer conjugates comprising Ketamine and Lorazepam. Unfortunately, disforic reactions can occur in a small percentage of recipients, but can be effectively treated with the concurrent administration of benzodiazepines (e.g., Lorazepam). Lorazepam has excellent amnestic and anxiolytic properties, which are very desirable in the severely injured combatant (see, e.g., *Anesthesia*. 4th ed. 1994, Churchill Livingstone: New York; *Goodman & Gilman's the pharmacological basis of therapeutics*. 9th ed. 1996, McGraw-Hill, Health Professions Division: New York; each herein incorporated by reference in its entirety). It does not have analgesic nor anesthetic properties. It has mild, centrally mediated muscle relaxant properties while it is an anticonvulsant. Its effects on homeostasis of the respiratory and hemodynamic system are mildly depressant when used in the dose range of its anxiolytic properties.

In some embodiments, the pain relief agent is Morphine. Morphine is the standard against which all other analgesics are compared. It is less potent as an analgesic when compared to Ketamine. Its sedation can be accompanied by euphoria, but its amnestic and anxiolytic effects are less when compared to Ketamine and Lorazepam. Even in high doses, Morphine is a poor anesthetic and an unreliable amnestic, but these properties may maintain co-operativity on the battlefield. Morphine's analgesic effects overlap closely with its effects on homeostasis of the respiratory and hemodynamic system. Thus as the dosage of Morphine is increased, depression of respirations, and loss of airway patency and reflexes become soon apparent relative to Ketamine's effect. Its hemodynamic effects include veno-vasodilatation within the range of Morphine's analgesia. Thus, in the severely injured with blood loss, Morphine's analgesic range is limited by its effects on homeostasis of vital functions. Morphine's therapeutic index, particularly in the setting of the severely injured combatant, is low compared to the index for Ketamine. Thus, Morphine has many good qualities but should be administered in a manner to avoid side effects.

In some embodiments, the pain relief agent antagonist is Doxapram. Doxapram is a respiratory stimulant causing an increase in tidal volume with an increase in respiratory rate used in acute respiratory insufficiency. It can improve cardiac output in the setting of hypovolemia. It may increase catecholamines release. Doxapram is useful as a respiratory and cardiovascular stimulant in the battlefield field setting to reduce or negate respiratory and hemodynamic effects of any proposed analgesic-amnestic-anxiolytic agents. Thus, the release of Doxapram is a viable counter-regulatory effect for respiratory depression whatever the cause.

In some embodiments, the pain relief agent antagonist is Naloxone. Naloxone is an effective, selective opioid (e.g., Morphine) antagonist. It reverses a range of Morphine's effects including Morphine's analgesia and respiratory depression. Although Morphine's analgesic and respiratory ranges overlap, low dose infusions of Naloxone can reverse Morphine's respiratory depression while its analgesic effect is relatively unaffected and pain-relief can remain present. Thus, it is a prime candidate for a dendrimer-drug delivery system requiring a Morphine feedback mechanism.

In some embodiments, pain relief agents include, but are not limited to, analgesic drugs and respective antagonists. Examples of analgesic drugs include, but are not limited to, paracetamol and Non-steroidal anti-inflammatory drugs (NSAIDs), COX-2 inhibitors, opiates and morphonimimetics, and specific analgesic agents.

Examples of NSAIDs include, but are not limited to, salicylates (e.g., Acetylsalicylic acid (Aspirin), Amoxiprin, Benorylate/Benorilate, Choline magnesium salicylate, Diflunisal, Ethenzamide, Faislamine, Methyl salicylate, Magnesium salicylate, Salicyl salicylate, Salicylamide), arylalkanoic acids (e.g., Diclofenac, Aceclofenac, Acemethacin, Alclofenac, Bromfenac, Etodolac, Indometacin, Nabumetone, Oxametacin, Proglumetacin, Sulindac, Tolmetin), 2-arylpropionic acids (profens) (e.g., Ibuprofen, Alminoprofen, Benoxaprofen, Carprofen, Dexibuprofen, Dexketoprofen, Fenbufen, Fenoprofen, Flunoxaprofen, Flurbiprofen, Ibuproxam, Indoprofen, Ketoprofen, Ketorolac, Loxoprofen, Naproxen, Oxaprozin, Pirprofen, Suprofen, Tiaprofenic acid), N-arylanthranilic acids (fenamic acids) (e.g., Mefenamic acid, Flufenamic acid, Meclofenamic acid, Tolfenamic acid), pyrazolidine derivatives (e.g., Phenylbutazone, Ampyrone, Azapropazone, Clofezone, Kebuzone, Metamizole, Mofebutazone, Oxyphenbutazone, Phenazone, Sulfinpyrazone), oxicams (e.g., Piroxicam, Droxicam, Lornoxicam, Meloxicam, Tenoxicam), sulphonanilides (e.g., nimesulide), licofelone, and omega-3 fatty acids.

Examples of COX-2 inhibitors include, but are not limited to Celecoxib, Etoricoxib, Lumiracoxib, Parecoxib, Rofecoxib, Valdecoxib.

Examples of Opiates include, but are not limited to, natural opiates (e.g., alkaloids contained in the resin of the opium poppy including morphine, codeine and thebaine), semi-synthetic opiates (e.g., created from the natural opioids, such as hydromorphone, hydrocodone, oxycodone, oxymorphone, desomorphine, diacetylmorphine (Heroin), nicomorphine, dipropanoylmorphine, diamorphine, benzylmorphine, Buprenorphine, Nalbuphine, Pentazocine, meperidine, diamorphine, and ethylmorphine), fully synthetic opioids (e.g., such as fentanyl, pethidine, Oxycodone, Oxymorphone, methadone, tramadol, Butorphanol, Levorphanol, and propoxyphene), and endogenous opioid peptides (e.g., produced naturally in the body, such as endorphins, enkephalins, dynorphins, and endomorphins).

Additional analgesics include, but are not limited to, tricyclic antidepressants (e.g., amitriptyline, carbamazepine, gabapentin, and pregabalin), Tetrahydrocannabinol, ketamine, clonidine, $\alpha_2$-adrenoreceptor agonists, mexiletine, Orphenadrine, cyclobenzaprine, scopolamine, atropine, gabapentin, first-generation antidepressants and other drugs possessing anticholinergic and/or antispasmodic.

In some embodiments, pain relief agents include anesthetic drugs and respective antagonists. Examples of anesthetic drugs include, but are not limited to, local anesthetics (e.g., procaine, amethocaine, cocaine, lidocaine, prilocaine, bupivacaine, levobupivacaine, ropivacaine, dibucaine), inhaled anesthetics (e.g., Desflurane, Enflurane, Halothane, Isoflurane, Nitrous oxide, Sevoflurane, Xenon), intravenous anesthetics (e.g., Barbiturates (e.g., amobarbital (Amytal), pentobarbital (Nembutal), secobarbital (Seconal), Phenobarbital, Methohexital, Thiopental, Methylphenobarbital, Metharbital, Barbexaclone)), Benzodiazepines (e.g., alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze), Triazolam), Etomidate, Ketamine, Propofol).

In some embodiments, pain relief agents include anticonvulsant drugs and respective antagonists. Examples of anticonvulsant drugs include, but are not limited to, aldehydes (e.g., paraldehyde), aromatic allylic alcohols (e.g., stiripentol), barbiturates (e.g., amobarbital (Amytal), pentobarbital (Nembutal), secobarbital (Seconal), Phenobarbital, Methohexital, Thiopental, Methylphenobarbital, Metharbital, Barbexaclone), benzodiazepines (e.g., alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze), Triazolam), bromides (e.g., potassium bromide), carbamates (e.g., felbamate), carboxamides (e.g., carbamazepine, oxcarbazepine), fatty acids (e.g., valproates (e.g., valproic acid, sodium valproate, and divalproex sodium), Vigabatrin, Progabide, Tiagabine), fructose derivatives (e.g., topiramate), gaba analogs (e.g., gabapentin, pregabalin), hydantoins (e.g., Ethotoin, Phenyloin, Mephenyloin, Fosphenyloin), Oxazolidinediones (e.g., paramethadione, trimethadione, ethadione), priopionates (e.g., primidone), pyrrolidines (e.g., brivaracetam, levetiracetam, seletracetam), succinimides (e.g., Ethosuximide, Phensuximide, Mesuximide), sulfonamides (e.g., Acetazolamide, Sulthiame, Methazolamide, Zonisamide), triazines (e.g., lamotrigine), ureas (e.g., pheneturide, phenacemide), and valproylamdies (amide derivatives of valproate) (e.g., valpromide, valnoctamide).

In some embodiments, pain relief agents include mood stabilizer drugs. Examples of mood stabilizer drugs include, but are not limited to, Lithium carbonate, lithium orotate, lithium salt, Valproic acid (Depakene), divalproex sodium (Depakote), sodium valproate (Depacon), Lamotrigine (Lamictal), Carbamazepine (Tegretol), Gabapentin (Neurontin), Oxcarbazepine (Trileptal), and Topiramate (Topamax).

In some embodiments, pain relief agents include psycholeptic drugs. Examples of psycholeptic drugs include, but are not limited to, anxiolytic drugs, antipsychotic drugs, and hypnotic drugs, and sedative drugs. Examples of anxiolytic drugs include, but are not limited to, benzodiazepines (e.g., alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze), Triazolam), serotonin 1A agonists (e.g., Buspirone (BuSpar)), barbituates (e.g., amobarbital (Amytal), pentobarbital (Nembutal), secobarbital (Seconal), Phenobarbital, Methohexital, Thiopental, Methylphenobarbital, Metharbital, Barbexaclone), hydroxyzine, cannabidiol, and herbal treatments. (e.g., valerian, kava (Kava Kava), chamomile, Kratom, Blue *Lotus* extracts, *Sceletium tortuosum* (kanna) and *bacopa monniera*). are reputed to have anxiolytic properties. Examples of antipsychotic drugs include, but are not limited to, butyrophenones (e.g., haloperidol), phenothiazines (e.g., Chlorpromazine (Thorazine), Fluphenazine (Prolixin), Perphenazine (Trilafon), Prochlorperazine (Compazine), Thioridazine (Mellaril), Trifluoperazine (Stelazine), Mesoridazine, Promazine, Triflupromazine (Vesprin), Levomepromazine (Nozinan), Promethazine (Phenergan)), thioxanthenes (e.g., Chlorprothixene, Flupenthixol (Depixol and Fluanxol), Thiothixene (Navane), Zuclopenthixol (Clopixol & Acuphase)), clozapine, olanzapine, Risperidone (Risperdal), Quetiapine (Seroquel), Ziprasidone (Geodon), Amisulpride (Solian), Paliperidone (Invega), dopamine, bifeprunox, norclozapine (ACP-104), Aripiprazole (Abilify), Tetrabenazine, and Cannabidiol. Examples of hypnotics include, but are not limited to, Barbiturates, Opioids, benzodiazepines (e.g., alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze), Triazolam), nonbenzodiazepines (e.g., Zolpidem, Zaleplon, Zopiclone, Eszopiclone), antihistamines (e.g., Diphenhydramine, Doxylamine, Hydroxyzine, Promethazine), gamma-hydroxybutyric acid (Xyrem), Glutethimide, Chloral hydrate, Ethchlorvynol, Levomepromazine, Chlormethiazole, Melatonin, and Alcohol. Examples of sedatives include, but are not limited to, barbituates (e.g., amobarbital (Amytal), pentobarbital (Nembutal), secobarbital (Seconal), Phenobarbital, Methohexital, Thiopental, Methylphenobarbital, Metharbital, Barbexaclone), benzodiazepines (e.g., alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze), Triazolam), Herbal sedatives (e.g., ashwagandha, catnip, kava (*Piper methysticum*), mandrake, marijuana, valerian), solvent sedatives (e.g., chloral hydrate (Noctec), diethyl ether (Ether), ethyl alcohol (alcoholic beverage), methyl trichloride (Chloroform)), nonbenzodiazepine sedatives (e.g., eszopiclone (Lunesta), zaleplon (Sonata), zolpidem (Ambien), zopiclone (Imovane, Zimovane)), clomethiazole (clomethiazole), gamma-hydroxybutyrate (GHB), Thalidomide, ethchlorvynol (Placidyl), glutethimide (Doriden), ketamine (Ketalar, Ketaset), methaqualone (Sopor, Quaalude), methyprylon (Noludar), and ramelteon (Rozerem).

In some embodiments, pain relief agents include psychoanaleptic drugs. Examples of psychoanaleptic drugs include, but are not limited to, antidepressants, psychostimulants, and anti-dementia drugs. Examples of antidepressants include, but are not limited to, selective serotonin reuptake inhibitors (SSRIs) (e.g., fluoxetine (Prozac), paroxetine (Paxil, Seroxat), escitalopram (Lexapro, Esipram), citalopram (Celexa), and sertraline (Zoloft)), serotonin-norepinephrine reuptake inhibitors (SNRIs) (e.g., venlafaxine (Effexor), and duloxetine (Cymbalta)), noradrenergic and specific serotonergic antidepressants (NASSAs) (e.g., mirtazapine (Avanza, Zispin, Remeron)), norepinephrine (noradrenaline) reuptake inhibitors (NRIs) (e.g., reboxetine (Edronax)), norepinephrine-dopamine reuptake inhibitors (e.g., bupropion (Wellbutrin, Zyban)), tricyclic antidepressants (TCAs) (e.g., amitriptyline and desipramine), monoamine oxidase inhibitor (MAOIs) (e.g., phenelzine (Nardil), moclobemide (Manerix), selegiline), and augmentor drugs (e.g., tryptophan (Tryptan) and buspirone (Buspar)). Examples of psychostimulants include, but are not limited to, amphetamine, methamphetamine, cocaine, methylphenidate, and arecoline). Examples of anti-dementia drugs include, but are not limited to, Acetylcholinesterase inhibitors (e.g., Tacrine (Cognex), donepezil (Aricept), galantamine (Razadyne), and rivastigmine (Exelon).

In some embodiments, pain relief agents include muscle relaxant drugs. Examples of muscle relaxant drugs include, but are not limited to, depolarizing muscle relaxants (e.g., Succinylcholine), short acting non-depolarizing muscle relaxants (e.g., Mivacurium, Rapacuronium), intermediate acting non-depolarizing muscle relaxants (e.g., Atracurium, Cisatracurium, Rocuronium, Vecuronium), and long acting non-depolarizing muscle relaxants (e.g., Alcuronium, Doxacurium, Gallamine, Metocurine, Pancuronium, Pipecuronium, d-Tubocurarine).

In some embodiments, the pain relief agent antagonists include drugs that counter the effect (e.g., side effect, main effect, cardiovascular effect) of a pain relief agent. The present invention is not limited to particular pain relief agent antagonists (e.g., Anesthetic antagonists, Analgesic antagonists, Anticonvulsant antagonists, Mood stabilizer antagonists, Psycholeptic drug antagonists, Psychoanaleptic drug antagonists, and muscle relaxant antagonists). In some embodiments, the pain relief agent antagonists include, but are not limited to, respiratory stimulants (e.g., Doxapram, BIMU-8, CX-546), opiod receptor antagonists (e.g., Naloxone, naltrexone, nalorphine, levallorphan, cyprodime, naltrindole, norbinaltorphimine, buprenorphine), agents that effect of benzodiazepines (e.g., flumazenil), agents that reverse the effect of non-depolarizing muscle relaxants (e.g., neostigmine).

In some embodiments, a dendrimer conjugated comprising a linker may comprise nearly any therapeutic agent comprising a hydroxyl and/or amino group. In some embodiments, the therapeutic agent is an anti-cancer drug or agent. For example, in some embodiments, the therapeutic agent is doxorubicin (or an analog thereof) or paclitaxel (or an analog thereof). In some embodiments, a dendrimer conjugate of the invention comprises a therapeutic agent comprising a single reactive group (e.g., at a primary or secondary position). In some embodiments, a dendrimer conjugate of the present invention is synthesized utilizing a selective protection/deprotection strategy if multiple functional groups are present within a therapeutic agent. In some embodiments, a dendrimer conjugate of the present invention provides the ability to deliver a therapeutic agent that, when not in the context of the dendrimer conjugate (e.g., in the absence of conjugation to a dendrimer (e.g., a dendrimer comprising a linker and a trigger (e.g., configured to shield and/or mask the therapeutic drug and/or prohibit release of the therapeutic drug until the dendrimer reaches and reacts with a target site))) is toxic to a subject (e.g., that is too toxic to be utilized to treat a subject). Thus, in some embodiments, the present invention provides dendrimer conjugates comprising therapeutic agents that suffer from delivery issues and/or toxicity issues and/or non-specificity issues in the absence of being conjugated to a dendrimer conjugate. For example, in some embodiments, the present invention provides a dendrimer conjugate comprising a therapeutic agent comprising a compound of the camptothecin family (e.g., IRINOTECAN). IRINOTECAN is a prodrug of 10-hydroxycamptothecin (SN-38), which is 1000-fold more cytotoxic than IRINOTECAN. It has been reported that the conversion of irinotecan to hydroxycamptothecin has very low efficiency. Thus, in some embodiments, the present invention provides a dendrimer conjugate comprising hydroxycamptothecin.

In some embodiments of the present invention, the biological monitoring agent comprises an agent that measures an effect of a therapeutic agent (e.g., directly or indirectly measures a cellular factor or reaction induced by a therapeutic agent), however, the present invention is not limited by the nature of the biological monitoring agent. In some embodiments, the monitoring agent is capable of detecting (e.g., measuring) apoptosis caused by the therapeutic agent.

In some embodiments of the present invention, the imaging agent comprises a radioactive label including, but not limited to $^{14}C$, $^{36}Cl$, $^{57}Co$, $^{58}Co$, $^{51}Cr$, $^{125}I$, $^{131}I$, $^{111}Ln$, $^{152}Eu$, $^{59}Fe$, $^{67}Ga$, $^{32}P$, $^{186}Re$, $^{75}Se$, Tc-99m, and $^{175}Yb$. In some embodiments, the imaging agent comprises a fluorescing entity. In a preferred embodiment, the imaging agent is fluorescein isothiocyanate or 6-TAMARA.

The present invention is not limited to any particular targeting agent. In some embodiments, targeting agents are conjugated to the dendrimers (e.g., Baker-Huang PAMAM dendrimers) for delivery of the dendrimers to desired body regions (e.g., to the central nervous system (CNS). The targeting agents are not limited to targeting specific body regions. In some embodiments, the targeting agents target the central nervous system (CNS). In some embodiments, where the targeting agent is specific for the CNS, the targeting agent is transferrin (see, e.g., Daniels, T. R., et al., Clinical Immunology, 2006. 121(2): p. 159-176; Daniels, T. R., et al., Clinical Immunology, 2006. 121(2): p. 144-158; each herein incorporated by reference in their entireties). Transferrin has been utilized as a targeting vector to transport, for example, drugs, liposomes and proteins across the BBB by receptor mediated transcytosis (see, e.g., Smith, M. W. and M. Gumbleton, Journal of Drug Targeting, 2006. 14(4): p. 191-214; herein incorporated by reference in its entirety). In some embodiments, the targeting agents target neurons within the central nervous system (CNS). In some embodiments, where the targeting agent is specific for neurons within the CNS, the targeting agent is a synthetic tetanus toxin fragment (e.g., a 12 amino acid peptide (Tet 1) (HLNILSTLWKYR (SEQ ID NO: 2))) (see, e.g., Liu, J. K., et al., Neurobiology of Disease, 2005. 19(3): p. 407-418; herein incorporated by reference in its entirety).

In some embodiments, the targeting agent is a moiety that has affinity for a tumor associated factor. For example, a number of targeting agents are contemplated to be useful in the present invention including, but not limited to, RGD sequences, low-density lipoprotein sequences, a NAALA-Dase inhibitor, epidermal growth factor, and other agents that bind with specificity to a target cell (e.g., a cancer cell)). In some embodiments, the targeting agent is an antibody, receptor ligand, hormone, vitamin, or antigen. However, the present invention is not limited by the nature of the targeting agent. In some embodiments, the antibody is specific for a disease-specific antigen. In some embodiments, the disease-specific antigen comprises a tumor-specific antigen. In some embodiments, the receptor ligand includes, but is not limited to, a ligand for CFTR, EGFR, estrogen receptor, FGR2, folate receptor, IL-2 receptor, glycoprotein, or VEGFR. In some embodiments, the receptor ligand is folic acid.

The present invention is not limited to cancer and/or tumor targeting agents. Indeed, dendrimers of the present invention can be targeted (e.g., via a linker conjugated to the dendrimer wherein the linker comprises a targeting agent) to a variety of target cells or tissues (e.g., to a biologically relevant environment) via conjugation to an appropriate targeting agent. For example, in some embodiments, the targeting agent is a moiety that has affinity for an inflammatory factor (e.g., a cytokine or a cytokine receptor moiety (e.g., TNF-α receptor)). In some embodiments, the targeting agent is a sugar, peptide, antibody or antibody fragment, hormone, hormone receptor, or the like.

In some embodiments of the present invention, the targeting agent includes, but is not limited to an antibody, receptor ligand, hormone, vitamin, and antigen, however, the present invention is not limited by the nature of the targeting agent. In some embodiments, the antibody is specific for a disease-specific antigen. In some embodiments, the disease-specific antigen comprises a tumor-specific antigen. In some embodiments, the receptor ligand includes, but is not limited to, a ligand for CFTR, EGFR, estrogen receptor, FGR2, folate receptor, IL-2 receptor, glycoprotein, and VEGFR. In some embodiments, the receptor ligand is folic acid.

In some embodiments, the dendrimer conjugates of the present invention are configured such that they are readily cleared from the subject (e.g., so that there is little to no detectable toxicity at efficacious doses) (see, e.g., U.S. patent application Ser. No. 12/570,977; herein incorporated by reference in its entirety).

The present invention also provides a method of treating a medical condition and/or a disease (e.g., cancer, inflammatory disease, chronic pain, autoimmune disease, etc.) comprising administering to a subject suffering from or susceptible to medical condition and/or a disease a therapeutically effective amount of a composition comprising a dendrimer conjugate (e.g., comprising a linker and/or trigger and a therapeutic agent) described herein.

In some embodiments of the present invention, methods and compositions are provided for the treatment of inflammatory diseases (e.g., dendrimers conjugated with therapeutic agents configured for treating inflammatory diseases). Inflammatory diseases include but are not limited to arthritis, rheumatoid arthritis, psoriatic arthritis, osteoarthritis, degenerative arthritis, polymyalgia rheumatic, ankylosing spondylitis, reactive arthritis, gout, pseudogout, inflammatory joint disease, systemic lupus erythematosus, polymyositis, and fibromyalgia. Additional types of arthritis include achilles tendinitis, achondroplasia, acromegalic arthropathy, adhesive capsulitis, adult onset Still's disease, anserine bursitis, avascular necrosis, Behcet's syndrome, bicipital tendinitis, Blount's disease, brucellar spondylitis, bursitis, calcaneal bursitis, calcium pyrophosphate dihydrate deposition disease (CPPD), crystal deposition disease, Caplan's syndrome, carpal tunnel syndrome, chondrocalcinosis, chondromalacia patellae, chronic synovitis, chronic recurrent multifocal osteomyelitis, Churg-Strauss syndrome, Cogan's syndrome, corticosteroid-induced osteoporosis, costosternal syndrome, CREST syndrome, cryoglobulinemia, degenerative joint disease, dermatomyositis, diabetic finger sclerosis, diffuse idiopathic skeletal hyperostosis (DISH), discitis, discoid lupus erythematosus, drug-induced lupus, Duchenne's muscular dystrophy, Dupuytren's contracture, Ehlers-Danlos syndrome, enteropathic arthritis, epicondylitis, erosive inflammatory osteoarthritis, exercise-induced compartment syndrome, Fabry's disease, familial Mediterranean fever, Farber's lipogranulomatosis, Felty's syndrome, Fifth's disease, flat feet, foreign body synovitis, Freiberg's disease, fungal arthritis, Gaucher's disease, giant cell arteritis, gonococcal arthritis, Goodpasture's syndrome, granulomatous arteritis, hemarthrosis, hemochromatosis, Henoch-Schonlein purpura, Hepatitis B surface antigen disease, hip dysplasia, Hurler syndrome, hypermobility syndrome, hypersensitivity vasculitis, hypertrophic osteoarthropathy, immune complex disease, impingement syndrome, Jaccoud's arthropathy, juvenile ankylosing spondylitis, juvenile dermatomyositis, juvenile rheumatoid arthritis, Kawasaki disease, Kienbock's disease, Legg-Calve-Perthes disease, Lesch-Nyhan syndrome, linear scleroderma, lipoid dermatoarthritis, Lofgren's syndrome, Lyme disease, malignant synovioma, Marfan's syndrome, medial plica syndrome, metastatic carcinomatous arthritis, mixed connective tissue disease (MCTD), mixed cryoglobulinemia, mucopolysaccharidosis, multicentric reticulohistiocytosis, multiple epiphyseal dysplasia, mycoplasmal arthritis, myofascial pain syndrome, neonatal lupus, neuropathic arthropathy, nodular panniculitis, ochronosis, olecranon bursitis, Osgood-Schlatter's disease, osteoarthritis, osteochondromatosis, osteogenesis imperfecta, osteomalacia, osteomyelitis, osteonecrosis, osteoporosis, overlap syndrome, pachydermoperiostosis Paget's disease of bone, palindromic rheumatism, patellofemoral pain syndrome, Pellegrini-Stieda syndrome, pigmented villonodular synovitis, piriformis syndrome, plantar fasciitis, polyarteritis nodos, Polymyalgia rheumatic, polymyositis, popliteal cysts, posterior tibial tendinitis, Pott's disease, prepatellar bursitis, prosthetic joint infection, pseudoxanthoma elasticum, psoriatic arthritis, Raynaud's phenomenon, reactive arthritis/Reiter's syndrome, reflex sympathetic dystrophy syndrome, relapsing polychondritis, retrocalcaneal bursitis, rheumatic fever, rheumatoid vasculitis, rotator cuff tendinitis, sacroiliitis, *salmonella* osteomyelitis, sarcoidosis, saturnine gout, Scheuermann's osteochondritis, scleroderma, septic arthritis, seronegative arthritis, *shigella* arthritis, shoulder-hand syndrome, sickle cell arthropathy, Sjogren's syndrome, slipped capital femoral epiphysis, spinal stenosis, spondylolysis, *staphylococcus* arthritis, Stickler syndrome, subacute cutaneous lupus, Sweet's syndrome, Sydenham's chorea, syphilitic arthritis, systemic lupus erythematosus (SLE), Takayasu's arteritis, tarsal tunnel syndrome, tennis elbow, Tietse's syndrome, transient osteoporosis, traumatic arthritis, trochanteric bursitis, tuberculosis arthritis, arthritis of Ulcerative colitis, undifferentiated connective tissue syndrome (UCTS), urticarial vasculitis, viral arthritis, Wegener's granulomatosis, Whipple's disease, Wilson's disease, and yersinial arthritis.

In some embodiments, the conjugated dendrimers of the present invention configured for treating autoimmune disorders and/or inflammatory disorders (e.g., rheumatoid arthritis) are co-administered to a subject (e.g., a human suffering from an autoimmune disorder and/or an inflammatory disorder) with a therapeutic agent configured for treating autoimmune disorders and/or inflammatory disorders (e.g., rheumatoid arthritis). Examples of such agents include, but are not limited to, disease-modifying antirheumatic drugs (e.g., leflunomide, methotrexate, sulfasalazine, hydroxychloroquine), biologic agents (e.g., rituximab, infliximab, etanercept, adalimumab, golimumab), nonsteroidal anti-inflammatory drugs (e.g., ibuprofen, celecoxib, ketoprofen, naproxen, piroxicam, diclofenac), analgesics (e.g., acetaminophen, tramadol), immunomodulators (e.g., anakinra, abatacept), and glucocorticoids (e.g., prednisone, methylprednisone), IL-1 inhibitors, and metalloprotease inhibitors.

In some embodiments, the medical condition and/or disease is pain (e.g., chronic pain, mild pain, recurring pain, severe pain, etc.). In some embodiments, the dendrimer conjugates are configured to deliver pain relief agents to a subject. In some embodiments, the dendrimer conjugates are configured to deliver pain relief agents and pain relief agent antagonists to counter the side effects of pain relief agents. The dendrimer conjugates are not limited to treating a particular type of pain and/or pain resulting from a disease. Examples include, but are not limited to, pain resulting from trauma (e.g., trauma experienced on a battlefield, trauma experienced in an accident (e.g., car accident)).

In some embodiments, the dendrimer is conjugated with one or more pain relief agents. In some embodiments, the dendrimer is co-administered with one or more pain relief agents. In some embodiments, the pain relief agents include, but are not limited to, analgesic drugs, anxiolytic drugs, anesthetic drugs, antipsychotic drugs, hypnotic drugs, sedative drugs, and muscle relaxant drugs (see, e.g., U.S. patent application Ser. No. 12/570,977; herein incorporated by reference in its entirety).

In some embodiments, the disease is cancer. The present invention is not limited by the type of cancer treated using the compositions and methods of the present invention. Indeed, a variety of cancer can be treated including, but not limited to, prostate cancer, colon cancer, breast cancer, lung cancer and epithelial cancer.

In some embodiments, the disease is a neoplastic disease, selected from, but not limited to, leukemia, acute leukemia, acute lymphocytic leukemia, acute myelocytic leukemia, myeloblastic, promyelocytic, myelomonocytic, monocytic, erythroleukemia, chronic leukemia, chronic myelocytic, (granulocytic) leukemia, chronic lymphocytic leukemia, Polycythemia vera, lymphoma, Hodgkin's disease, non-Hodgkin's disease, Multiple myeloma, Waldenstrom's macroglobulinemia, Heavy chain disease, solid tumors, sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, and neuroblastomaretinoblastoma. In some embodiments, the disease is an inflammatory disease selected from the group consisting of, but not limited to, eczema, inflammatory bowel disease, rheumatoid arthritis, asthma, psoriasis, ischemia/reperfusion injury, ulcerative colitis and acute respiratory distress syndrome. In some embodiments, the disease is a viral disease selected from the group consisting of, but not limited to, viral disease caused by hepatitis B, hepatitis C, rotavirus, human immunodeficiency virus type I (HIV-I), human immunodeficiency virus type II (HIV-II), human T-cell lymphotropic virus type I (HTLV-I), human T-cell lymphotropic virus type II (HTLV-II), AIDS, DNA viruses such as hepatitis type B and hepatitis type C virus; parvoviruses, such as adeno-associated virus and cytomegalovirus; papovaviruses such as papilloma virus, polyoma viruses, and SV40; adenoviruses; herpes viruses such as herpes simplex type I (HSV-I), herpes simplex type II (HSV-II), and Epstein-Barr virus; poxviruses, such as variola (smallpox) and vaccinia virus; and RNA viruses, such as human immunodeficiency virus type I (HIV-I), human immunodeficiency virus type II (HIV-II), human T-cell lymphotropic virus type I (HTLV-I), human T-cell lymphotropic virus type II (HTLV-II), influenza virus, measles virus, rabies virus, Sendai virus, picornaviruses such as poliomyelitis virus, coxsackieviruses, rhinoviruses, reoviruses, togaviruses such as rubella virus (German measles) and Semliki forest virus, arboviruses, and hepatitis type A virus.

The dendrimers of the present invention find use in the detection and treatment of a variety of cancers. Indeed, the present invention is not limited by the type of cancer to be treated. Thus, in some embodiments, the present invention provides compositions comprising dendrimer conjugates for the targeting and identification of angiogenesis associated with cancers (e.g., carcinomas). For example, in some embodiments, a dendrimer conjugate of the present invention further comprises a targeting agent (e.g., folic acid moiety) that associates with high affinity to a targeting agent ligand (e.g., receptor) on a cancer cell (e.g., carcinoma cells and/or solid tumor cells). In some embodiments, dendrimer conjugate and a targeting agent, that target and identify cancer cells and/or angiogenesis associated with cancer, further comprise a therapeutic agent that inhibits angiogenesis thereby treating the cancer. In some embodiments, treatment with dendrimer conjugates and an anti-angiogenic agent are used in combination with other dendrimers of the present invention, with other chemotherapeutic treatments, and/or as a treatment following surgical removal of a tumor or cancerous tissue. In some embodiments, a targeting moiety (e.g., folic acid or other targeting moiety described herein) possesses a high affinity for ligands (e.g., receptors or other types of proteins or molecules) present on cancer cell possessing such ligands thereby permitting the targeting, identification and treatment of disease (e.g., cancer) with little to no toxicity to surrounding healthy cells and tissue.

In some embodiments, the dendrimer is conjugated with one or more anti-cancer agents. In some embodiments, the dendrimer is co-administered with one or more anti-cancer agents. Examples of anti-cancer agents include, but are not limited to, Acivicin; Aclarubicin; Acodazole Hydrochloride; Acronine; Adozelesin; Adriamycin; Aldesleukin; Alitretinoin; Allopurinol Sodium; Altretamine; Ambomycin; Ametantrone Acetate; Aminoglutethimide; Amsacrine; Anastrozole; Annonaceous Acetogenins; Anthramycin; Asimicin; Asparaginase; Asperlin; Azacitidine; Azetepa; Azotomycin; Batimastat; Benzodepa; Bexarotene; Bicalutamide; Bisantrene Hydrochloride; Bisnafide Dimesylate; Bizelesin; Bleomycin Sulfate; Brequinar Sodium; Bropirimine; Bullatacin; Busulfan; Cabergoline; Cactinomycin; Calusterone; Caracemide; Carbetimer; Carboplatin; Carmustine; Carubicin Hydrochloride; Carzelesin; Cedefingol; Celecoxib; Chlorambucil; Cirolemycin; Cisplatin; Cladribine; Crisnatol Mesylate; Cyclophosphamide; Cytarabine; Dacarbazine; DACA (N-[2-(Dimethyl-amino)ethyl]acridine-4-carboxamide); Dactinomycin; Daunorubicin Hydrochloride; Daunomycin; Decitabine; Denileukin Diftitox; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Fluorocitabine; Fosquidone; Fostriecin Sodium;

FK-317; FK-973; FR-66979; FR-900482; Gemcitabine; Geimcitabine Hydrochloride; Gemtuzumab Ozogamicin; Gold Au 198; Goserelin Acetate; Guanacone; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Methoxsalen; Metoprine; Meturedepa; Mitindomide; Mitocarcin; Mitocromin; Mitogillin; Mitomalcin; Mitomycin; Mytomycin C; Mitosper; Mitotane; Mitoxantrone Hydrochloride; Mycophenolic Acid; Nocodazole; Nogalamycin; Oprelvekin; Ormaplatin; Oxisuran; Paclitaxel; Pamidronate Disodium; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rituximab; Rogletimide; Rolliniastatin; Safingol; Safingol Hydrochloride; Samarium/Lexidronam; Semustine; Simtrazene; Sparfosate Sodium; Sparsomycin; Spirogermanium Hydrochloride; Spiromustine; Spiroplatin; Squamocin; Squamotacin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trastuzumab; Trestolone Acetate; Triciribine Phosphate; Trimetrexate; Trimetrexate Glucuronate; Triptorelin; Tubulozole Hydrochloride; Uracil Mustard; Uredepa; Valrubicin; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid; 2-chloro-2'-arabino-fluoro-T-deoxyadenosine; 2-chloro-2'-deoxyadenosine; anisomycin; trichostatin A; hPRL-G129R; CEP-751; linomide; sulfur mustard; nitrogen mustard (mechlorethamine); cyclophosphamide; melphalan; chlorambucil; ifosfamide; busulfan; N-methyl-N-nitrosourea (MNU); N,N'-Bis(2-chloroethyl)-N-nitrosourea (BCNU); N-(2-chloroethyl)-N'-cyclohex-yl-N-nitrosourea (CCNU); N-(2-chloroethyl)-N'-(trans-4-methylcyclohexyl-N-nitrosourea (MeCCNU); N-(2-chloroethyl)-N'-(diethyl)ethylphosphonate-N-nitrosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis (platinum); tomudex; azacitidine; cytarabine; gemcitabine; 6-Mercaptopurine; 6-Thioguanine; Hypoxanthine; teniposide; 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl)retinamide; 13-cis retinoic acid; 3-Methyl TTNEB; 9-cis retinoic acid; fludarabine (2-F-ara-AMP); and 2-chlorodeoxyadenosine (2-Cda). Other anti-cancer agents include, but are not limited to, Antiproliferative agents (e.g., Piritrexim Isothionate), Antiprostatic hypertrophy agent (e.g., Sitogluside), Benign prostatic hyperplasia therapy agents (e.g., Tamsulosin Hydrochloride), Prostate growth inhibitor agents (e.g., Pentomone), and Radioactive agents: Fibrinogen I 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m sulfur Colloid; Technetium Tc 99m Teboroxime; Technetium Tc 99m Tetrofosmin; Technetium Tc 99m Tiatide; Thyroxine I 125; Thyroxine I 131; Tolpovidone I 131; Triolein I 125; and Triolein I 131.

Additional anti-cancer agents include, but are not limited to anti-cancer Supplementary Potentiating Agents: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{++}$ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL. Still other anticancer agents include, but are not limited to, annonaceous acetogenins; asimicin; rolliniastatin; guanacone, squamocin, bullatacin; squamotacin; taxanes; paclitaxel; gemcitabine; methotrexate FR-900482; FK-973; FR-66979; FK-317; 5-FU; FUDR; FdUMP; Hydroxyurea; Docetaxel; discodermolide; epothilones; vincristine; vinblastine; vinorelbine; meta-pac; irinotecan; SN-38; 10-OH campto; topotecan; etoposide; adriamycin; flavopiridol; Cis-Pt; carbo-Pt; bleomycin; mitomycin C; mithramycin; capecitabine; cytarabine; 2-C1-2'deoxyadenosine; Fludarabine-$PO_4$; mitoxantrone; mitozolomide; Pentostatin; and Tomudex. One particularly preferred class of anticancer agents are taxanes (e.g., paclitaxel and docetaxel). Another important category of anticancer agent is annonaceous acetogenin.

In some embodiments, the present invention also provides a kit comprising a composition comprising dendrimer (e.g., a Baker-Huang PAMAM dendrimer) conjugate comprising a linker and/or trigger and a therapeutic agent. In some embodiments, the kit comprises a fluorescent agent or bioluminescent agent.

Dendrimers may be characterized by a number of techniques including, but not limited to, electrospray-ionization mass spectroscopy, $^{13}C$ nuclear magnetic resonance spectroscopy, $^{1}H$ nuclear magnetic resonance spectroscopy, high performance liquid chromatography, size exclusion chromatography with multi-angle laser light scattering, ultraviolet spectrophotometry, capillary electrophoresis and gel electrophoresis. These tests assure the uniformity of the polymer population and are important for monitoring quality control of dendrimer manufacture for applications and in vivo usage.

Dendrimer-antibody conjugates for use in in vitro diagnostic applications have previously been demonstrated (See, e.g., Singh et al., Clin. Chem., 40:1845 (1994)), for the production of dendrimer-chelant-antibody constructs, and for the development of boronated dendrimer-antibody conjugates (for neutron capture therapy); each of these latter compounds may be used as a cancer therapeutic (See, e.g., Wu et al., Bioorg. Med. Chem. Lett., 4:449 (1994); Wiener et al., Magn. Reson. Med. 31:1 (1994); Barth et al., Bioconjugate Chem. 5:58 (1994); and Barth et al.).

Some of these conjugates have also been employed in the magnetic resonance imaging of tumors (See, e.g., Wu et al., (1994) and Wiener et al., (1994), supra). Results from this work have documented that, when administered in vivo, antibodies can direct dendrimer-associated therapeutic agents to antigen-bearing tumors. Dendrimers also have been shown to specifically enter cells and carry either chemotherapeutic agents or genetic therapeutics. In particular, studies show that cisplatin encapsulated in dendrimer polymers has increased efficacy and is less toxic than cisplatin delivered by other means (See, e.g., Duncan and Malik, Control Rel. Bioact. Mater. 23:105 (1996)).

Dendrimers have also been conjugated to fluorochromes or molecular beacons and shown to enter cells. They can then be detected within the cell in a manner compatible with sensing apparatus for evaluation of physiologic changes within cells (See, e.g., Baker et al., Anal. Chem. 69:990 (1997)). Finally, dendrimers have been constructed as differentiated block copolymers where the outer portions of the molecule may be digested with either enzyme or light-induced catalysis (See, e.g., Urdea and Horn, Science 261:534 (1993)). This allows the controlled degradation of the polymer to release therapeutics at the disease site and provides a mechanism for an external trigger to release the therapeutic agents.

In some embodiments, dendrimer conjugates of the present invention contain one or more signature identifying agents that are activated by, or are able to interact with, a signature component ("signature"). In preferred embodiments, the signature identifying agent is an antibody, preferably a monoclonal antibody, that specifically binds the signature (e.g., cell surface molecule specific to a cell to be targeted).

In some embodiments of the present invention, tumor cells are identified. Tumor cells have a wide variety of signatures, including the defined expression of cancer-specific antigens such as Muc1, HER-2 and mutated p53 in breast cancer. These act as specific signatures for the cancer, being present in 30% (HER-2) to 70% (mutated p53) of breast cancers. In some embodiments, a dendrimer of the present invention comprises a monoclonal antibody that specifically binds to a mutated version of p53 that is present in breast cancer. In some embodiments, a dendrimer of the present invention comprises an antibody (e.g., monoclonal antibody) with high affinity for a signature including, but not limited to, Muc1 and HER-2.

In some embodiments of the present invention, cancer cells expressing susceptibility genes are identified. For example, in some embodiments, there are two breast cancer susceptibility genes that are used as specific signatures for breast cancer: BRCA1 on chromosome 17 and BRCA2 on chromosome 13. When an individual carries a mutation in either BRCA1 or BRCA2, they are at an increased risk of being diagnosed with breast or ovarian cancer at some point in their lives. These genes participate in repairing radiation-induced breaks in double-stranded DNA. It is thought that mutations in BRCA1 or BRCA2 might disable this mechanism, leading to more errors in DNA replication and ultimately to cancerous growth.

In addition, the expression of a number of different cell surface receptors find use as targets for the binding and uptake of a dendrimer conjugate. Such receptors include, but are not limited to, EGF receptor, folate receptor, FGR receptor 2, and the like.

In some embodiments of the present invention, changes in gene expression associated with chromosomal abborations are the signature component. For example, Burkitt lymphoma results from chromosome translocations that involve the Myc gene. A chromosome translocation means that a chromosome is broken, which allows it to associate with parts of other chromosomes. The classic chromosome translocation in Burkitt lymphoma involves chromosome 8, the site of the Myc gene. This changes the pattern of Myc expression, thereby disrupting its usual function in controlling cell growth and proliferation.

From the discussion above it is clear that there are many different tumor signatures that find use with the present invention, some of which are specific to a particular type of cancer and others which are promiscuous in their origin. The present invention is not limited to any particular tumor signature or any other disease-specific signature. For example, tumor suppressors that find use as signatures in the present invention include, but are not limited to, p53, Muc1, CEA, p16, p21, p27, CCAM, RB, APC, DCC, NF-1, NF-2, WT-1, MEN-1, MEN-II, p73, VHL, FCC and MCC.

In some embodiments of the present invention, a dendrimer conjugate comprises at least one imaging agent that can be readily imaged. The present invention is not limited by the nature of the imaging component used. In some embodiments of the present invention, imaging modules comprise surface modifications of quantum dots (See e.g., Chan and Nie, Science 281:2016 (1998)) such as zinc sulfide-capped cadmium selenide coupled to biomolecules (Sooklal, Adv. Mater., 10:1083 (1998)).

In some embodiments, the imaging module comprises dendrimers produced according to the "nanocomposite" concept (See, e.g., Balogh et al., Proc. of ACS PMSE 77:118 (1997) and Balogh and Tomalia, J. Am. Che. Soc., 120:7355 (1998)). In these embodiments, dendrimers are produced by reactive encapsulation, where a reactant is preorganized by the dendrimer template and is then subsequently immobilized in/on the polymer molecule by a second reactant. Size, shape, size distribution and surface functionality of these nanoparticles are determined and controlled by the dendritic macromolecules. These materials have the solubility and compatibility of the host and have the optical or physiological properties of the guest molecule (i.e., the molecule that permits imaging). While the dendrimer host may vary according to the medium, it is possible to load the dendrimer hosts with different compounds and at various guest concentration levels. Complexes and composites may involve the use of a variety of metals or other inorganic materials. The high electron density of these materials considerably simplifies the imaging by electron microscopy and related scattering techniques. In addition, properties of inorganic atoms introduce new and measurable properties for imaging in either the presence or absence of interfering biological materials. In some embodiments of the present invention, encapsulation of gold, silver, cobalt, iron atoms/molecules and/or organic dye molecules such as fluorescein are encapsulated into dendrimers for use as nanoscopic composite labels/tracers, although any material that facilitates imaging or detection may be employed. In a preferred embodiment, the imaging agent is fluorescein isothiocyanate In some embodiments of the present invention, imaging is based on the passive or active observation of local differences in density of selected physical properties of the investigated complex matter. These differences may be due to a different shape (e.g., mass density detected by atomic force microscopy), altered composition (e.g. radiopaques detected by X-ray), distinct light emission (e.g., fluorochromes detected by spectrophotometry), different diffraction (e.g., electron-beam detected by TEM), contrasted absorption (e.g., light detected by optical methods), or special radiation emission (e.g., isotope methods), etc. Thus, quality and sensitivity of imaging depend on the property observed and on the technique used. The imaging techniques for cancerous cells have to provide sufficient levels of sensitivity to is observe small, local concentrations of selected cells. The earliest identification of cancer signatures requires high selectivity (i.e., highly specific recognition provided by appropriate targeting) and the highest possible sensitivity.

In some embodiments, once a targeted dendrimer conjugate has attached to (or been internalized into) a target cell (e.g., tumor cell and or inflammatory cell), one or more modules on the device serve to image its location. Dendrimers have already been employed as biomedical imaging agents, perhaps most notably for magnetic resonance imaging (MRI) contrast enhancement agents (See e.g., Wiener et al., Mag. Reson. Med. 31:1 (1994); an example using PAMAM dendrimers). These agents are typically constructed by conjugating chelated paramagnetic ions, such as Gd(III)-diethylen-etriaminepentaacetic acid (Gd(III)-DTPA), to water-soluble dendrimers. Other paramagnetic ions that may be useful in this context include, but are not limited to, gadolinium, manganese, copper, chromium, iron, cobalt, erbium, nickel, europium, technetium, indium, samarium, dysprosium, ruthenium, ytterbium, yttrium, and holmium ions and combinations thereof. In some embodiments of the present invention, a dendrimer conjugate is also conjugated to a targeting group, such as epidermal growth factor (EGF), to make the conjugate specifically bind to the desired cell type (e.g., in the case of EGF, EGFR-expressing tumor cells). In a preferred embodiment of the present invention, DTPA is attached to dendrimers via the isothiocyanate of DTPA as described by Wiener (Wiener et al., Mag. Reson. Med. 31:1 (1994)).

Dendrimeric MRI agents are particularly effective due to the polyvalency, size and architecture of dendrimers, which results in molecules with large proton relaxation enhancements, high molecular relaxivity, and a high effective concentration of paramagnetic ions at the target site. Dendrimeric gadolinium contrast agents have even been used to differentiate between benign and malignant breast tumors using dynamic MRI, based on how the vasculature for the latter type of tumor images more densely (Adam et al., Ivest. Rad. 31:26 (1996)). Thus, MRI provides a particularly useful imaging system of the present invention.

Static structural microscopic imaging of cancerous cells and tissues has traditionally been performed outside of the patient. Classical histology of tissue biopsies provides a fine illustrative example, and has proven a powerful adjunct to cancer diagnosis and treatment. After removal, a specimen is sliced thin (e.g., less than 40 microns), stained, fixed, and examined by a pathologist. If images are obtained, they are most often 2-D transmission bright-field projection images. Specialized dyes are employed to provide selective contrast, which is almost absent from the unstained tissue, and to also provide for the identification of aberrant cellular constituents.

Quantifying sub-cellular structural features by using computer-assisted analysis, such as in nuclear ploidy determination, is often confounded by the loss of histologic context owing to the thinness of the specimen and the overall lack of 3-D information. Despite the limitations of the static imaging approach, it has been invaluable to allow for the identification of neoplasia in biopsied tissue. Furthermore, its use is often the crucial factor in the decision to perform invasive and risky combinations of chemotherapy, surgical procedures, and radiation treatments, which are often accompanied by severe collateral tissue damage, complications, and even patient death.

A dendrimer conjugate of the present invention allows functional microscopic imaging of tumors and provide improved methods for imaging. The methods find use in vivo, in vitro, and ex vivo. For example, in one embodiment of the present invention, dendrimer conjugates of the present invention are designed to emit light or other detectable signals upon exposure to light. Although the labeled dendrimers may be physically smaller than the optical resolution limit of the microscopy technique, they become self-luminous objects when excited and are readily observable and measurable using optical techniques. In some embodiments of the present invention, sensing fluorescent biosensors in a microscope involves the use of tunable excitation and emission filters and multiwavelength sources (See, e.g., Farkas et al., SPEI 2678: 200 (1997)). In embodiments where the imaging agents are present in deeper tissue, longer wavelengths in the Near-infrared (NMR) are used (See e.g., Lester et al., Cell Mol. Biol. 44:29 (1998)). Dendrimeric biosensing in the Near-IR has been demonstrated with dendrimeric biosensing antenna-like architectures (See, e.g., Shortreed et al., J. Phys. Chem., 101:6318 (1997)). Biosensors that find use with the present invention include, but are not limited to, fluorescent dyes and molecular beacons.

In some embodiments of the present invention, in vivo imaging is accomplished using functional imaging techniques. Functional imaging is a complementary and potentially more powerful techniques as compared to static structural imaging. Functional imaging is best known for its application at the macroscopic scale, with examples including functional Magnetic Resonance Imaging (fMRI) and Positron Emission Tomography (PET). However, functional microscopic imaging may also be conducted and find use in in vivo and ex vivo analysis of living tissue. Functional microscopic imaging is an efficient combination of 3-D imaging, 3-D spatial multispectral volumetric assignment, and temporal sampling: in short a type of 3-D spectral microscopic movie loop. Interestingly, cells and tissues autofluoresce. When excited by several wavelengths, providing much of the basic 3-D structure needed to characterize several cellular components (e.g., the nucleus) without specific labeling. Oblique light illumination is also useful to collect structural information and is used routinely. As opposed to structural spectral microimaging, functional spectral microimaging may be used with biosensors, which act to localize physiologic signals within the cell or tissue. For example, in some embodiments of the present invention, biosensor-comprising dendrimers of the present invention are used to image upregulated receptor families such as the folate or EGF classes. In such embodiments, functional biosensing therefore involves the detection of physiological abnormalities relevant to carcinogenesis or malignancy, even at early stages. A number of physiological conditions may be imaged using the compositions and methods of the present invention including, but not limited to, detection of nanoscopic dendrimeric biosensors for pH, oxygen concentration, Ca$^2$+ concentration, and other physiologically relevant analytes.

In some embodiments, the present invention provides dendrimer conjugates (e.g., Baker-Huang PAMAM dendrimer conjugates) having a biological monitoring component. The biological monitoring or sensing component of a dendrimer conjugate of the present invention is one that can monitor the particular response in a target cell (e.g., tumor cell) induced by an agent (e.g., a therapeutic agent provided by the therapeutic component of the dendrimer conjugate). While the present invention is not limited to any particular monitoring system, the invention is illustrated by methods and compositions for monitoring cancer treatments. In preferred embodiments of the present invention, the agent induces apoptosis in cells and monitoring involves the detection of apoptosis. In particular embodiments, the monitoring component is an agent that fluoresces at a particular wavelength when apoptosis occurs. For example, in a preferred embodiment, caspase activity activates green fluorescence in the monitoring component. Apoptotic cancer cells, which have turned red as a result of being targeted by a particular signature with a red label, turn orange while residual cancer cells remain red. Normal cells induced to undergo apoptosis (e.g., through collateral damage), if present, will fluoresce green.

In these embodiments, fluorescent groups such as fluorescein are employed in the monitoring component. Fluorescein is easily attached to the dendrimer surface via the isothiocyanate derivatives, available from MOLECULAR PROBES, Inc. This allows the dendrimer conjugate to be imaged with the cells via confocal microscopy. Sensing of the effectiveness of the dendrimer conjugates is preferably achieved by using fluorogenic peptide enzyme substrates. For example, apoptosis caused by the therapeutic agents results in the production of the peptidase caspase-1 (ICE). CALBIOCHEM sells a number of peptide substrates for this enzyme that release a fluorescent moiety. A particularly useful peptide for use in the present invention is:

(SEQ ID NO: 1)
MCA-Tyr-Glu-Val-Asp-Gly-Trp-Lys-(DNP)-NH$_2$ where MCA is the (7-methoxycoumarin-4-yl)acetyl and DNP is the 2,4-dinitrophenyl group (See, e.g., Talanian et al., J. Biol. Chem., 272: 9677 (1997)). In this peptide, the MCA group has greatly attenuated fluorescence, due to fluorogenic resonance energy transfer (FRET) to the DNP group. When the enzyme cleaves the peptide between the aspartic acid and glycine residues, the MCA and DNP are separated, and the MCA group strongly fluoresces green (excitation maximum at 325 nm and emission maximum at 392 nm).

In some embodiments of the present invention, the lysine end of the peptide is linked to the dendrimer conjugate, so that the MCA group is released into the cytosol when it is cleaved. The lysine end of the peptide is a useful synthetic handle for conjugation because, for example, it can react with the activated ester group of a bifunctional linker such as Mal-PEG-OSu. Thus the appearance of green fluorescence in the target cells produced using these methods provides a clear indication that apoptosis has begun (if the cell already has a red color from the presence of aggregated quantum dots, the cell turns orange from the combined colors).

Additional fluorescent dyes that find use with the present invention include, but are not limited to, acridine orange, reported as sensitive to DNA changes in apoptotic cells (Abrams et al., Development 117:29 (1993)) and cis-parinaric acid, sensitive to the lipid peroxidation that accompanies apoptosis (Hockenbery et al., Cell 75:241 (1993)). It should be noted that the peptide and the fluorescent dyes are merely exemplary. It is contemplated that any peptide that effectively acts as a substrate for a caspase produced as a result of apoptosis finds use with the present invention.

In some embodiments, conjugation between a dendrimer (e.g., terminal arm of a dendrimer) and a functional group or between functional groups is accomplished through use of a 1,3-dipolar cycloaddition reaction ("click chemistry"). 'Click chemistry' involves, for example, the coupling of two different moieties (e.g., a therapeutic agent and a functional group) (e.g., a first functional group and a second functional group) via a 1,3-dipolar cycloaddition reaction between an alkyne moiety (or equivalent thereof) on the surface of the first moeity and an azide moiety (e.g., present on a triazine composition) (or equivalent thereof) (or any active end group such as, for example, a primary amine end group, a hydroxyl end group, a carboxylic acid end group, a thiol end group, etc.) on the second moiety (see, e.g., U.S. Provisional Patent App. No. 61/140,480, herein incorporated by reference in its entirety. 'Click' chemistry is an attractive coupling method because, for example, it can be performed with a wide variety of solvent conditions including aqueous environments. For example, the stable triazole ring that results from coupling the alkyne with the azide is frequently achieved at quantitative yields and is considered to be biologically inert (see, e.g., Rostovtsev, V. V.; et al., Angewandte Chemie-International Edition 2002, 41, (14), 2596; Wu, P.; et al., Angewandte Chemie-International Edition 2004, 43, (30), 3928-3932; each herein incorporated by reference in their entireties).

In some embodiments, conjugation between a dendrimer (e.g., a terminal arm of a dendrimer) and a functional ligand is accomplished during a "one-pot" reaction. The term "one-pot synthesis reaction" or equivalents thereof, e.g., "1-pot", "one pot", etc., refers to a chemical synthesis method in which all reactants are present in a single vessel. Reactants may be added simultaneously or sequentially, with no limitation as to the duration of time elapsing between introduction of sequentially added reactants. In some embodiments, a one-pot reaction occurs wherein a hydroxyl-terminated dendrimer (e.g., HO-PAMAM dendrimer) is reacted with one or more functional ligands (e.g., a therapeutic agent, a pro-drug, a trigger agent, a targeting agent, an imaging agent) in one vessel, such conjugation being facilitated by ester coupling agents (e.g., 2-chloro-1-methylpyridinium iodide and 4-(dimethylamino)pyridine) (see, e.g., U.S. Provisional Patent App. No. 61/226,993, herein incorporated by reference in its entirety).

Functionalized nanoparticles (e.g., dendrimers) often contain moieties (including but not limited to ligands, functional ligands, conjugates, therapeutic agents, targeting agents, imaging agents, fluorophores) that are conjugated to the periphery. Such moieties may for example be conjugated to one or more dendrimer branch termini. Classical multi-step conjugation strategies used during the synthesis of functionalized dendrimers generate a stochastic distribution of products with differing numbers of ligands attached per dendrimer molecule, thereby creating a population of dendrimers with a wide distribution in the numbers of ligands attached. The low structural uniformity of such dendrimer populations negatively affects properties such as therapeutic potency, pharmacokinetics, or effectiveness for multivalent targeting. Difficulties in quantifying and resolving such populations to yield samples with sufficient structural uniformity can pose challenges. However, in some embodiments, use of separation methods (e.g., reverse phase chromatography) customized for optimal separation of dendrimer populations in conjunction with peak fitting analysis methods allows isolation and identification of subpopulations of functionalized dendrimers with high structural uniformity (see, e.g., U.S. Provisional Pat. App. No. 61/237,172; herein incorporated by reference in its entirety). In certain embodiments, such methods and systems provide a dendrimer product made by the process comprising: a) conjugation of at least one ligand type to a dendrimer to yield a population of ligand-conjugated dendrimers; b) separation of the population of ligand-conjugated dendrimers with reverse phase HPLC to result in subpopulations of ligand-conjugated dendrimers indicated by a chromatographic trace; and c) application of peak fitting analysis to the chromatographic trace to identify subpopulations of ligand-conjugated dendrimers wherein the structural uniformity of ligand conjugates per molecule of dendrimer within said subpopulation is, e.g., approximately 80% or more.

As described above, another component of the present invention is that the dendrimer conjugate compositions are able to specifically target a particular tissue region and/or cell type (e.g., CNS). In some embodiments, the dendrimer conjugate targets the CNS (e.g., via transferrin), neurons within the CNS (e.g., via Tet1), the peripheral nervous system, muscles, and/or nerves.

In some embodiments of the present invention, targeting groups are conjugated to dendrimers and/or linkers conjugated to the dendrimers with either short (e.g., direct coupling), medium (e.g. using small-molecule bifunctional linkers such as SPDP, sold by PIERCE CHEMICAL Company), or long (e.g., PEG bifunctional linkers, sold by NEKTAR, Inc.) linkages. Since dendrimers have surfaces with a large number of functional groups, more than one targeting group and/or linker may be attached to each dendrimer. As a result, multiple binding events may occur between the dendrimer conjugate and the target cell. In these embodiments, the dendrimer conjugates have a very high affinity for their target cells via this "cooperative binding" or polyvalent interaction effect.

For steric reasons, in some embodiments, the smaller the ligands, the more can be attached to the surface of a dendrimer and/or linkers attached thereto. Recently, Wiener reported that dendrimers with attached folic acid would specifically accumulate on the surface and within tumor cells expressing the high-affinity folate receptor (hFR) (See, e.g., Wiener et al., Invest. Radiol., 32:748 (1997)). The hFR receptor is expressed or upregulated on epithelial tumors, including breast cancers. Control cells lacking hFR showed no significant accumulation of folate-derivatized dendrimers. Folic acid can be attached to full generation PAMAM dendrimers via a carbodiimide coupling reaction. Folic acid is a good targeting candidate for the dendrimers, with its small size and a simple conjugation procedure.

Antibodies can be generated to allow for the targeting of antigens or immunogens (e.g., tumor, tissue or pathogen specific antigens) on various biological targets (e.g., pathogens, tumor cells, normal tissue). Such antibodies include, but are not limited to polyclonal, monoclonal, chimeric, single chain, Fab fragments, and an Fab expression library.

In some embodiments, the antibodies recognize tumor specific epitopes (e.g., TAG-72 (See, e.g., Kjeldsen et al., Cancer Res. 48:2214-2220 (1988); U.S. Pat. Nos. 5,892,020; 5,892,019; and 5,512,443); human carcinoma antigen (See, e.g., U.S. Pat. Nos. 5,693,763; 5,545,530; and 5,808,005); TP1 and TP3 antigens from osteocarcinoma cells (See, e.g., U.S. Pat. No. 5,855,866); Thomsen-Friedenreich (TF) antigen from adenocarcinoma cells (See, e.g., U.S. Pat. No. 5,110, 911); "KC-4 antigen" from human prostrate adenocarcinoma (See, e.g., U.S. Pat. Nos. 4,708,930 and 4,743,543); a human colorectal cancer antigen (See, e.g., U.S. Pat. No. 4,921,789); CA125 antigen from cystadenocarcinoma (See, e.g., U.S. Pat. No. 4,921,790); DF3 antigen from human breast carcinoma (See, e.g., U.S. Pat. Nos. 4,963,484 and 5,053,489); a human breast tumor antigen (See, e.g., U.S. Pat. No. 4,939,240); p97 antigen of human melanoma (See, e.g., U.S. Pat. No. 4,918, 164); carcinoma or orosomucoid-related antigen (CORA) (See, e.g., U.S. Pat. No. 4,914,021); a human pulmonary carcinoma antigen that reacts with human squamous cell lung carcinoma but not with human small cell lung carcinoma (See, e.g., U.S. Pat. No. 4,892,935); T and Tn haptens in glycoproteins of human breast carcinoma (See, e.g., Springer et al., Carbohydr. Res. 178:271-292 (1988)), MSA breast carcinoma glycoprotein termed (See, e.g., Tjandra et al., Br. J. Surg. 75:811-817 (1988)); MFGM breast carcinoma antigen (See, e.g., Ishida et al., Tumor Biol. 10:12-22 (1989)); DU-PAN-2 pancreatic carcinoma antigen (See, e.g., Lan et al., Cancer Res. 45:305-310 (1985)); CA125 ovarian carcinoma antigen (See, e.g., Hanisch et al., Carbohydr. Res. 178:29-47 (1988)); YH206 lung carcinoma antigen (See, e.g., Hinoda et al., (1988) Cancer J. 42:653-658 (1988)). Each of the foregoing references are specifically incorporated herein by reference.

Various procedures known in the art are used for the production of polyclonal antibodies. For the production of antibody, various host animals can be immunized by injection with the peptide corresponding to the desired epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants are used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies, any technique that provides for the production of antibody molecules by continuous cell lines in culture may be used (See e.g., Harlow and Lane, Antibodies: A Laboratory Manual, Cold Spring Harbor Laboratory Press, Cold Spring Harbor, N.Y.). These include, but are not limited to, the hybridoma technique originally developed by Kohler and Milstein (Kohler and Milstein, Nature 256:495-497 (1975)), as well as the trioma technique, the human B-cell hybridoma technique (See e.g., Kozbor et al. Immunol. Today 4:72 (1983)), and the EBV-hybridoma technique to produce human monoclonal antibodies (Cole et al., in Monoclonal Antibodies and Cancer Therapy, Alan R. Liss, Inc., pp. 77-96 (1985)).

In an additional embodiment of the invention, monoclonal antibodies can be produced in germ-free animals utilizing recent technology (See e.g., PCT/US90/02545). According to the invention, human antibodies may be used and can be obtained by using human hybridomas (Cote et al., Proc. Natl. Acad. Sci. U.S.A. 80:2026-2030 (1983)) or by transforming human B cells with EBV virus in vitro (Cole et al., in Monoclonal Antibodies and Cancer Therapy, Alan R. Liss, pp. 77-96 (1985)).

According to the invention, techniques described for the production of single chain antibodies (U.S. Pat. No. 4,946, 778; herein incorporated by reference) can be adapted to produce specific single chain antibodies. An additional embodiment of the invention utilizes the techniques described for the construction of Fab expression libraries (Huse et al., Science 246:1275-1281 (1989)) to allow rapid and easy identification of monoclonal Fab fragments with the desired specificity.

Antibody fragments that contain the idiotype (antigen binding region) of the antibody molecule can be generated by known techniques. For example, such fragments include but are not limited to: the F(ab')2 fragment that can be produced by pepsin digestion of the antibody molecule; the Fab' fragments that can be generated by reducing the disulfide bridges of the F(ab')2 fragment, and the Fab fragments that can be generated by treating the antibody molecule with papain and a reducing agent.

In the production of antibodies, screening for the desired antibody can be accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, and immunoelectrophoresis assays, etc.).

The dendrimer conjugates of the present invention have many advantages over liposomes, such as their greater stability, better control of their size and polydispersity, and generally lower toxicity and immunogenicity (See e.g., Duncan et al, Polymer Preprints 39:180 (1998)). Thus, in some embodiments of the present invention, anti-HER2 antibody fragments, as well as other targeting antibodies are conjugated to dendrimers, as targeting agents for the nanodevices of the present invention.

The bifunctional linkers SPDP and SMCC and the longer Mal-PEG-OSu linkers are particularly useful for antibody-dendrimer conjugation. In addition, many tumor cells contain surface lectins that bind to oligosaccharides, with specific recognition arising chiefly from the terminal carbohydrate residues of the latter (See, e.g., Sharon and Lis, Science 246:227 (1989)). Attaching appropriate monosaccharides to nonglycosylated proteins such as BSA provides a conjugate that binds to tumor lectin much more tightly than the free monosaccharide (See, e.g., Monsigny et al., Biochemie 70:1633 (1988)).

Mannosylated PAMAM dendrimers bind mannoside-binding lectin up to 400 more avidly than monomeric mannosides (See, e.g., Page and Roy, Bioconjugate Chem., 8:714 (1997)). Sialylated dendrimers and other dendritic polymers bind to and inhibit a variety of sialate-binding viruses both in vitro and in vivo. By conjugating multiple monosaccharide residues (e.g., α-galactoside, for galactose-binding cells) to dendrimers, polyvalent conjugates are created with a high affinity for the corresponding type of tumor cell. The attachment reaction are easily carried out via reaction of the terminal amines with commercially-available α-galactosidyl-phenylisothiocyanate. The small size of the carbohydrates allows a high concentration to be present on the dendrimer surface.

Related to the targeting approaches described above is the "pretargeting" approach (See e.g., Goodwin and Meares, Cancer (suppl.) 80:2675 (1997)). An example of this strategy involves initial treatment of a subject with conjugates of tumor-specific monoclonal antibodies and streptavidin. Remaining soluble conjugate is removed from the bloodstream with an appropriate biotinylated clearing agent. When the tumor-localized conjugate is all that remains, a radiolabeled, biotinylated agent is introduced, which in turn localizes at the tumor sites by the strong and specific biotin-streptavidin interaction. Thus, the radioactive dose is maximized in dose proximity to the cancer cells and minimized in the rest of the body where it can harm healthy cells.

It has been shown that if streptavidin molecules bound to a polystyrene well are first treated with a biotinylated dendrimer, and then radiolabeled streptavidinis introduced, up to four of the labeled streptavidin molecules are bound per polystyrene-bound streptavidin (See, e.g., Wilbur et al., Bioconjugate Chem., 9:813 (1998)). Thus, biotinylated dendrimers may be used in the methods of the present invention, acting as a polyvalent receptor for the radiolabel in vivo, with a resulting amplification of the radioactive dosage per bound antibody conjugate. In the preferred embodiments of the present invention, one or more multiply-biotinylated module(s) on the clustered dendrimer presents a polyvalent target for radiolabeled or boronated (See, e.g., Barth et al., Cancer Investigation 14:534 (1996)) avidin or streptavidin, again resulting in an amplified dose of radiation for the tumor cells.

Dendrimers may also be used as clearing agents by, for example, partially biotinylating a dendrimer that has a polyvalent galactose or mannose surface. The conjugate-clearing agent complex would then have a very strong affinity for the corresponding hepatocyte receptors.

In other embodiments of the present invention, an enhanced permeability and retention (EPR) method is used in targeting. The enhanced permeability and retention (EPR) effect is a more "passive" way of targeting tumors (See, e.g., Duncan and Sat, Ann. Oncol., 9:39 (1998)). The EPR effect is the selective concentration of macromolecules and small particles in the tumor microenvironment, caused by the hyperpermeable vasculature and poor lymphatic drainage of tumors. The dendrimer compositions of the present invention provide ideal polymers for this application, in that they are relatively rigid, of narrow polydispersity, of controlled size and surface chemistry, and have interior "cargo" space that can carry and then release antitumor drugs. In fact, PAMAM dendrimer-platinates have been shown to accumulate in solid tumors (Pt levels about 50 times higher than those obtained with cisplatin) and have in vivo activity in solid tumor models for which cisplatin has no effect (See, e.g., Malik et al., Proc. Int'l. Symp. Control. Rel. Bioact. Mater., 24:107 (1997) and Duncan et al., Polymer Preprints 39:180 (1998)).

The dendrimers (e.g., Baker-Huang PAMAM dendrimers) may be characterized for size and uniformity by any suitable analytical techniques. These include, but are not limited to, atomic force microscopy (AFM), electrospray-ionization mass spectroscopy, MALDI-TOF mass spectroscopy, $^{13}C$ nuclear magnetic resonance spectroscopy, high performance liquid chromatography (HPLC) size exclusion chromatography (SEC) (equipped with multi-angle laser light scattering, dual UV and refractive index detectors), capillary electrophoresis and get electrophoresis. These analytical methods assure the uniformity of the dendrimer population and are important in the quality control of dendrimer production for eventual use in in vivo applications. Most importantly, extensive work has been performed with dendrimers showing no evidence of toxicity when administered intravenously (Roberts et al., J. Biomed. Mater. Res., 30:53 (1996) and Boume et al., J. Magnetic Resonance Imaging, 6:305 (1996)).

In some embodiments of the present invention, the dendrimer conjugates comprise transgenes for delivery and expression to a target cell or tissue, in vitro, ex vivo, or in vivo. In such embodiments, rather than containing the actual protein, the dendrimer complex comprises an expression vector construct containing, for example, a heterologous DNA encoding a gene of interest and the various regulatory elements that facilitate the production of the particular protein of interest in the target cells.

In some embodiments, the gene is a therapeutic gene that is used, for example, to treat cancer, to replace a defective gene, or a marker or reporter gene that is used for selection or monitoring purposes. In the context of a gene therapy vector, the gene may be a heterologous piece of DNA. The heterologous DNA may be derived from more than one source (i.e., a multigene construct or a fusion protein). Further, the heterologous DNA may include a regulatory sequence derived from one source and the gene derived from a different source.

Tissue-specific promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. Similarly, promoters may be used to target gene expression in other tissues (e.g., insulin, elastin amylase, pdr-1, pdx-1 and glucokinase promoters target to the pancreas; albumin PEPCK, HBV enhancer, alpha fetoproteinapolipoprotein C, alpha-1 antitrypsin, vitellogenin, NF-AB and transthyretin promoters target to the liver; myosin H chain, muscle creatine kinase, dystrophin, calpain p94, skeletal alpha-actin, fast troponin 1 promoters target to skeletal muscle; keratin promoters target the skin; sm22 alpha; SM-α-actin promoters target smooth muscle; CFTR; human cytokeratin 18 (K18); pulmonary surfactant proteins A, B and Q CC-10; P1 promoters target lung tissue; endothelin-1; E-selectin; von Willebrand factor; KDR/flk-1 target the endothelium; tyrosinase targets melanocytes).

The nucleic acid may be either cDNA or genomic DNA. The nucleic acid can encode any suitable therapeutic protein. Preferably, the nucleic acid encodes a tumor suppressor, cytokine, receptor, inducer of apoptosis, or differentiating agent. The nucleic acid may be an antisense nucleic acid. In such embodiments, the antisense nucleic acid may be incorporated into the nanodevice of the present invention outside of the context of an expression vector.

In preferred embodiments, the nucleic acid encodes a tumor suppressor, cytokines, receptors, or inducers of apoptosis. Suitable tumor suppressors include BRCA1, BRCA2, C-CAM, p16, p211 p53, p73, or Rb. Suitable cytokines include GMCSF, IL-1, IL-2, IL-3, IL-4, IL-5, IL6, IL-7, IL-8, IL-9, IL-10, IL-11, IL-12, IL-13, IL-14, IL-15, β-interferon, γ-interferon, or TNF. Suitable receptors include CFTR, EGFR, estrogen receptor, IL-2 receptor, or VEGFR. Suitable inducers of apoptosis include AdE1B, Bad, Bak, Bax, Bid, Bik, Bim, Harakiri, or ICE-CED3 protease.

In some embodiments, more than one administration of the dendrimer conjugates of the present invention or the other agent are utilized. Various combinations may be employed, where the dendrimer is "A" (e.g., comprising a therapeutic agent) and the other agent is "B" (e.g., comprising a therapeutic agent antagonist), as exemplified below:

A/B/A, B/A/B, B/B/A, A/A/B, B/A/A, A/B/B, B/B/B/A, B/B/A/B,
A/B/B, A/B/A/B, B/B/A, B/B/A/A, B/A/B/A, B/A/A/B, B/B/B/A,
A/A/A/B, B/A/A/A, A/B/A/A, A/A/B/A, A/B/B/B, B/A/B/B, B/B/A/B.

Other combinations are contemplated.

Other factors that may be used in combination therapy with the dendrimer conjugates of the present invention include, but are not limited to, factors that cause DNA damage such as gamma-rays, X-rays, and/or the directed delivery of radioisotopes to tumor cells. Other forms of DNA damaging factors are also contemplated such as microwaves and UV-irradiation. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells. The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

In preferred embodiments of the present invention, the regional delivery of the dendrimer conjugates to patients with cancers is utilized to maximize the therapeutic effectiveness of the delivered agent. Similarly, the chemo- or radiotherapy may be directed to particular, affected region of the subjects body. Alternatively, systemic delivery of the immunotherapeutic composition and/or the agent may be appropriate in certain circumstances, for example, where extensive metastasis has occurred.

In addition to combining the dendrimer conjugates with chemo- and radiotherapies, it also is contemplated that traditional gene therapies are used. For example, targeting of p53 or p16 mutations along with treatment of the dendrimer conjugates provides an improved anti-cancer treatment. The present invention contemplates the co-treatment with other tumor-related genes including, but not limited to, p21, Rb, APC, DCC, NF-I, NF-2, BCRA2, p16, FHIT, WT-I, MEN-1, MEN-II, BRCA1, VHL, FCC, MCC, ras, myc, neu, raf erb, src, fms, jun, trk, ret, gsp, hst, bcl, and abl.

In vivo and ex vivo treatments are applied using the appropriate methods worked out for the gene delivery of a particular construct for a particular subject. For example, for viral vectors, one typically delivers $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies.

An attractive feature of the present invention is that the therapeutic compositions may be delivered to local sites in a patient by a medical device. Medical devices that are suitable for use in the present invention include known devices for the localized delivery of therapeutic agents. Such devices include, but are not limited to, catheters such as injection catheters, balloon catheters, double balloon catheters, microporous balloon catheters, channel balloon catheters, infusion catheters, perfusion catheters, etc., which are, for example, coated with the therapeutic agents or through which the agents are administered; needle injection devices such as hypodermic needles and needle injection catheters; needleless injection devices such as jet injectors; coated stents, bifurcated stents, vascular grafts, stent grafts, etc.; and coated vaso-occlusive devices such as wire coils.

Exemplary devices are described in U.S. Pat. Nos. 5,935,114; 5,908,413; 5,792,105; 5,693,014; 5,674,192; 5,876,445; 5,913,894; 5,868,719; 5,851,228; 5,843,089; 5,800,519; 5,800,508; 5,800,391; 5,354,308; 5,755,722; 5,733,303; 5,866,561; 5,857,998; 5,843,003; and 5,933,145; the entire contents of which are incorporated herein by reference. Exemplary stents that are commercially available and may be used in the present application include the RADIUS (SCIMED LIFE SYSTEMS, Inc.), the SYMPHONY (Boston Scientific Corporation), the Wallstent (Schneider Inc.), the PRECEDENT II (Boston Scientific Corporation) and the NIR (Medinol Inc.). Such devices are delivered to and/or implanted at target locations within the body by known techniques.

In some embodiments, the therapeutic complexes of the present invention comprise a photodynamic compound and a targeting agent that is administered to a patient. In some embodiments, the targeting agent is then allowed a period of time to bind the "target" cell (e.g. about 1 minute to 24 hours) resulting in the formation of a target cell-target agent complex. In some embodiments, the therapeutic complexes comprising the targeting agent and photodynamic compound are then illuminated (e.g., with a red laser, incandescent lamp, X-rays, or filtered sunlight). In some embodiments, the light is aimed at the jugular vein or some other superficial blood or lymphatic vessel. In some embodiments, the singlet oxygen and free radicals diffuse from the photodynamic compound to the target cell (e.g. cancer cell or pathogen) causing its destruction.

Where clinical applications are contemplated, in some embodiments of the present invention, the dendrimer conjugates are prepared as part of a pharmaceutical composition in a form appropriate for the intended application. Generally, this entails preparing compositions that are essentially free of pyrogens, as well as other impurities that could be harmful to humans or animals. However, in some embodiments of the present invention, a straight dendrimer formulation may be administered using one or more of the routes described herein.

In preferred embodiments, the dendrimer conjugates are used in conjunction with appropriate salts and buffers to render delivery of the compositions in a stable manner to allow for uptake by target cells. Buffers also are employed when the dendrimer conjugates are introduced into a patient. Aqueous compositions comprise an effective amount of the dendrimer conjugates to cells dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. Except insofar as any conventional media or agent is incompatible with the vectors or cells of the present invention, its use in therapeutic compositions is contemplated. Supplementary active ingredients may also be incorporated into the compositions.

In some embodiments of the present invention, the active compositions include classic pharmaceutical preparations. Administration of these compositions according to the present invention is via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection.

The active dendrimer conjugates may also be administered parenterally or intraperitoneally or intratumorally. Solutions of the active compounds as free base or pharmacologically acceptable salts are prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

In some embodiments, a therapeutic agent is released from dendrimer conjugates within a target cell (e.g., within an endosome). This type of intracellular release (e.g., endosomal disruption of a linker-therapeutic conjugate) is contemplated to provide additional specificity for the compositions and methods of the present invention. In some embodiments, the dendrimer conjugates of the present invention contain between 100-150 primary amines on the surface. Thus, the present invention provides dendrimers with multiple (e.g., 100-150) reactive sites for the conjugation of linkers and/or functional groups comprising, but not limited to, therapeutic agents, targeting agents, imaging agents and biological monitoring agents.

The compositions and methods of the present invention are contemplated to be equally effective whether or not the dendrimer conjugates of the present invention comprise a fluorescein (e.g. FITC) imaging agent. Thus, each functional group present in a dendrimer composition is able to work independently of the other functional groups. Thus, the present invention provides dendrimer conjugates that can comprise multiple combinations of targeting, therapeutic, imaging, and biological monitoring functional groups. Additionally, in some embodiments, each functional group (e.g., therapeutic agents, targeting agents, imaging agents and biological monitoring agents) present in a dendrimer composition can function together with one or more of the functional groups (e.g., cooperative binding of multiple targeting ligands).

The present invention also provides a very effective and specific method of delivering molecules (e.g., therapeutic and imaging functional groups) to the interior of target cells (e.g., cancer cells). Thus, in some embodiments, the present invention provides methods of therapy that comprise or require delivery of molecules into a cell in order to function (e.g., delivery of genetic material such as siRNAs).

The pharmaceutical forms suitable for injectable use include sterile aqueous solutions or dispersions and sterile powders for the extemporaneous preparation of sterile injectable solutions or dispersions. The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it may be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, dendrimer conjugates are administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution is suitably buffered, if necessary, and the liquid diluent first rendered isotonic with sufficient saline or glucose. These particular aqueous solutions are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). In some embodiments of the present invention, the active particles or agents are formulated within a therapeutic mixture to comprise about 0.0001 to 1.0 milligrams, or about 0.001 to 0.1 milligrams, or about 0.1 to 1.0 or even about 10 milligrams per dose or so. Multiple doses may be administered.

Additional formulations that are suitable for other modes of administration include vaginal suppositories and pessaries. A rectal pessary or suppository may also be used. Suppositories are solid dosage forms of various weights and shapes, usually medicated, for insertion into the rectum, vagina or the urethra. After insertion, suppositories soften, melt or dissolve in the cavity fluids. In general, for suppositories, traditional binders and carriers may include, for example, polyalkylene glycols or triglycerides; such suppositories may be formed from mixtures containing the active ingredient in the range of 0.5% to 10%, preferably 1%-2%. Vaginal suppositories or pessaries are usually globular or oviform and weighing about 5 g each. Vaginal medications are available in a variety of physical forms, e.g., creams, gels or liquids, which depart from the classical concept of suppositories. In addition, suppositories may be used in connection with colon cancer. The dendrimer conjugates also may be formulated as inhalants for the treatment of lung cancer and such like.

The present invention also includes methods involving co-administration of the multifunctional dendrimers and components thereof described herein with one or more additional active agents. Indeed, it is a further aspect of this invention to provide methods for enhancing prior art therapies and/or pharmaceutical compositions by co-administering multifunctional dendrimers of this invention. In co-administration procedures, the agents may be administered concurrently or sequentially. In some embodiments, the multifunctional dendrimers described herein are administered prior to the other active agent(s). The agent or agents to be co-administered depends on the type of condition being treated. For example, when the condition being treated is cancer, the additional agent can be a chemotherapeutic agent or radiation. The additional agents to be co-administered, such as anticancer agents, can be any of the well-known agents in the art, including, but not limited to, those that are currently in clinical use. The determination of appropriate type and dosage of radiation treatment is also within the skill in the art or can be determined with relative ease.

Where clinical applications are contemplated, in some embodiments of the present invention, the dendrimer conjugates are prepared as part of a pharmaceutical composition in a form appropriate for the intended application. Generally, this entails preparing compositions that are essentially free of pyrogens, as well as other impurities that could be harmful to humans or animals. However, in some embodiments of the present invention, a straight dendrimer formulation may be administered using one or more of the routes described herein. It is contemplated that the present therapy can be employed in the treatment of any pathogenic disease for which a specific signature has been identified or which can be targeted for a given pathogen. Examples of pathogens contemplated to be treatable with the methods of the present invention include, but are not limited to, *Legionella peomophilia, Mycobacterium tuberculosis, Clostridium tetani, Hemophilus influenzae, Neisseria gonorrhoeae, Treponema pallidum, Bacillus anthracis, Vibrio cholerae, Borrelia burgdorferi, Cornebacterium diphtheria, Staphylococcus aureus*, human papilloma virus, human immunodeficiency virus, rubella virus, polio virus, and the like.

In some embodiments, the present invention also provides kits comprising one or more of the reagents and tools necessary to generate a dendrimer conjugated with one or more triazine compositions (e.g., scaffolds) (e.g., triazine compositions capable of click chemistry for use in one-step synthesis of functionalized dendrimers) (e.g., triazine compositions having one or more functional groups), and methods of using such dendrimers.

EXPERIMENTAL

The following examples are provided in order to demonstrate and further illustrate certain preferred embodiments and aspects of the present invention and are not to be construed as limiting the scope thereof.

Example 1

Previous experiments involving dendrimer related technologies are located in U.S. Pat. Nos. 6,471,968, 7,078,461; U.S. patent application Ser. Nos. 09/940,243, 10/431,682, 11,503,742, 11,661,465, 11/523,509, 12/403,179, 12/106, 876, 11/827,637, 10/039,393, 10/254,126, 09/867,924, 12/570,977, and Ser. No. 12/645,081; U.S. Provisional Patent Application Ser. Nos. 61/140,480, 61/091,608, 61/097,780, 61/101,461, 60/604,321, 60/690,652, 60/707,991, 60/208, 728, 60/718,448, 61/035,949, 60/830,237, and 60/925,181; and International Patent Application Nos. PCT/US2010/ 050893, PCT/US2010/042556, PCT/US2001/015204, PCT/ US2005/030278, PCT/US2009/069257, PCT/US2009/ 036992, PCT/US2009/059071, PCT/US2007/015976, and PCT/US2008/061023, each herein incorporated by reference in their entireties.

Example 2

Synthesis of an $AB_2$ Branch Unit

Figure 7:
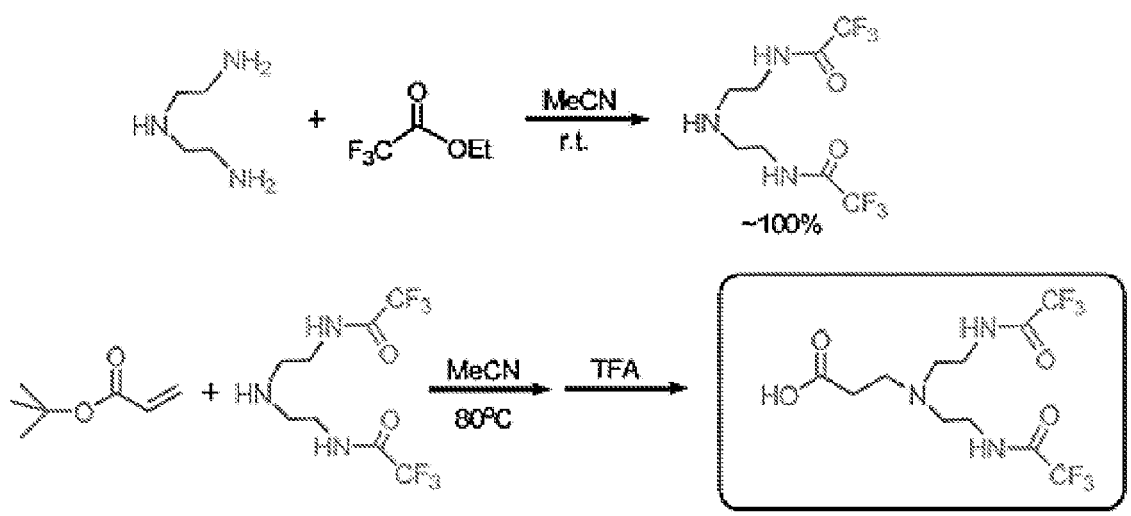
FIG. 7 shows a synthesis scheme for one embodiment of an $AB_2$ branch unit of the present invention.
Figure 11:
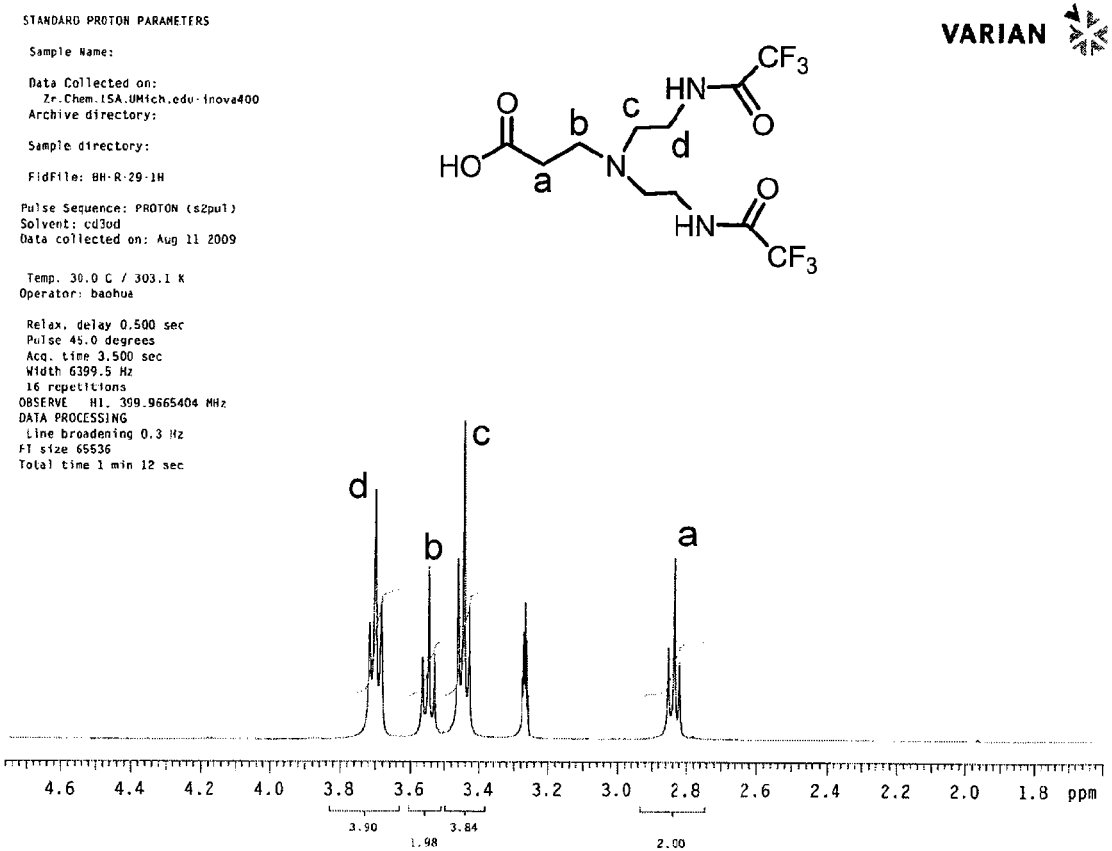
FIG. 11 shows an NMR spectrum generated using one embodiment of an $AB_2$ branching unit of the present invention, as illustrated on the spectrum.
Figure 12:
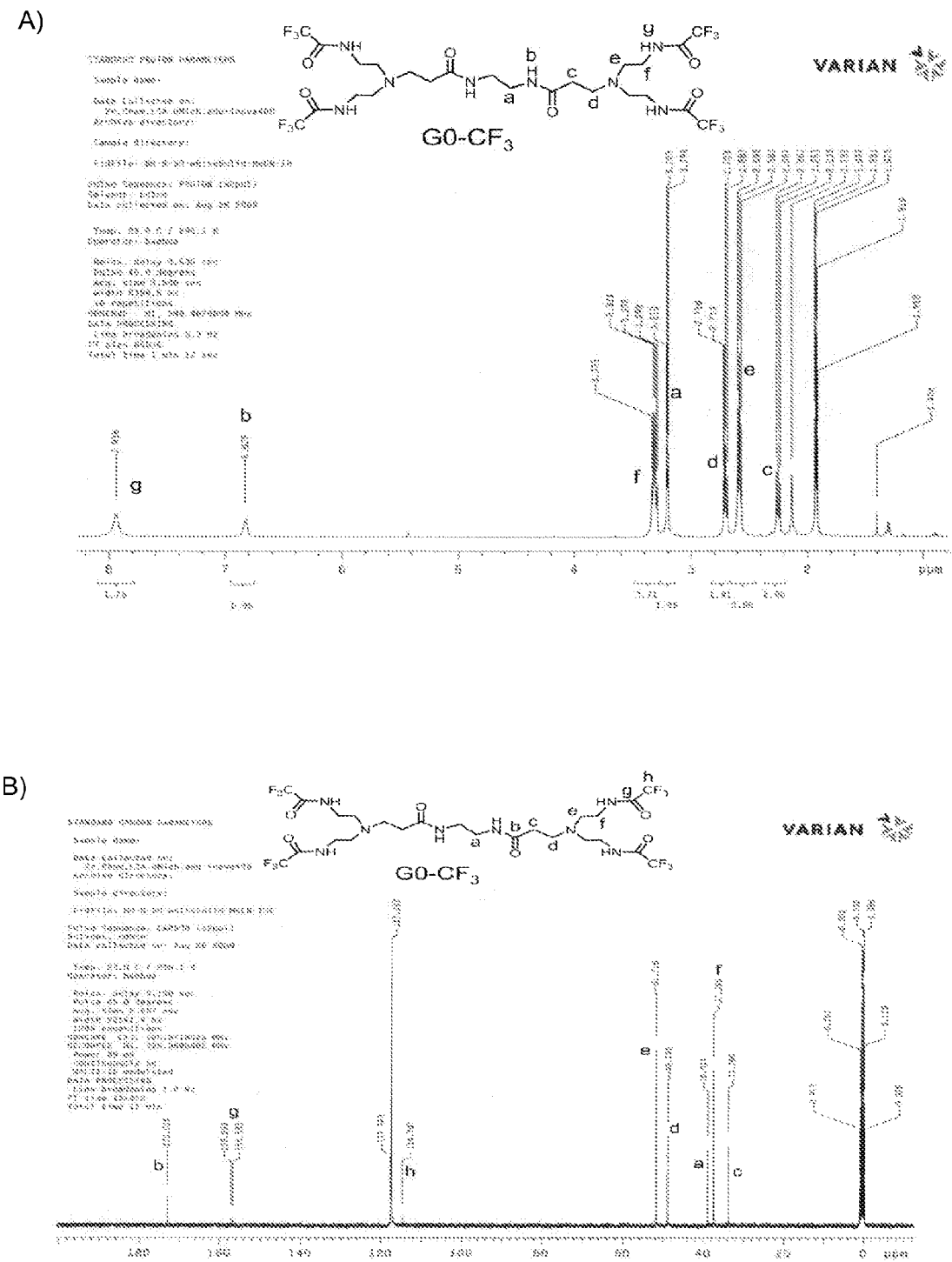
FIG. 12 shows an NMR spectrum generated using one embodiment of a generation 0 (G0) $CF_3$-terminated Baker-Huang PAMAM dendrimer of the present invention, as illustrated on the spectrum. Panel A, approximately 8 ppm to 0 ppm; panel B, approximately 200 ppm to 0 ppm.

A synthesis scheme of one embodiment of an $AB_2$ branch unit is shown in FIG. 7. In this scheme, diethylene triamine was used as the branch; TREN is a industrial material that can be purchased in large quantities; and ethyl trifluoro acetate was used as an amine protection reagent. Ethyl trifluoro acetate protects primary amines preferentially, but not secondary amine. Therefore, two equivalents of trifluoro acetate were reacted with TREN to give the protected TREN in almost quantitative yield. Thereafter, this secondary amine was reacted with t-butyl acrylate through Michael addition to give the $AB_2$ branch unit upon TFA treatment, to expose the carboxylic acid. An NMR spectrum showing structural analysis of the $AB_2$ branch unit is shown in FIG. 11.

Example 2

Synthesis of a Baker-Huang PAMAM Dendrimer

Figure 8:
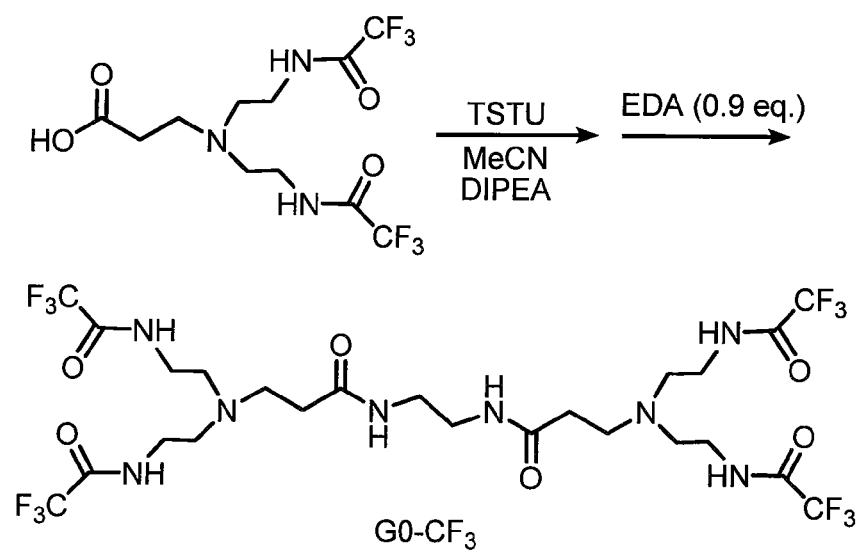
FIG. 8 shows a synthesis scheme for one embodiment of a generation 0 (G0), $CF_3$-terminated dendrimer (Baker-Huang dendrimer) of the present invention.

FIG. 8 shows a reaction scheme used to synthesize a G0 Baker-Huang PAMAM dendrimer. Several different synthetic approaches were attempted. First, an attempt was made to make the acid chloride from the carboxylic acid, upon reaction of the $AB_2$ branch unit with thionyl chloride. However, the molecule decomposed. Thereafter, an attempt was made to activate the acid to its NHS ester with TSTU (O—(N-succinimidyl)-1,1,3,3-tetramethyluronium tetrafluoroborate), and then EDA was added to the activated ester. A crude mass spectromatogram showed presence of a high product peak.

Several different approaches were taken in an attempt to purify the product. In the reaction mixture, DIPEA and the remaining TSTU persist as small molecules. Reverse-phase HPLC was conducted; however, the material remained on the column and never washed out. In another approach, the reaction mixture was stored at 4° C. in dichloromethane, resulting in precipitation of solid material after several days of storage. While the present invention is not limited to any particular mechanism, and an understanding of the mechanism is not necessary to practice the present invention, it was contemplated that since the molecular weight of the protected G1 Baker-Huang dendrimer is 750, it might be possible to remove small molecules by dialysis using a 500 Dalton membrane. Upon addition of water to the crude material, white solid precipitated from solution. Subsequent analysis by C-NMR, H-NMR, MS, and HPLC showed that the white solid is the G0 dendrimer. The white solid was washed with water several times, and NMR and HPLC showed a high level of purity (FIGS. 12A and 12B, FIG. 14, FIG. 16).

Figure 9:
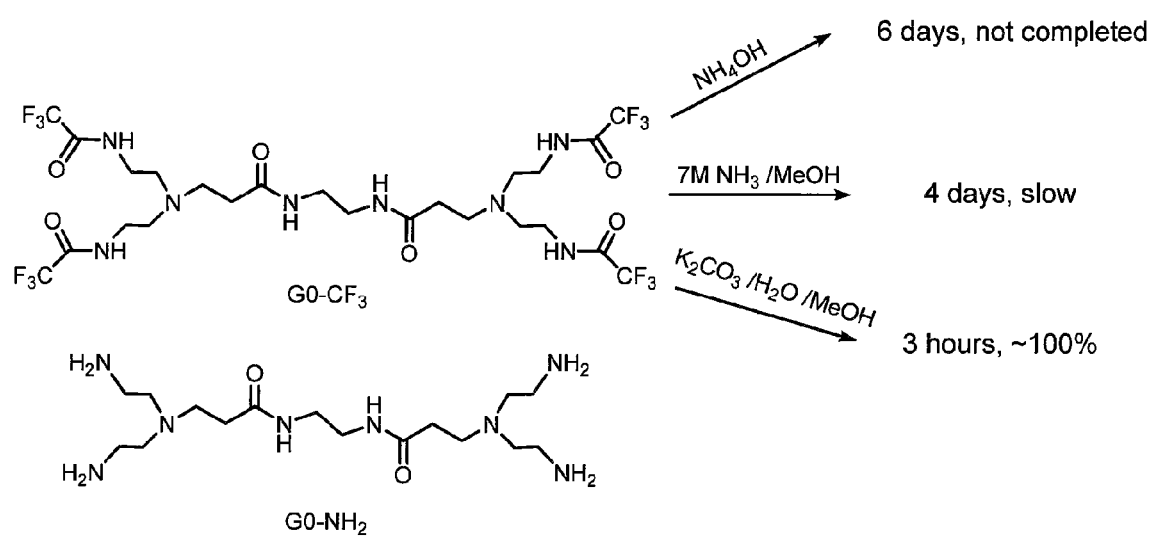
FIG. 9 shows results of different methods used to convert a generation 0 (G0), $CF_3$-terminated Baker-Huang dendrimer to a generation 0 (G0), $NH_2$-terminated Baker-Huang dendrimer.
Figure 13:
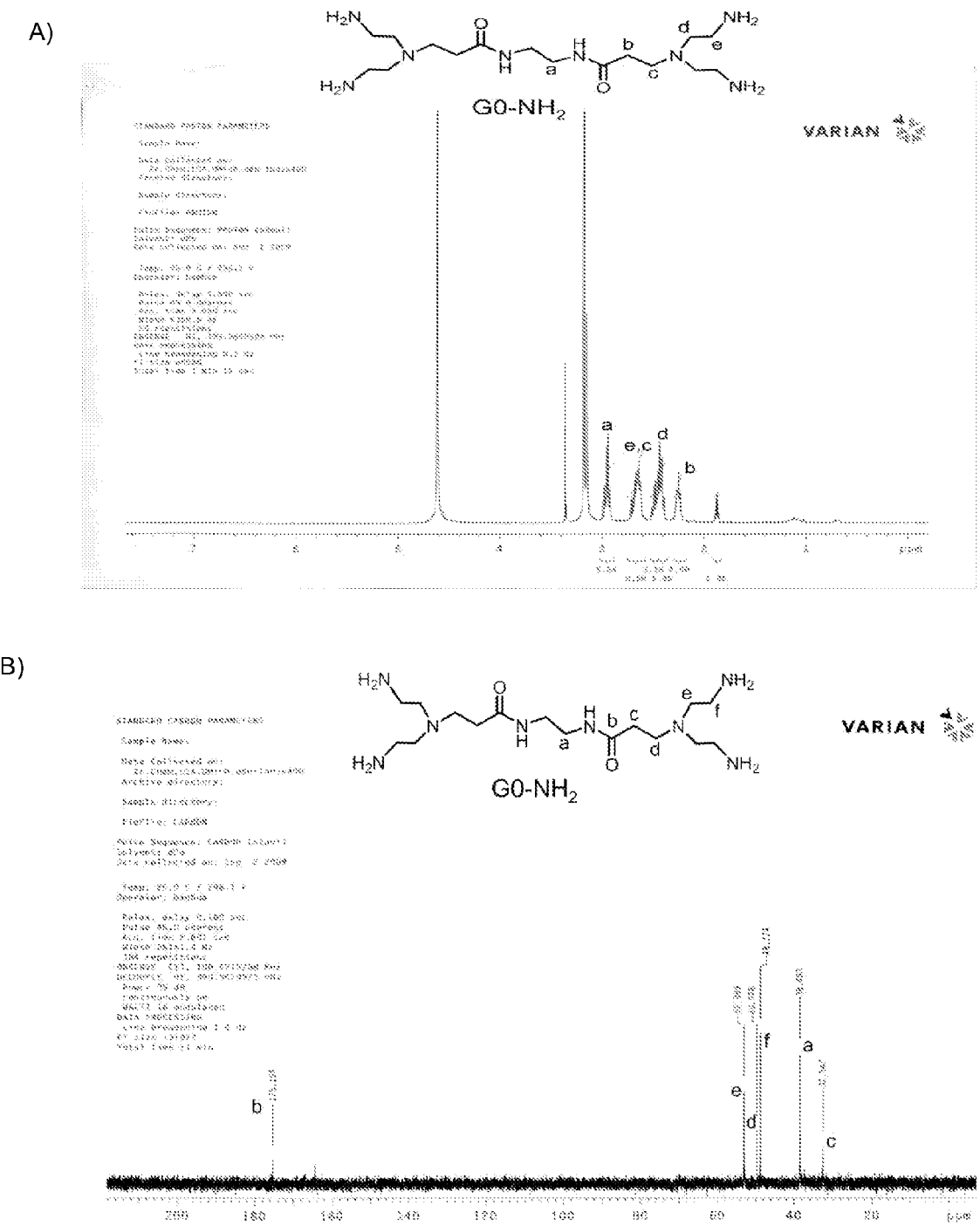
FIG. 13 shows an NMR spectrum generated using one embodiment of a generation 0 (G0) $NH_2$-terminated Baker-Huang PAMAM dendrimer of the present invention, as illustrated on the spectrum. Panel A, approximately 8 ppm to 0 ppm; panel B, approximately 220 ppm to 0 ppm.
Figure 14:
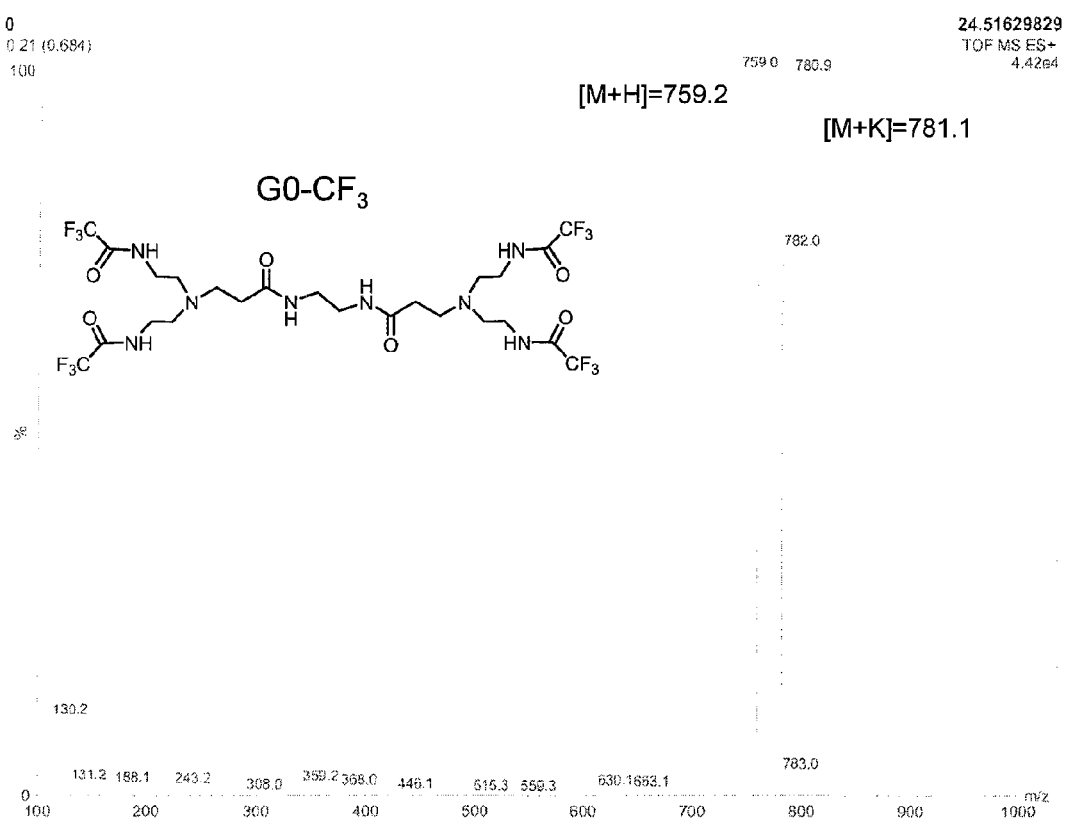
FIG. 14 shows a TOF-MS spectrum generated using one embodiment of a generation 0 (G0) $CF_3$-terminated Baker-Huang PAMAM dendrimer of the present invention, as illustrated on the spectrum.
Figure 15:
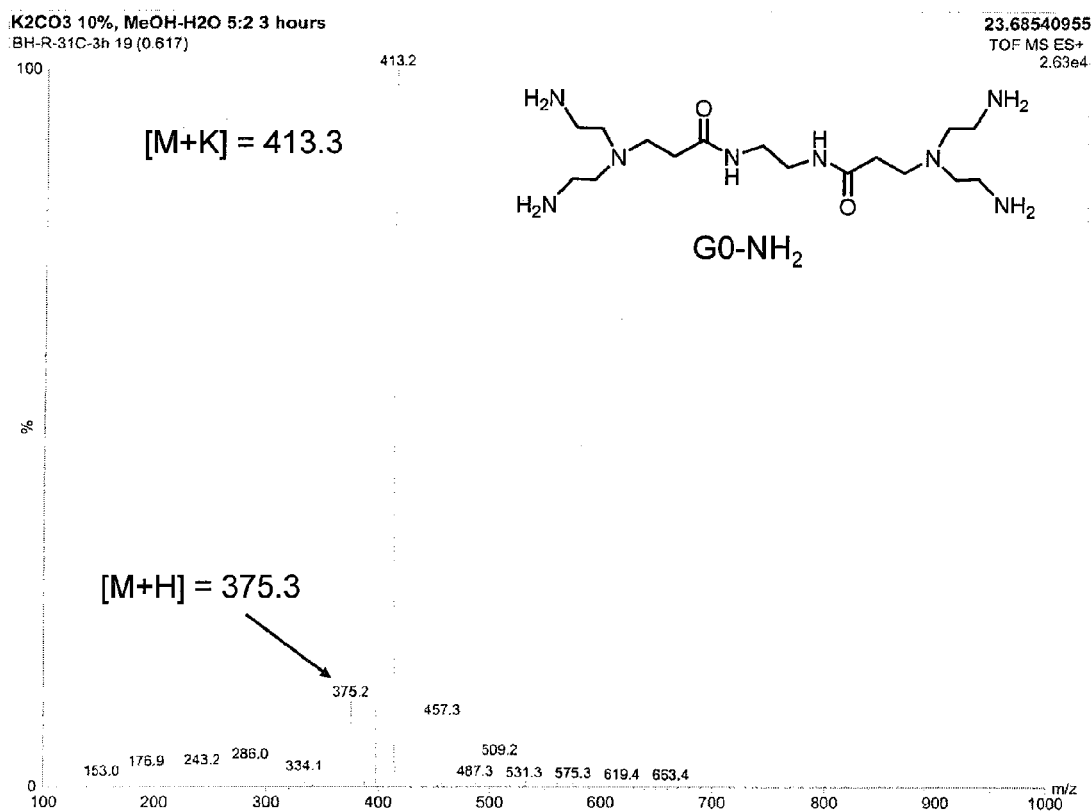
FIG. 15 shows a TOF-MS spectrum generated using one embodiment of a generation 0 (G0) $NH_2$-terminated Baker-Huang PAMAM dendrimer of the present invention, as illustrated on the spectrum.
Figure 16:
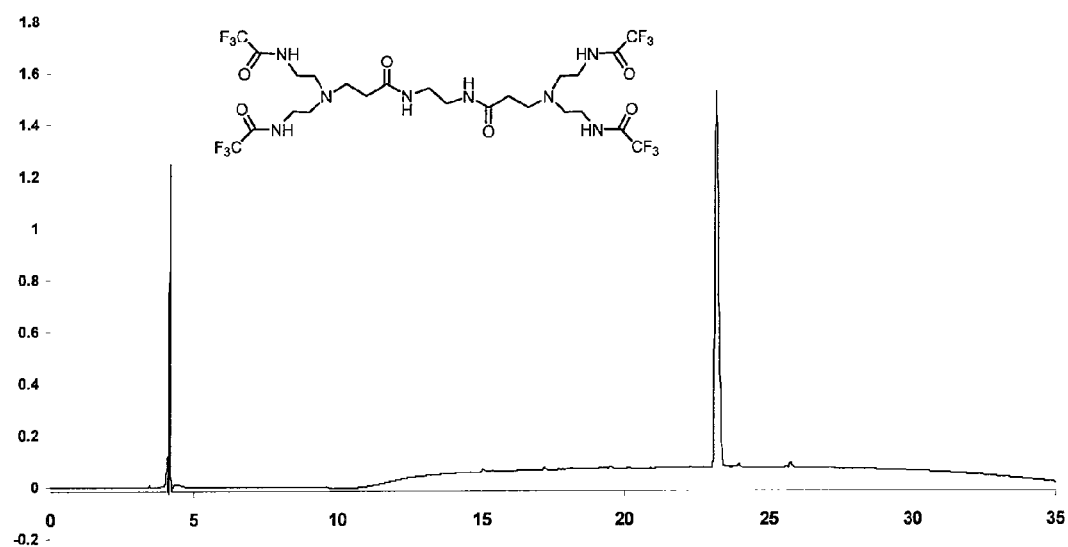
FIG. 16 shows an HPLC chromatogram generated during elution of one embodiment of a generation 0 (G0) $CF_3$-terminated Baker-Huang PAMAM dendrimer of the present invention, as illustrated on the spectrum.
Figure 17:
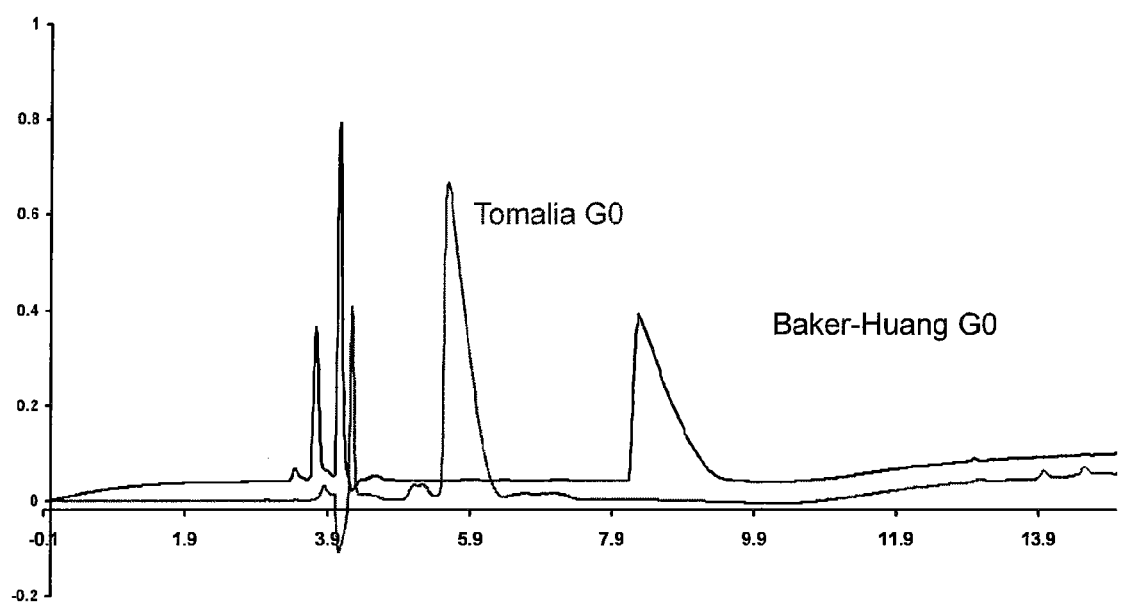
FIG. 17 shows an HPLC chromatogram generated during elution of one embodiment of a generation 0 (G0) $NH_2$-terminated Baker-Huang PAMAM dendrimer of the present invention, as illustrated on the spectrum.

Following synthesis of the $CF_3$-terminated G0 Baker-Huang dendrimer embodiment, deprotection reactions to result in terminal primary amines were attempted using several different strategies, as shown in FIG. 9. Treatment with $NH_4OH$ was incomplete after six days of reaction. Treatment with 7M $NH_3$/MeOH was similarly slow, requiring at least four days of reaction time. However, treatment with $K_2CO_3$/$H_2O$/MeOH achieved nearly 100% completion after 3 hours. Results of structural analysis of the $NH_2$-terminated G0 Baker-Huang dendrimer embodiment are shown in FIGS. 13A and 13B (NMR spectra), FIG. 15 (MS), and FIG. 17 (HPLC).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

---

We claim:
1. A composition comprising a compound having the following formula:
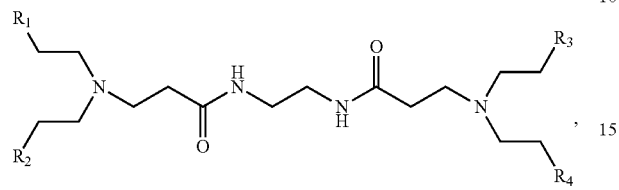
wherein R1, R2, R3, R4 are R5,
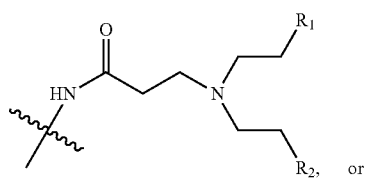 or
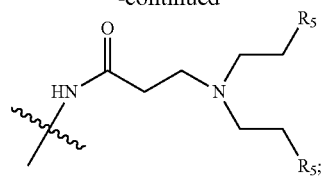
wherein R5 is
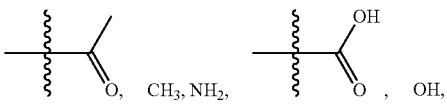
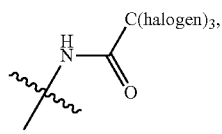
a targeting agent, a therapeutic agent, a pro-drug, an imaging agent, or a trigger agent.
2. The composition of claim 1, said compound having the following formula:
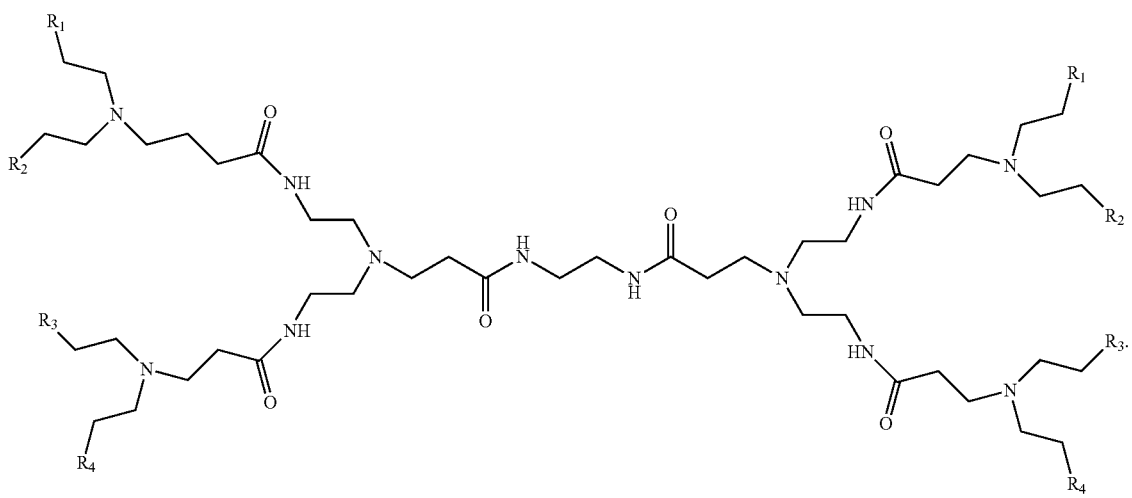

3. The composition of claim 1,
wherein said therapeutic agent if present is selected from the group consisting of chemotherapeutic agents, anti-oncogenic agents, anti-angiogenic agents, tumor suppressor agents, anti-microbial agents, expression constructs comprising a nucleic acid encoding a therapeutic protein, pain relief agents, pain relief agent antagonists, agents designed to treat arthritis, agents designed to treat inflammatory bowel disease, agents designed to treat an autoimmune disease, and agents designed to treat inflammatory pelvic disease;
wherein said targeting agent if present is selected from the group consisting of an agent binding a receptor selected from the group consisting of CFTR, EGFR, estrogen receptor, FGR2, folate receptor, IL-2 receptor, and VEGFR; an antibody that binds to a polypeptide selected from the group consisting of p53, Muc1, a mutated version of p53 that is present in breast cancer, HER-2, T and Tn haptens in glycoproteins of human breast carcinoma, and MSA breast carcinoma glycoprotein; an antibody selected from the group consisting of human carcinoma antigen, TP1 and TP3 antigens from osteocarcinoma cells, Thomsen-Friedenreich (TF) antigen from adenocarcinoma cells, KC-4 antigen from human prostrate adenocarcinoma, human colorectal cancer antigen, CA125 antigen from cystadenocarcinoma, DF3 antigen from human breast carcinoma, and p97 antigen of human melanoma, carcinoma or orosomucoid-related antigen; transferrin; and a synthetic tetanus toxin fragment;
wherein imaging agent if present is selected from the group consisting of fluorescein isothiocyanate (FITC), 6-TAMARA, acridine orange, and cis-parinaric acid;
wherein said trigger agent if present is configured for a function selected from the group consisting of permitting a delayed release of a functional group from the dendrimer, permitting a constitutive release of the therapeutic agent from the dendrimer, permitting a release of a functional group from the dendrimer under conditions of acidosis, permitting a release of a functional group from a dendrimer under conditions of hypoxia, and permitting a release of the therapeutic agent from a dendrimer in the presence of a brain enzyme.

4. The composition of claim 1, wherein said therapeutic agent is methotrexate, and wherein said targeting agent is folic acid.

5. The composition of claim 1, further comprising nanomaterials selected from the group consisting of gold nanoparticles, iron oxide nanoparticles, polymers, silica, albumin, quantum dots, and carbon nanotubes.

6. The composition of claim 1, wherein said compound is selected from the group consisting of

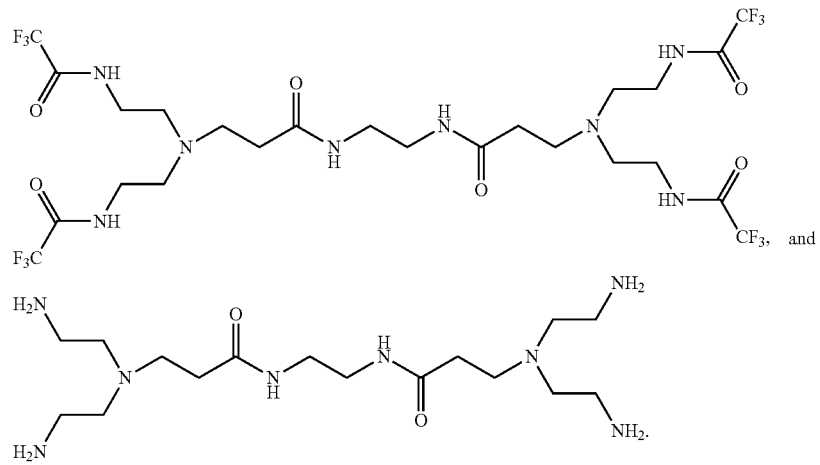

* * * * *

SEQUENCE LISTING

```
<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The residue at this position is linked to a
      (7-methoxycoumarin-4-yl)acetyl
<220> FEATURE:
<221> NAME/KEY: MISC_FEATURE
<222> LOCATION: (7)..(7)
<223> OTHER INFORMATION: The residue at this position is linked to a
      2,4-dinitrophenyl group and NH2

<400> SEQUENCE: 1

Tyr Glu Val Asp Gly Trp Lys
1               5

<210> SEQ ID NO 2
<211> LENGTH: 12
<212> TYPE: PRT
<213> ORGANISM: Artificial Sequence
<220> FEATURE:
<223> OTHER INFORMATION: Synthetic

<400> SEQUENCE: 2

His Leu Asn Ile Leu Ser Thr Leu Trp Lys Tyr Arg
1               5                   10
```